United States Patent
Kim et al.

(10) Patent No.: US 10,772,606 B2
(45) Date of Patent: Sep. 15, 2020

(54) METHOD AND APPARATUS FOR DISPLAYING ULTRASOUND IMAGES

(71) Applicant: SAMSUNG MEDISON CO., LTD., Hongcheon-gun (KR)

(72) Inventors: Han-jun Kim, Hongcheon-gun (KR); Sung-yoon Kim, Hongcheon-gun (KR); Jun-sang Yoo, Hongcheon-gun (KR); Kwang-hee Lee, Hongcheon-gun (KR); Gil-ju Jin, Hongcheon-gun (KR); Mi-jeoung Ahn, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 430 days.

(21) Appl. No.: 15/165,138

(22) Filed: May 26, 2016

(65) Prior Publication Data
US 2016/0361043 A1 Dec. 15, 2016

Related U.S. Application Data

(60) Provisional application No. 62/174,619, filed on Jun. 12, 2015.

(30) Foreign Application Priority Data

Dec. 24, 2015 (KR) .................. 10-2015-0186771

(51) Int. Cl.
*A61B 8/00* (2006.01)
*A61B 8/08* (2006.01)
(Continued)

(52) U.S. Cl.
CPC ............ *A61B 8/463* (2013.01); *A61B 8/0808* (2013.01); *A61B 8/0866* (2013.01);
(Continued)

(58) Field of Classification Search
CPC ....... A61B 8/463; A61B 8/483; A61B 8/0866; A61B 8/0808; A61B 8/0875;
(Continued)

(56) References Cited

U.S. PATENT DOCUMENTS 7,507,204 B2   3/2009  Shim et al.
8,600,129 B2  12/2013  Seko et al.
(Continued)

FOREIGN PATENT DOCUMENTS

CN  103156638 A  6/2013
CN  103908299 A  7/2014
(Continued)

OTHER PUBLICATIONS

Communication dated Nov. 17, 2016, issued by the European Patent Office in counterpart European Application No. 16168797.5.
(Continued)

*Primary Examiner* — Sanjay Cattungal
(74) *Attorney, Agent, or Firm* — Sughrue Mion, PLLC

(57) ABSTRACT

Provided is an ultrasound diagnosis apparatus including: a display configured to display a first ultrasound image showing an object; a user input device configured to receive a user input for selecting first and second depths in the first ultrasound image and setting different three-dimensional (3D) rendering properties with respect to the first and second depths; and a controller configured to generate a second ultrasound image showing a 3D volume of the object based on the set 3D rendering properties, wherein the display is further configured to display the generated second ultrasound image.

14 Claims, 52 Drawing Sheets

(51) Int. Cl.
*A61B 8/14* (2006.01)
*G06T 15/08* (2011.01)

(52) U.S. Cl.
CPC .......... *A61B 8/0875* (2013.01); *A61B 8/0891* (2013.01); *A61B 8/14* (2013.01); *A61B 8/466* (2013.01); *A61B 8/469* (2013.01); *A61B 8/483* (2013.01); *A61B 8/5207* (2013.01); *A61B 8/54* (2013.01); *G06T 15/08* (2013.01)

(58) Field of Classification Search
CPC ........... A61B 8/0891; A61B 8/14; A61B 8/54; A61B 8/466; A61B 8/469; A61B 8/5207; A61B 2576/02; A61B 8/5215; G06T 15/08; G06T 2210/41; G06T 15/205
USPC .................................................. 600/437–469
See application file for complete search history.

(56) References Cited

U.S. PATENT DOCUMENTS

| | | | |
|---|---|---|---|
| 8,884,958 B2 | 11/2014 | Tsukagoshi et al. | |
| 9,301,733 B2 | 4/2016 | Gerard et al. | |
| 2009/0306503 A1* | 12/2009 | Srinivasan | A61B 8/00 600/441 |
| 2012/0190984 A1* | 7/2012 | Kim | A61B 8/14 600/443 |
| 2013/0150718 A1* | 6/2013 | Dixon | A61B 8/4483 600/443 |
| 2013/0150719 A1* | 6/2013 | Orderud | G06T 15/08 600/443 |
| 2014/0018682 A1 | 1/2014 | Baba | |
| 2014/0139526 A1* | 5/2014 | Kim | G06T 7/0012 345/424 |
| 2014/0187948 A1 | 7/2014 | Gerard et al. | |

FOREIGN PATENT DOCUMENTS

| | | |
|---|---|---|
| JP | 2010-51817 A | 3/2010 |
| JP | 2010115372 A | 5/2010 |
| JP | 2013-16153 A | 1/2013 |
| JP | 5226887 B2 | 7/2013 |
| JP | 5230589 B2 | 7/2013 |
| JP | 5437768 B2 | 3/2014 |
| KR | 10-0686289 B1 | 2/2007 |

OTHER PUBLICATIONS

Communication dated Mar. 31, 2020 issued by the State Intellectual Property Office of P.R. China in counterpart Chinese Application No. 201610407119.X.

* cited by examiner

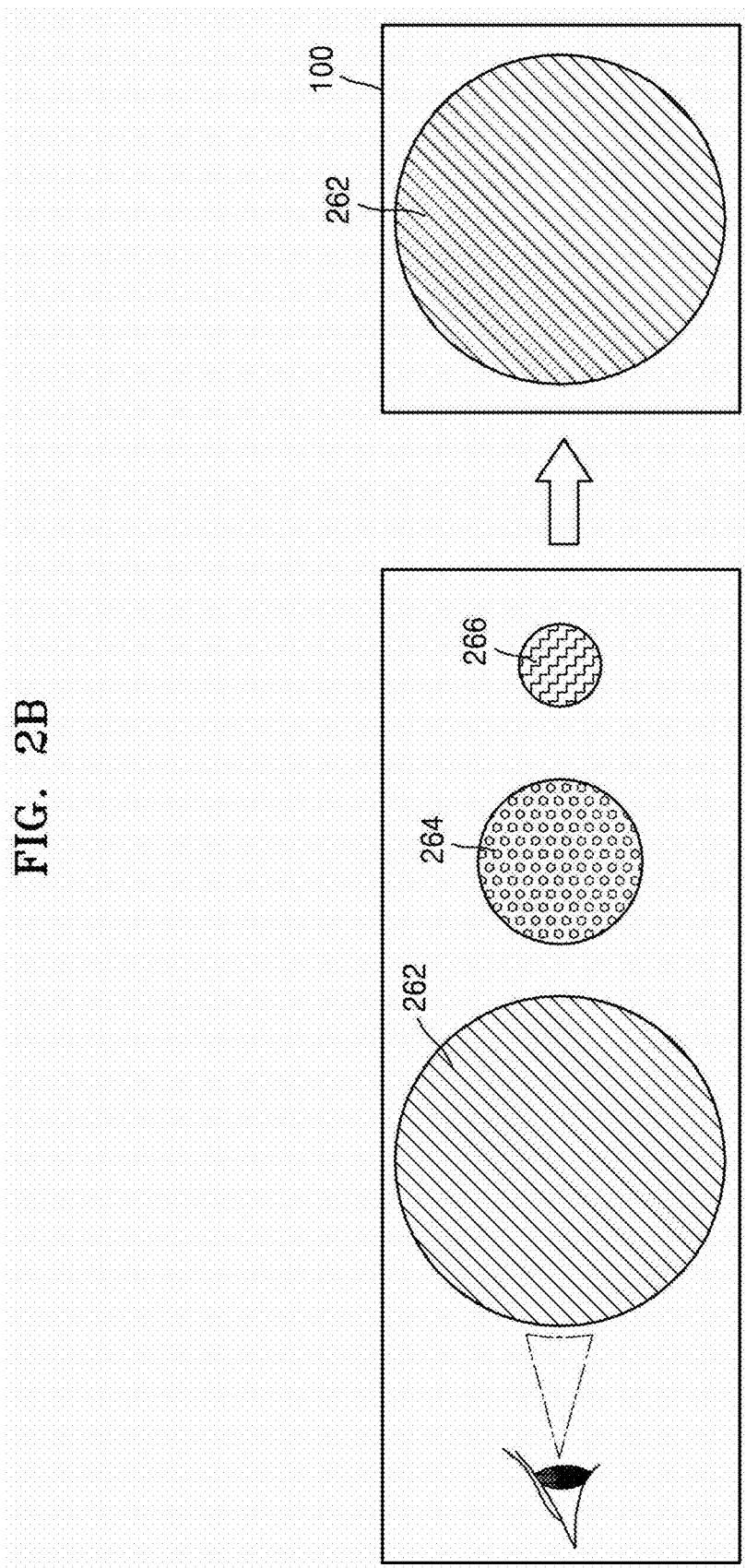

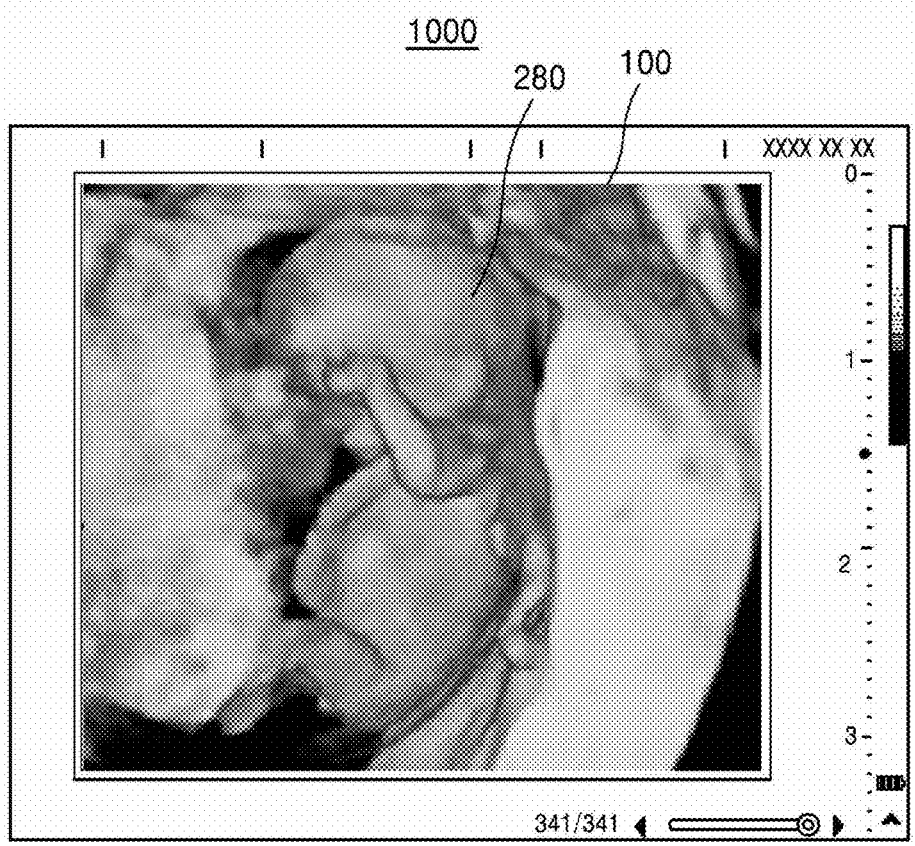

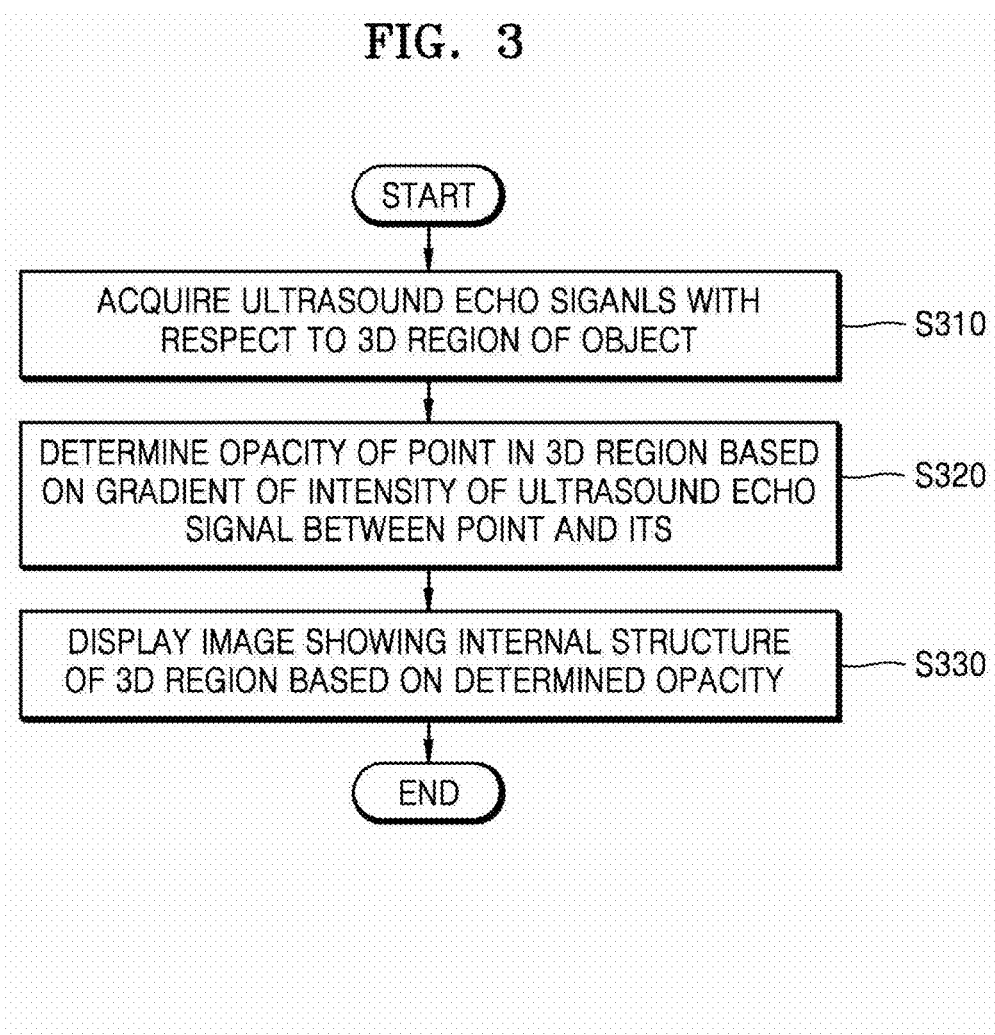

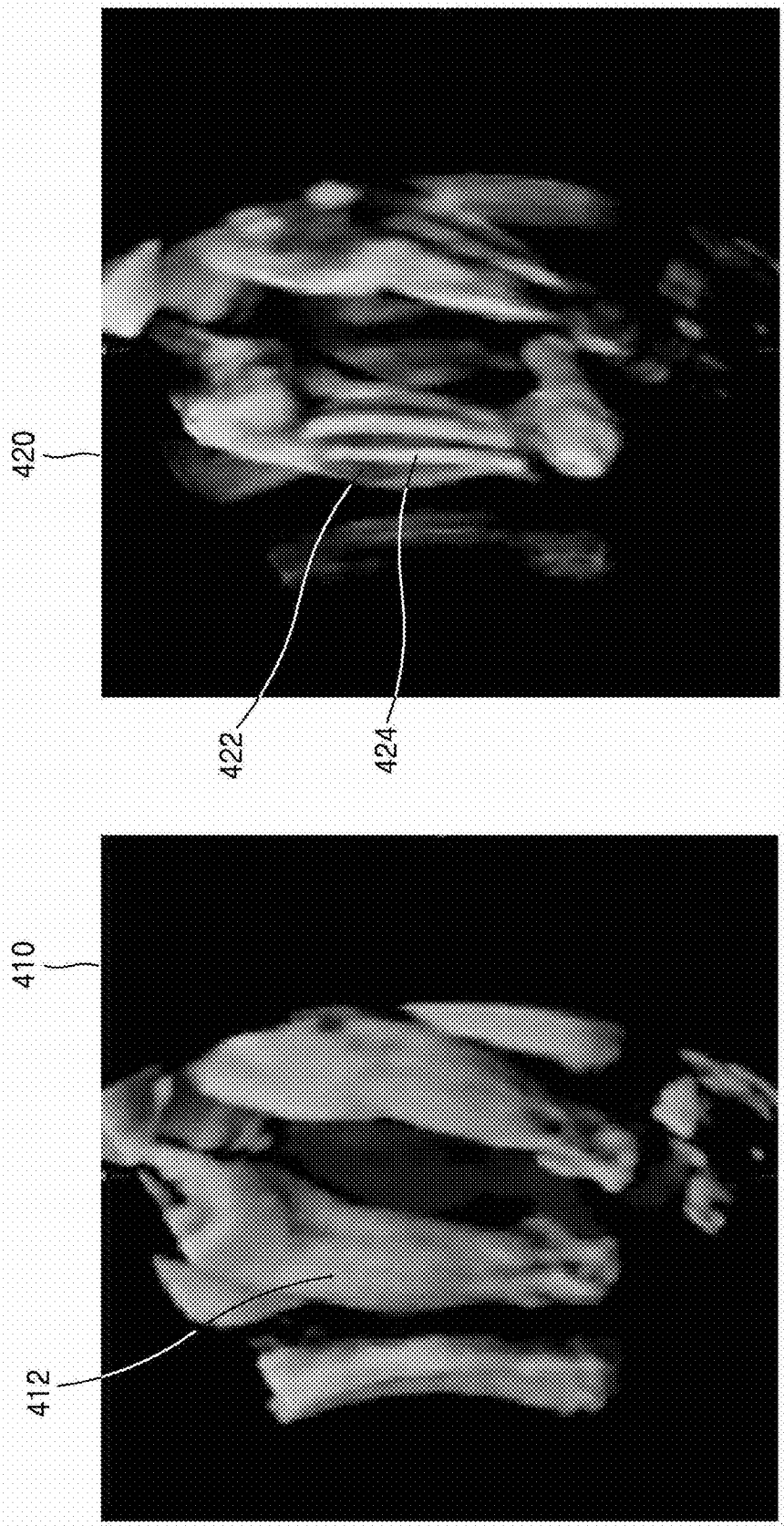

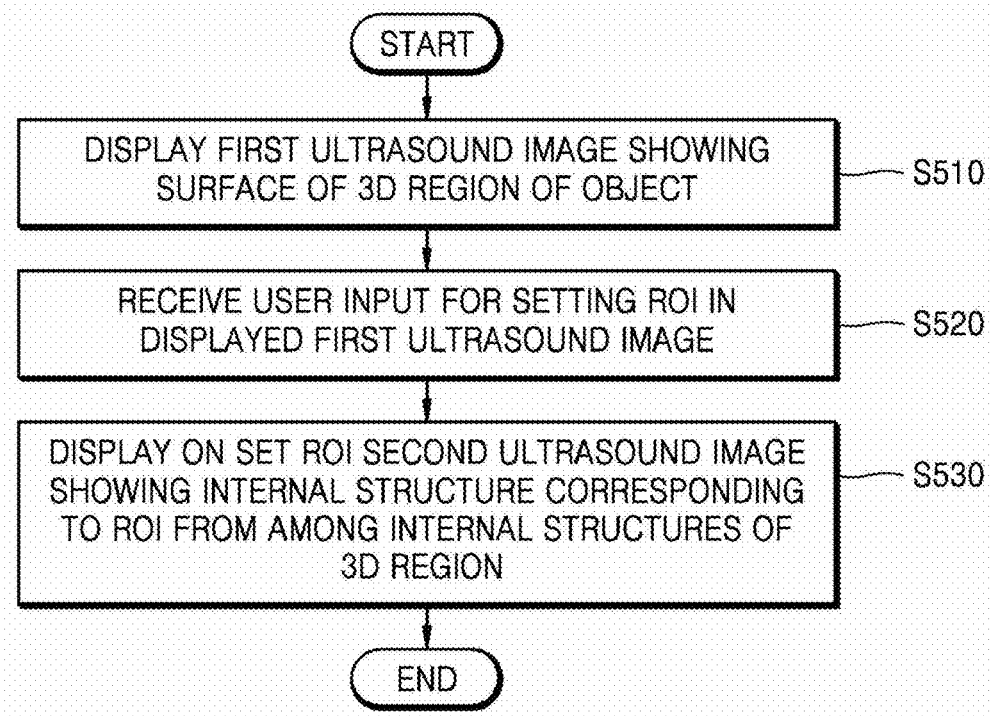

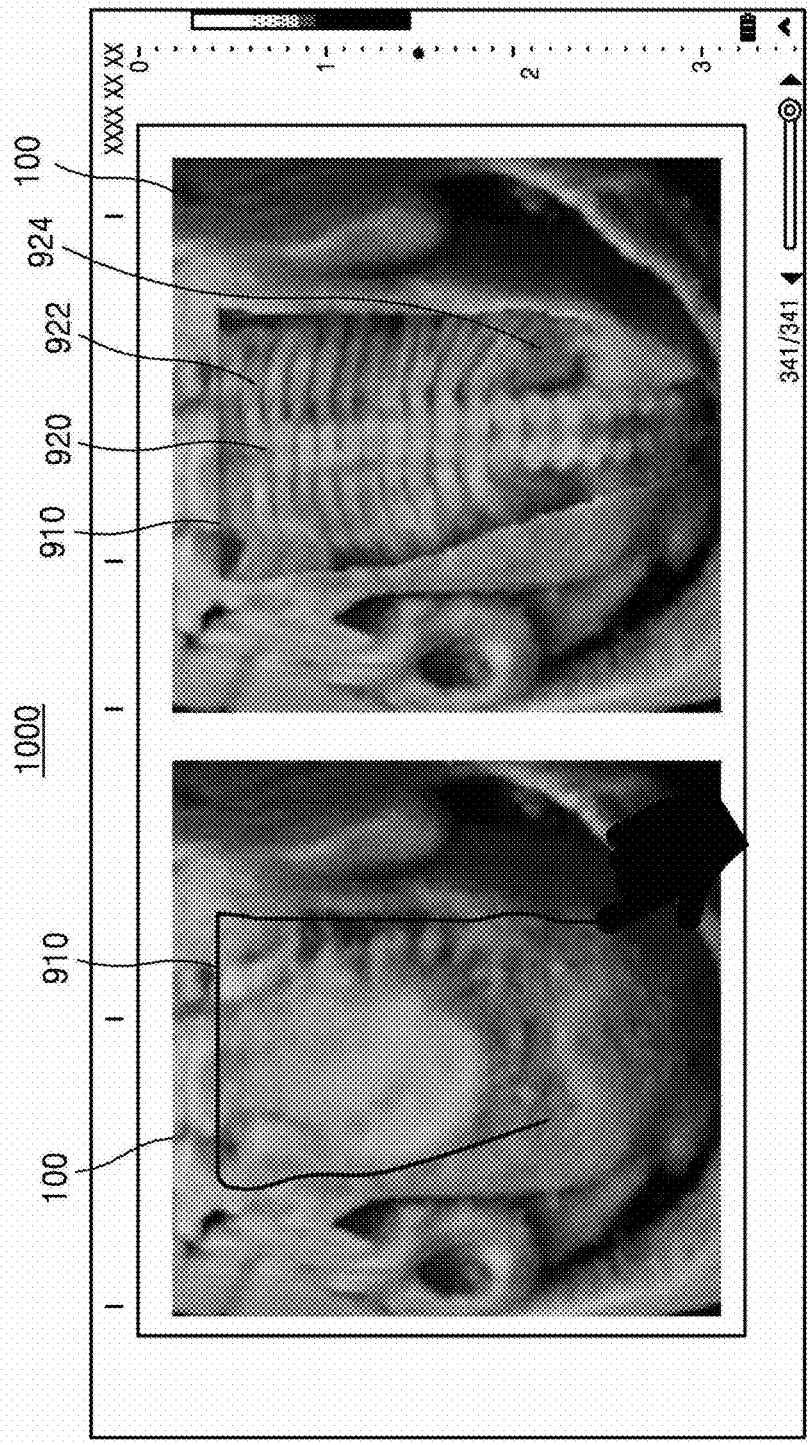

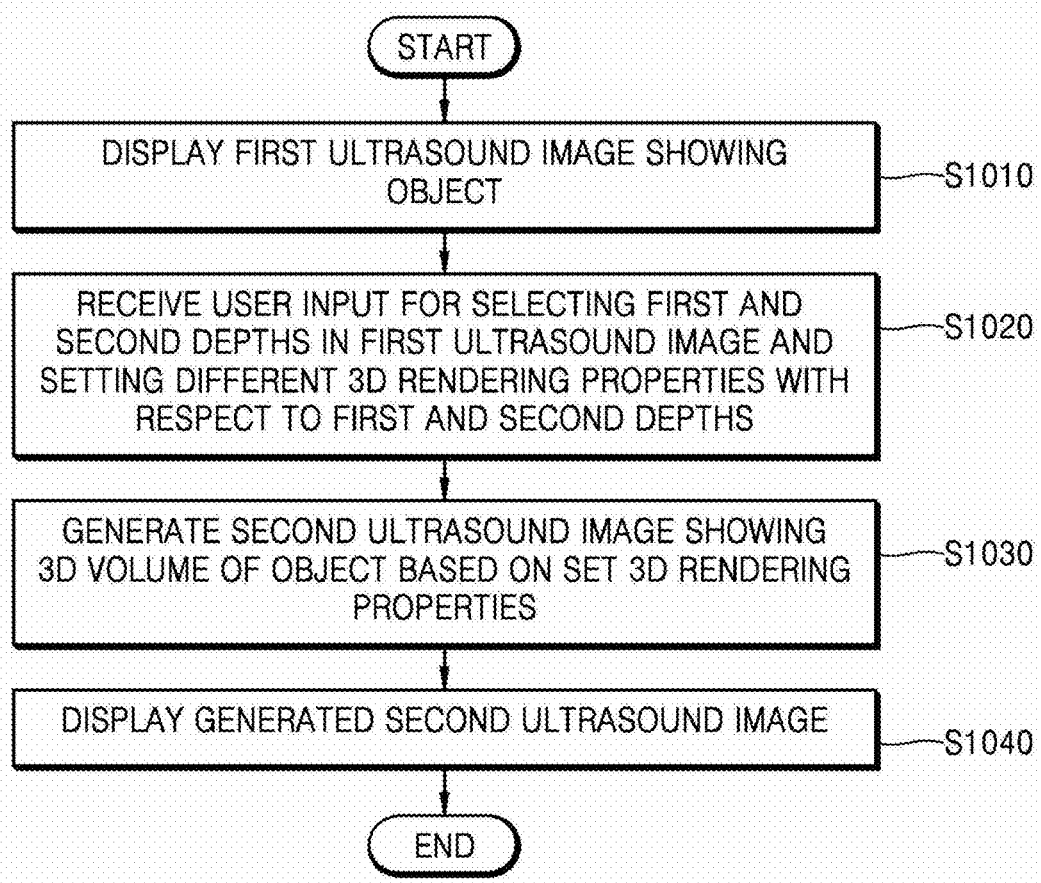

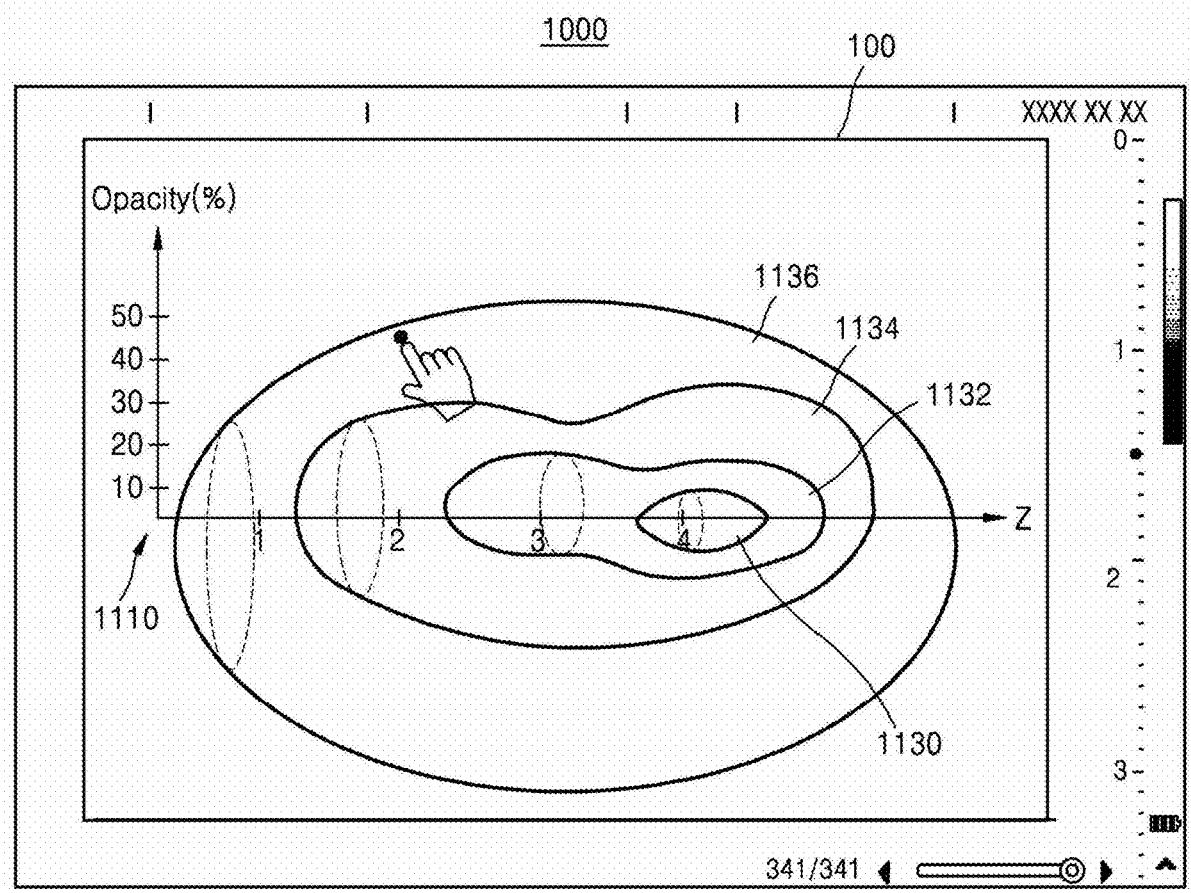

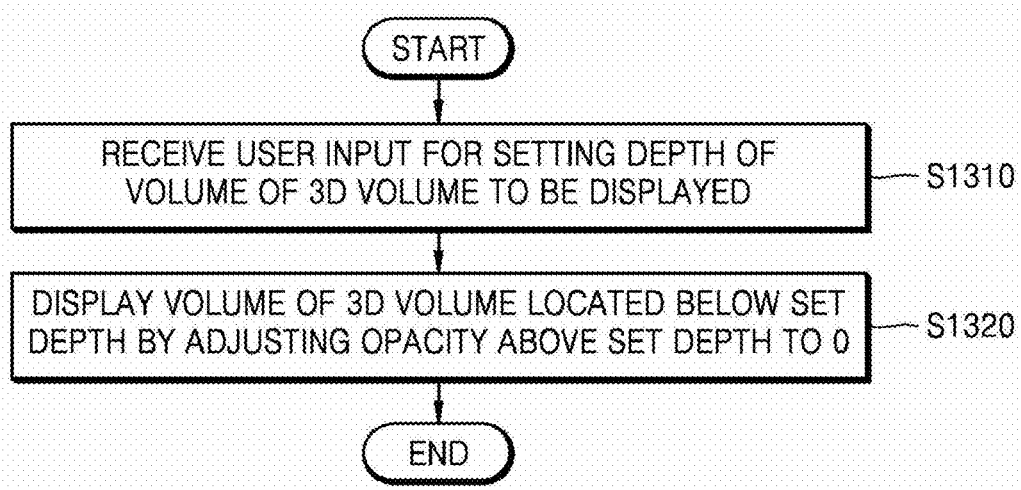
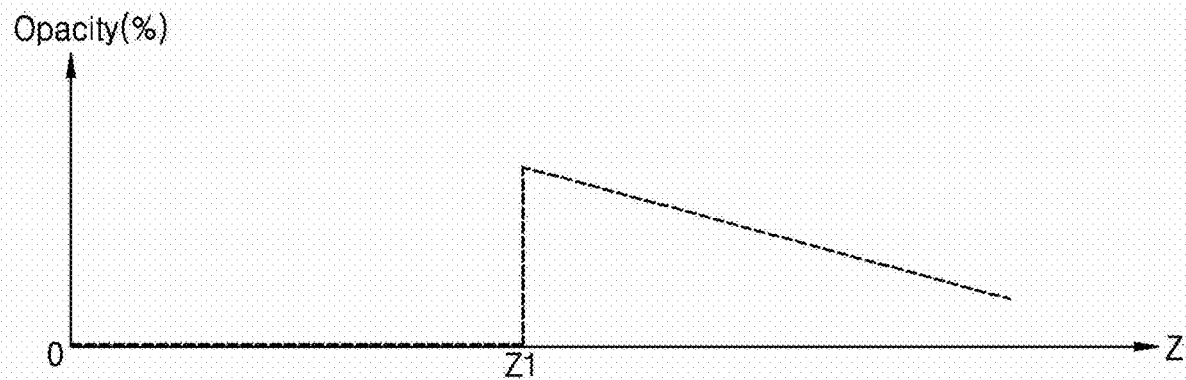

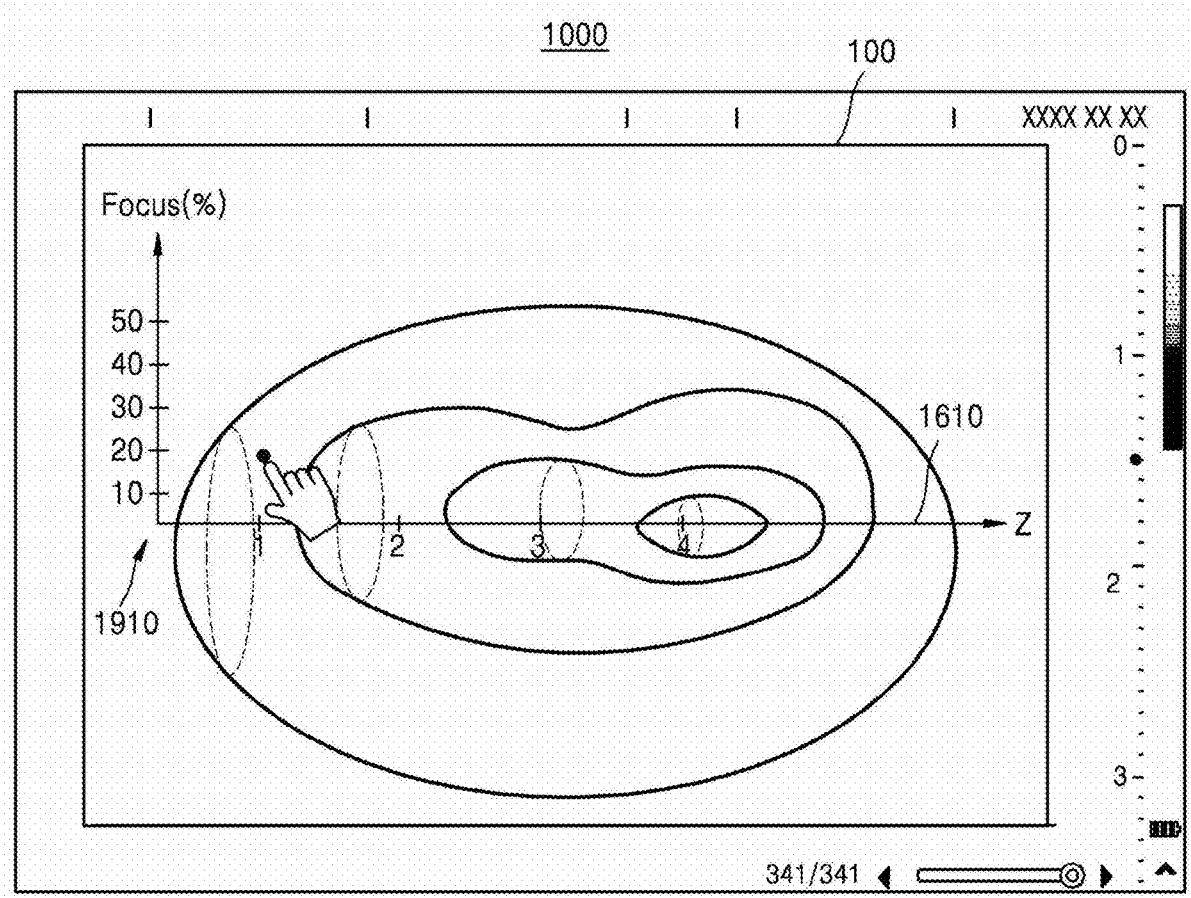

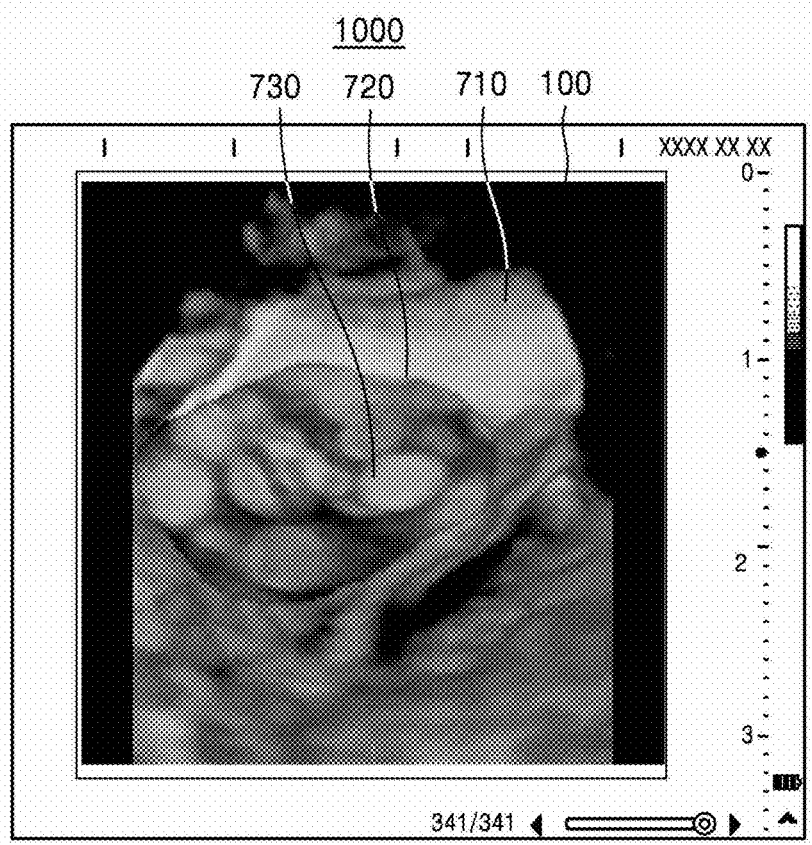

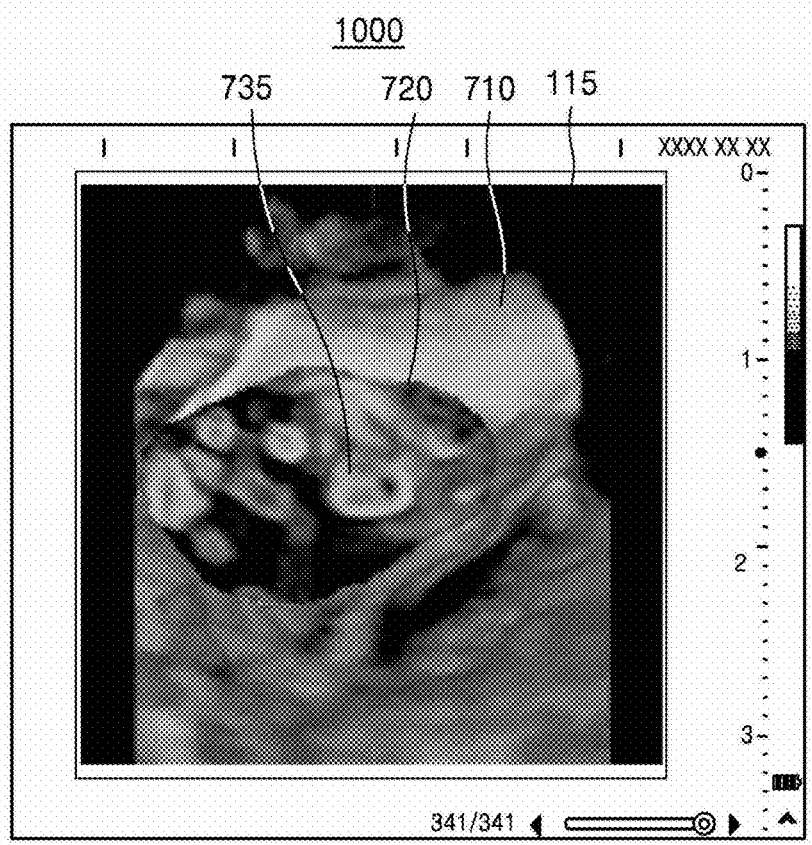

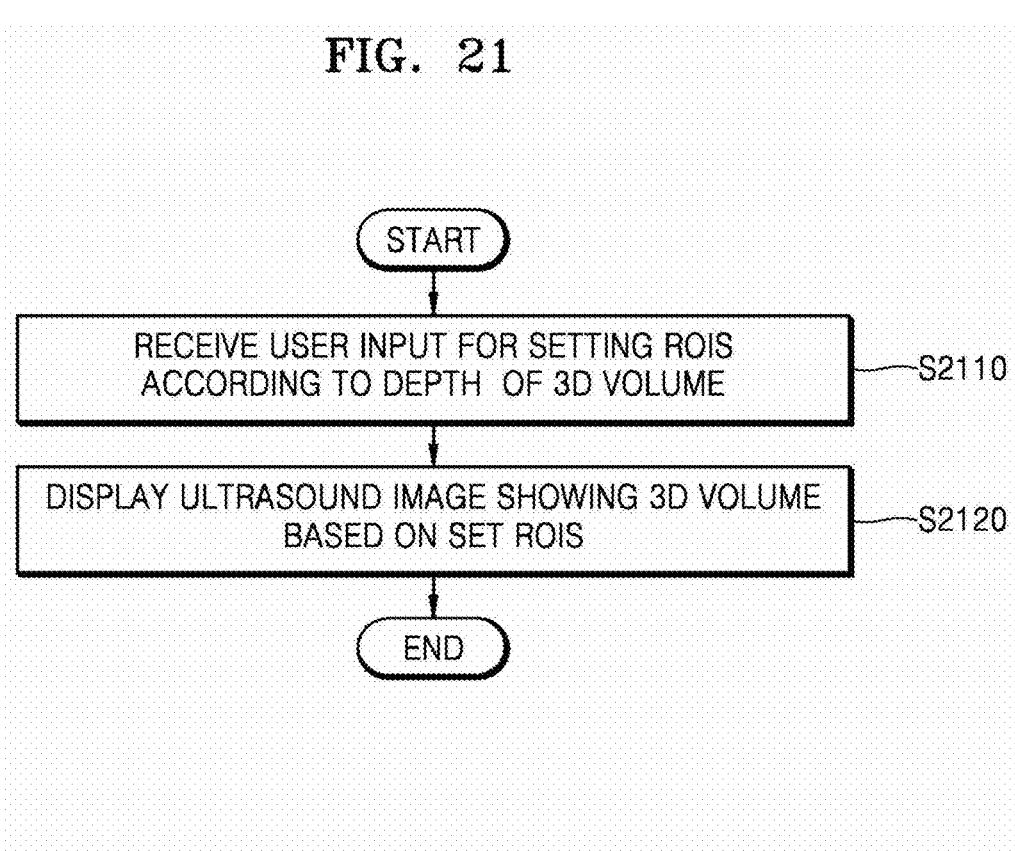

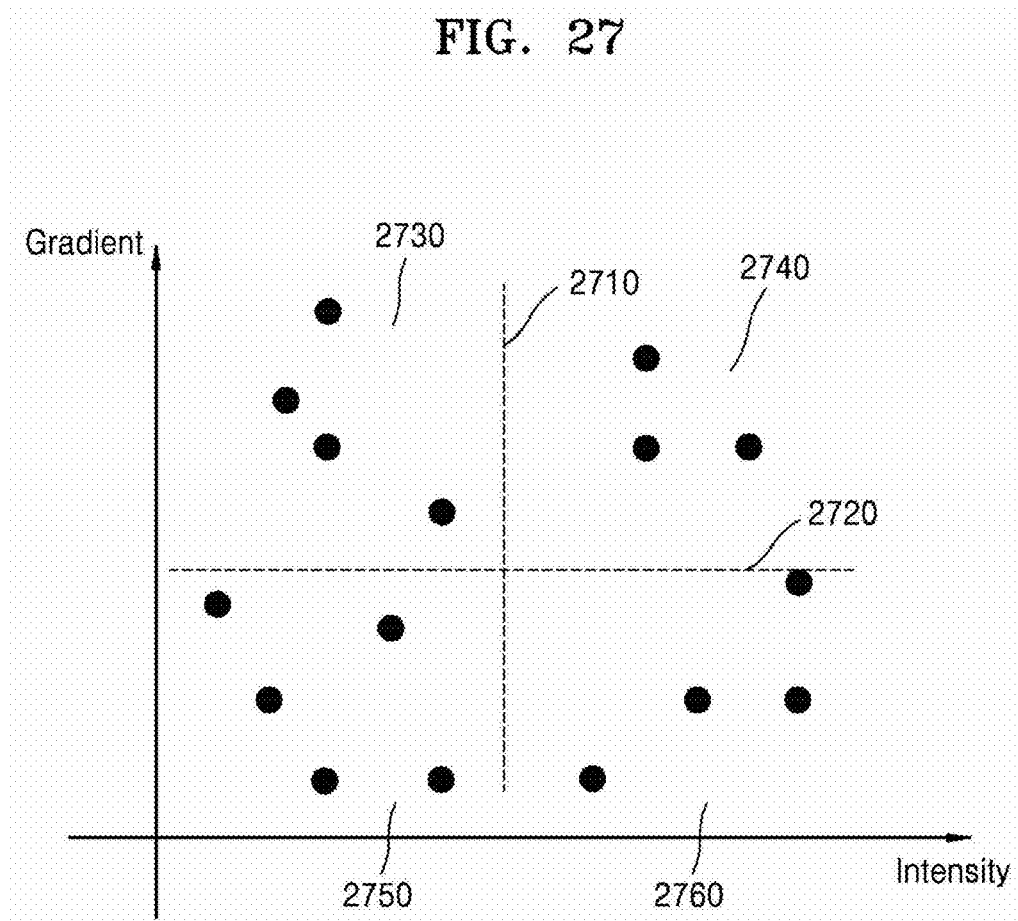

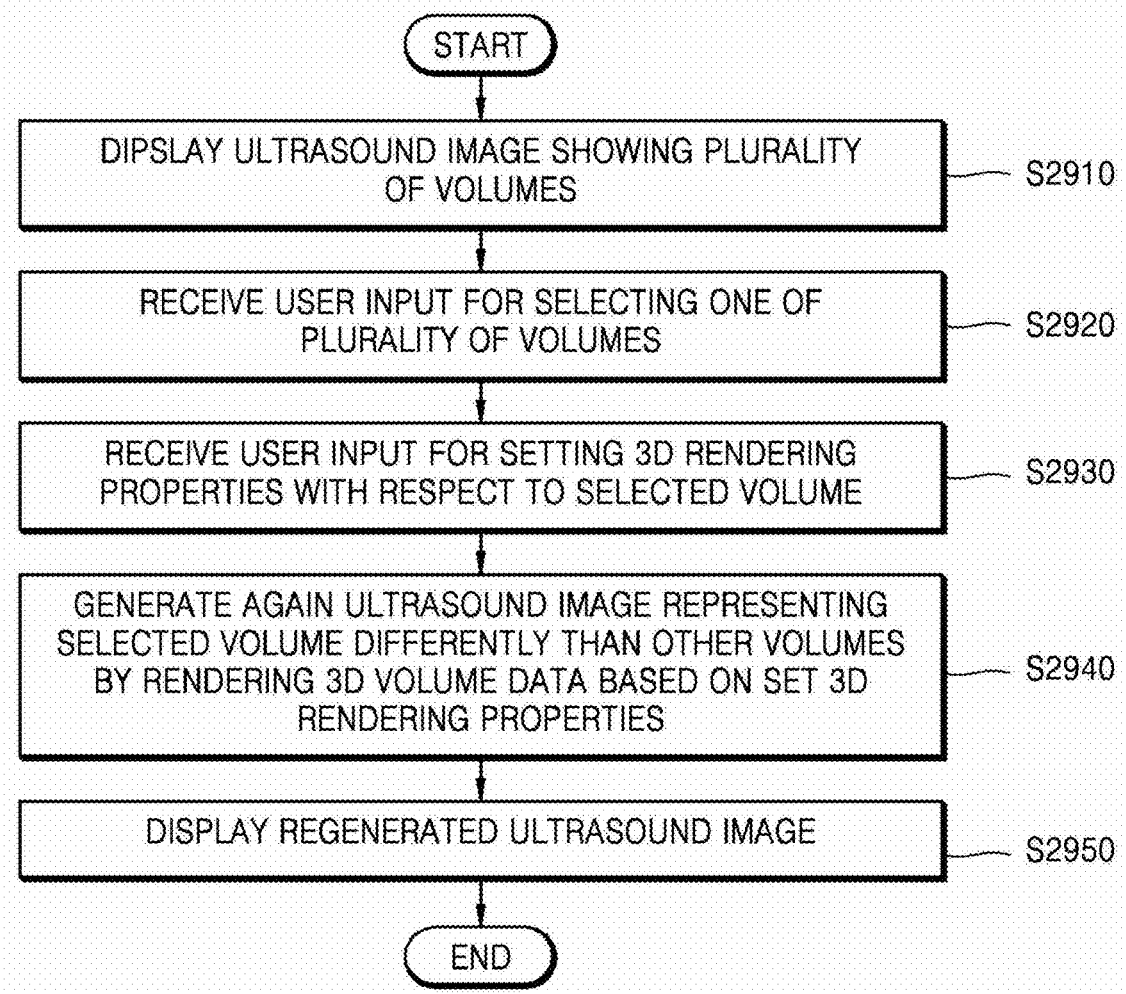

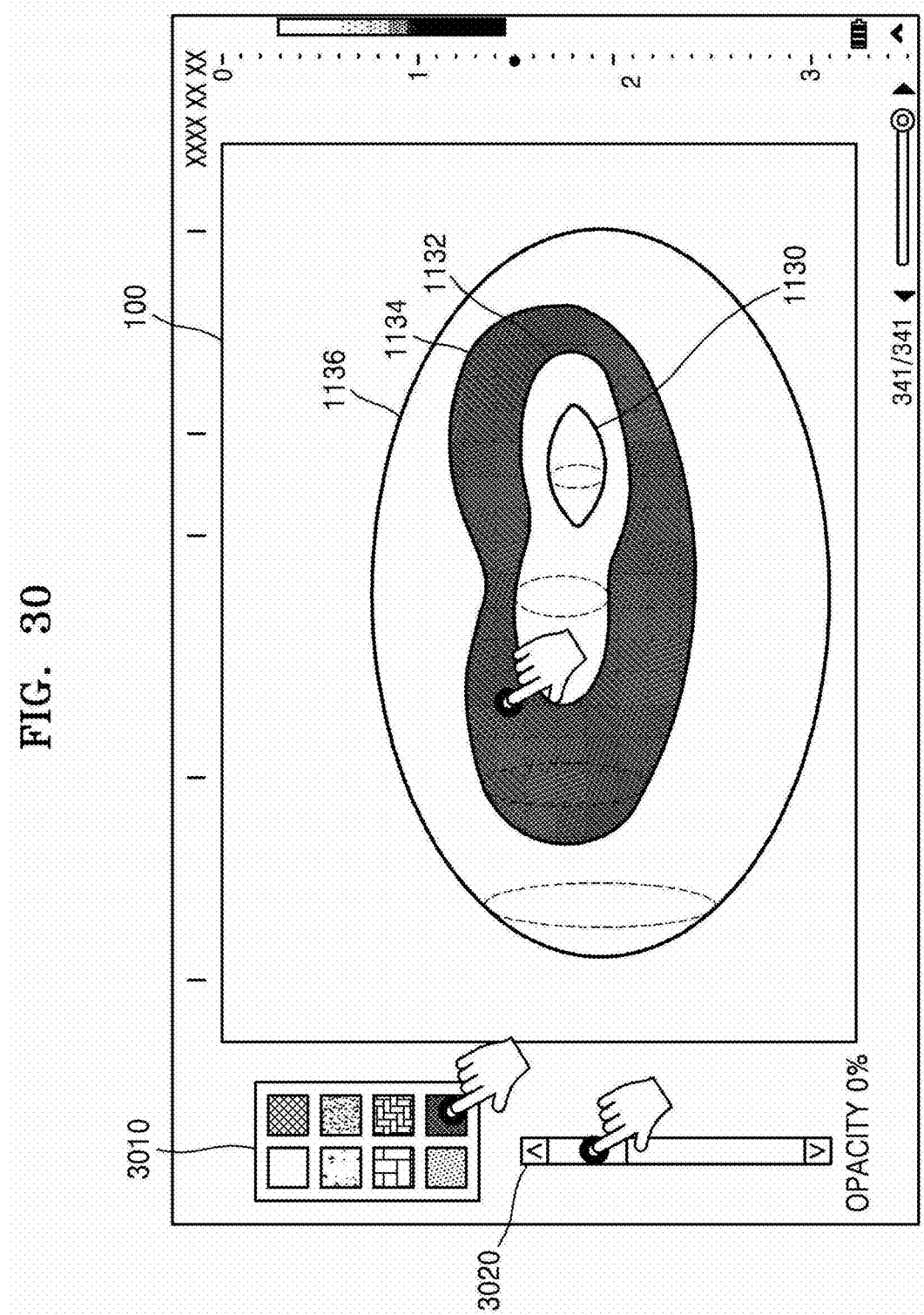

METHOD AND APPARATUS FOR DISPLAYING ULTRASOUND IMAGES

CROSS-REFERENCE TO RELATED APPLICATIONS

This application claims the benefit of U.S. Provisional Application No. 62/174,619, filed on Jun. 12, 2015, in the US Patent Office and Korean Patent Application No. 10-2015-0186771, filed on Dec. 24, 2015, in the Korean Intellectual Property Office, the disclosures of which are incorporated herein in their entireties by reference.

BACKGROUND

1. Field

The present disclosure relates to methods and apparatuses for displaying a three-dimensional (3D) region of an object.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissue or blood flow). In particular, ultrasound diagnosis apparatuses are used for medical purposes including observing an internal area of an object, detecting foreign substances, and assessing injuries. Such ultrasound diagnosis apparatuses provide high stability, display images in real time, and are safe due to no radiation exposure, compared to X-ray apparatuses. Therefore, an ultrasound diagnosis apparatus is widely used together with other types of imaging diagnosis devices including a computed tomography (CT) apparatus, a magnetic resonance imaging (MRI) apparatus, and the like.

SUMMARY

Provided are methods and apparatuses for displaying an internal structure of a three-dimensional (3D) region of an object.

Provided are methods and apparatuses for setting a region of interest (ROI) in an ultrasound image representing a surface of a 3D region of an object and displaying an internal structure of the 3D region on the set ROI.

Provided are methods of and apparatuses for displaying an ultrasound image representing a 3D region by setting a plurality of ROIs according to a depth and applying different rendering parameters to the set ROIs.

Provided are methods of and apparatuses for displaying an ultrasound image representing a plurality of volumes differently segmenting a 3D volume of an object into the plurality of volumes and applying different rendering parameters to the plurality of volumes.

Additional aspects will be set forth in part in the description which follows and, in part, will be apparent from the description, or may be learned by practice of the presented embodiments.

According to an aspect of an embodiment, an ultrasound diagnosis apparatus includes: a user input device configured to receive a user input for selecting first and second depths in the first ultrasound image and setting different three-dimensional (3D) rendering properties with respect to the first and second depths; and a controller configured to generate a second ultrasound image showing a 3D volume of the object based on the set 3D rendering properties, wherein the display is further configured to display the generated second ultrasound image.

The 3D rendering properties may include at least one of an opacity, a color, a region of interest (ROI), and a degree of focus.

The first depth may include a first depth interval in the 3D volume, and the second depth comprises a second depth interval in the 3D volume.

The controller is further configured to control the display to display an indicator representing a direction of a depth for which the 3D rendering properties are to be set.

The display is further configured to display a plurality of ultrasound images showing different cross-sections of the object, and the user input device is further configured to receive a user input for selecting one of the plurality of ultrasound images as the first ultrasound image.

The display is further configured to display a plurality of images respectively representing patterns of the 3D rendering properties according to depths, and the user input device is further configured to receive the user input for selecting the first and second depths in the first ultrasound image and setting different 3D rendering properties with respect to the first and second depths by receiving a user input for selecting one of the plurality of images.

The first ultrasound image may be an ultrasound image showing the 3D volume of the object.

The display is further configured to display an indicator representing a direction of a depth for which the different 3D rendering properties are to be set and a user interface for setting an ROI in a cross-section perpendicular to the direction of the depth, and the user input device is further configured to receive a user input for respectively setting first and second ROIs at the first and second depths by using the user interface and receive a user input for setting different 3D rendering properties with respect to the first and second ROIs.

The user interface for setting the ROI may include a user interface for setting at least one of a shape and a size of the ROI, and the user input device is further configured to receive a user input for setting the first and second ROIs by receiving a user input for setting at least one of a shape and a size of each of the first and second ROIs by using the user interface.

The controller is further configured to control the display to display, when the user input for setting the first and second ROIs is received, a third image showing a cross-section at the first depth and the first ROI, which is set in the cross-section at the first depth, on the third image, and display a fourth image showing a cross-section at the second depth and the second ROI, which is set in the cross-section at the second depth, on the fourth image.

According to an aspect of another embodiment, a method of displaying an ultrasound image includes: displaying a first ultrasound image showing an object; receiving a user input for selecting first and second depths in the first ultrasound image and setting different 3D rendering properties with respect to the first and second depths; generating a second ultrasound image showing a 3D volume of the object based on the set 3D rendering properties; and displaying the generated second ultrasound image.

The 3D rendering properties may include at least one of an opacity, a color, an ROI, and a degree of focus.

The first depth may include a first depth interval in the 3D volume, and the second depth comprises a second depth interval in the 3D volume.

The displaying of the first ultrasound image showing the object may include displaying an indicator representing a direction of a depth for which the 3D rendering properties are to be set.

The displaying of the first ultrasound image showing the object may include: displaying a plurality of ultrasound images showing different cross-sections of the object; receiving a user input for selecting one of the plurality of ultrasound images as the first ultrasound image; and displaying the selected first ultrasound image.

The receiving of the user input for selecting the first and second depths in the first ultrasound image and setting the different 3D rendering properties with respect to the first and second depths may include: displaying a plurality of images respectively representing patterns of the 3D rendering properties according to depths, and receiving the user input for selecting the first and second depths in the first ultrasound image and setting the different 3D rendering properties with respect to the first and second depths by receiving a user input for selecting one of the plurality of images.

The first ultrasound image may be an ultrasound image showing the 3D volume of the object.

The method may further include: displaying an indicator representing a direction of a depth for which the different 3D rendering properties are to be set and a user interface for setting an ROI in a cross-section perpendicular to the direction of the depth; receiving a user input for respectively setting first and second ROIs at the first and second depths by using the user interface; and receiving a user input for setting different 3D rendering properties with respect to the first and second ROIs.

The user interface for setting the ROI may include a user interface for setting at least one of a shape and a size of the ROI, and the receiving of the user input for setting the different 3D rendering properties with respect to the first and second ROIs may include receiving a user input for setting at least one of a shape and a size of each of the first and second ROIs by using the user interface.

The method may further include: displaying, when the user input for setting the first and second ROIs is received, a third image showing a cross-section at the first depth and displaying the first ROI, which is set in the cross-section at the first depth, on the third image; and displaying a fourth image showing a cross-section at the second depth and displaying the second ROI, which is set in the cross-section at the second depth, on the fourth image.

According to an aspect of another embodiment, an ultrasound diagnosis apparatus includes: An ultrasound diagnosis apparatus comprising: a data acquisition unit configured to acquire a three-dimensional volume of an object; a controller configured to segment the 3D volume of the object into a plurality of volumes and render first and second volumes from among the plurality of volumes based on different 3D rendering properties to thereby generate an ultrasound image representing the first and second volumes differently; and a display configured to display the generated ultrasound image.

The controller is further configured to generate an ultrasound image representing the second volume in a more emphasized manner than the first volume by setting opacity of the second volume to be higher than opacity of the first volume.

The controller is further configured to generate an ultrasound image representing the first and second volumes in such a manner as to distinguish them from each other by setting colors for the first and second volumes differently.

The controller is further configured to generate an ultrasound image representing the second volume in a more emphasized manner than the first volume by setting a degree of focus of the second volume to be higher than a degree of focus of the first volume.

The controller is further configured to segment the 3D volume of the object into a plurality of volumes representing internal structures in the 3D volume of the object and render the plurality of volumes based on 3D rendering properties respectively corresponding to the internal structures to thereby generate an ultrasound image representing the first and second volumes differently.

The display is further configured to display an ultrasound image showing the plurality of volumes, and the ultrasound diagnosis apparatus may further include a user input device configured to receive a user input for selecting the first volume from among the plurality of volumes. The controller is further configured to generate the ultrasound image representing the first volume differently than the other volumes by rendering the first volume based on different 3D rendering properties than the other volumes.

The controller is further configured to segment the 3D volume into the plurality of volumes based on a gradient between points in the 3D volume.

The controller is further configured to segment the 3D volume into the plurality of volumes based on an entropy value of the 3D volume.

According to an aspect of another embodiment, an ultrasound diagnosis apparatus includes: a display configured to display a first ultrasound image showing a surface of a 3D region of an object; a user input device configured to receive a user input for setting an ROI in the displayed first ultrasound image; and a controller configured to control the display to display a second ultrasound image showing an internal structure corresponding to the set ROI from among internal structures of the 3D region.

The controller may generate an ultrasound image representing the second volume in a more emphasized manner than the first volume by setting opacity of the second volume to be higher than opacity of the first volume.

The controller may generate an ultrasound image representing the first and second volumes in such a manner as to distinguish them from each other by setting colors for the first and second volumes differently.

The controller may generate an ultrasound image representing the second volume in a more emphasized manner than the first volume by setting a degree of focus of the second volume to be higher than a degree of focus of the first volume.

The display may display an ultrasound image showing the plurality of volumes, the ultrasound diagnosis apparatus may further comprise a user input device configured to receive a user input for selecting the first volume from among the plurality of volumes, and the controller may generate the ultrasound image representing the first volume in a different way than the other volumes by rendering the first volume based on different 3D rendering properties than the other volumes.

The controller may segment the 3D volume into the plurality of volumes based on a gradient between points in the 3D volume.

The controller may segment the 3D volume into the plurality of volumes based on an entropy value of the 3D volume.

The internal structure corresponding to the ROI may include relative positions of structures that are located below the ROI from among structures constituting the 3D region.

The display may display the relative positions of the structures located below the ROI by showing contours of the structures located below the ROI at different depths.

The structures may include at least one of a skin, an organ, a blood vessel, a bone, and a cavum.

The controller may generate the second ultrasound image showing the internal structure based on a gradient of ultrasound echo signals between points in the 3D region.

The user input device may receive a user input for changing the ROI, and the controller may control the display to display, on the changed ROI, the second ultrasound image showing an internal structure corresponding to the changed ROI.

The user input device may receive a user input for setting a depth of an internal structure to be displayed on the ROI, and the display may display a portion of the internal structure corresponding to the ROI, which is located below the set depth, on the ROI.

The controller may control the display to display a portion of the internal structure located below the set depth by setting opacity values at points located above the set depth, from among points in the 3D region, to less than or equal to a reference value.

The user input device may receive a user input for setting a plurality of ROIs according to a depth of the 3D region, and the controller may control the display to display on an ROI the second ultrasound image showing the internal structure corresponding to the ROI by respectively setting different rendering parameters for the set ROIs.

The rendering parameters may include at least one of an opacity, a degree of focus, and a color.

BRIEF DESCRIPTION OF THE DRAWINGS

These and/or other aspects will become apparent and more readily appreciated from the following description of the embodiments, taken in conjunction with the accompanying drawings in which:

FIGS. 2A through 2C illustrate an example in which an ultrasound diagnosis apparatus generates an ultrasound image representing a surface of a 3D volume, according to an embodiment;

FIG. 3 is a flowchart of a method, performed by an ultrasound diagnosis apparatus, of generating an image showing an internal structure of an object based on a gradient in a depth direction of intensity of ultrasound echo signals received from adjacent points from among points in a 3D region of the object, according to an embodiment;

FIGS. 4A through 4D illustrate an example in which an ultrasound diagnosis apparatus generates an image showing an internal structure of an object based on a gradient in a depth direction of ultrasound echo signals received from adjacent points from among points in a 3D region of the object, according to an embodiment;

FIG. 5 is a flowchart of a method, performed by an ultrasound diagnosis apparatus, of displaying an internal structure of a 3D volume on an ROI according to an embodiment;

FIG. 9 illustrates an example in which an ultrasound diagnosis apparatus displays an internal structure of a 3D volume corresponding to an ROI set by a user, together with a surface of the 3D volume, according to another embodiment;

FIG. 10 is a flowchart of a method, performed by an ultrasound diagnosis apparatus, of displaying an image showing a 3D volume based on 3D rendering properties set according to a depth, according to an embodiment;

FIGS. 11B and 11D illustrate an example in which an ultrasound diagnosis apparatus receives a user input for setting opacity with respect to a depth, according to an embodiment;

FIG. 13 is a flowchart of a method, performed by an ultrasound diagnosis apparatus, of displaying a volume of a 3D volume, which is located below a depth set by a user, according to an embodiment;

FIGS. 14A and 14B illustrate an example in which an ultrasound diagnosis apparatus displays an internal structure of a 3D volume located below a depth set by a user, according to an embodiment;

FIGS. 19A through 19C illustrate an example in which an ultrasound diagnosis apparatus receives a user input for setting a degree of focus according to a depth, according to an embodiment;

FIGS. 20A through 20D illustrate an example in which an ultrasound diagnosis apparatus displays an ultrasound image showing a 3D volume based on a degree of focus with respect to a depth selected by a user, according to an embodiment;

FIG. 21 is a flowchart of a method, performed by an ultrasound diagnosis apparatus, of displaying an ultrasound image showing a 3D volume based on a shape of an ROI set with respect to a depth selected by a user, according to an embodiment;

FIG. 27 illustrates an example in which an ultrasound diagnosis apparatus segments a 3D volume of an object into a plurality of volumes based on intensity and a gradient of intensity for a voxel among voxels constituting the 3D volume, according to an embodiment;

FIG. 29 is a flowchart of a method, performed by an ultrasound diagnosis apparatus, of setting different 3D rendering properties according to a plurality of volumes based on a user input, according to an embodiment;

FIG. 30 illustrates an example in which an ultrasound diagnosis apparatus sets different 3D rendering properties according to a plurality of volumes based on a user input, according to an embodiment;

DETAILED DESCRIPTION

Figure 1:
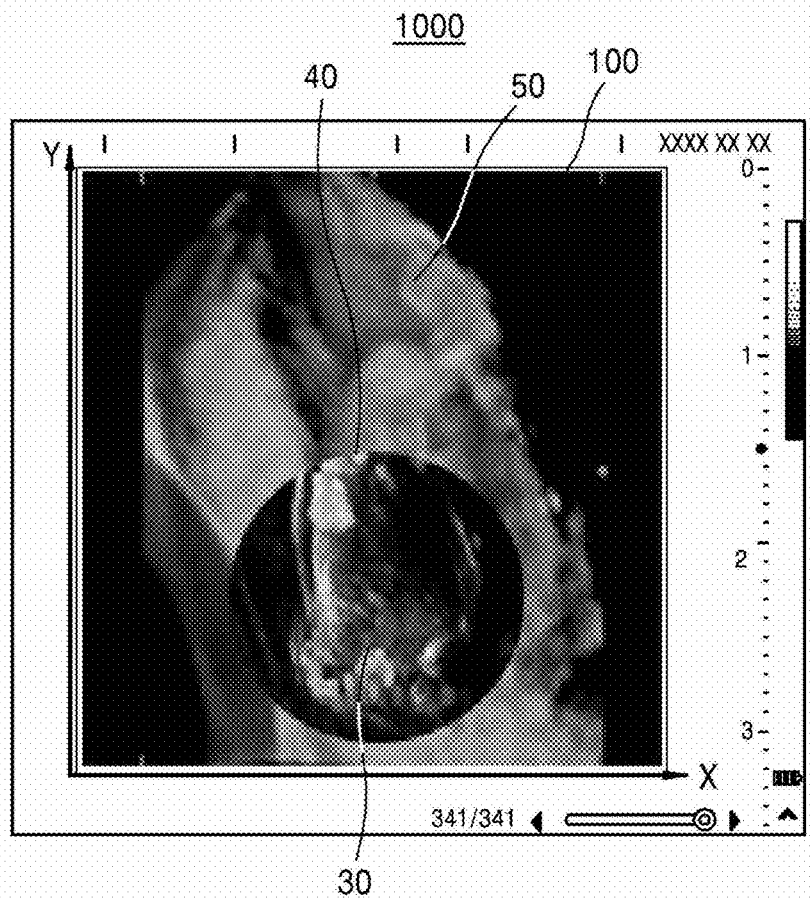
FIG. 1 illustrates an example in which an ultrasound diagnosis apparatus displays an internal structure of a three-dimensional (3D) volume corresponding to a region of interest (ROI), according to an embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the inventive concept.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. In addition, parts not related to the present inventive concept are omitted to clarify the description of embodiments. Expressions such as "at least one of," when preceding a list of elements, modify the entire list of elements and do not modify the individual elements of the list.

Throughout the specification, an "ultrasound image" refers to an image of an object, which is obtained using ultrasound waves. Furthermore, an "object" may be a human, an animal, or a part of a human or animal. For example, the object may be an organ such as the liver, the heart, the uterus, the brain, a breast, or the abdomen, a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Furthermore, throughout the specification, a three-dimensional (3D) volume" may be a 3D region of an imaged object. For example, if an ultrasound diagnosis apparatus 1000) captures an image of the heart, a 3D volume may be a 3D region of the imaged heart.

Furthermore, throughout the specification, "3D volume data" may be data used to represent a 3D volume of an object. For example, 3D volume data may be an ultrasound echo signal received from a 3D volume of an object.

Hereinafter, embodiments will be described in detail with reference to the accompanying drawings.

FIG. 1 illustrates an example in which an ultrasound diagnosis apparatus 1000 displays an internal structure of a 3D volume corresponding to a region of interest (ROI), according to an embodiment.

Referring to FIG. 1, the ultrasound diagnosis apparatus 1000 may display an internal anatomical structure 30 of a 3D volume corresponding to an ROI 40 on an ultrasound image 100

The ultrasound image 100 may be an ultrasound image showing a 3D volume as a 3D scene. For example, by capturing an image of a pregnant woman's abdomen via a probe including two-dimensional (2D) matrix array transducers, the ultrasound diagnosis apparatus 1000 may receive ultrasound echo signals reflected from a 3D region of a fetus. The ultrasound diagnosis apparatus 1000 may generate 3D volume data with respect to the fetus based on the received ultrasound echo signals. 3D volume data may be generated by mapping a 3D region of an object to a plurality of voxels having 3D position values and determining ultrasound echo signals received from points in the 3D region respectively corresponding to the voxels as being values of the voxels.

After generating the 3D volume data, the ultrasound diagnosis apparatus 1000 may determine an opacity value for each voxel in the 3D volume data. The ultrasound diagnosis apparatus 1000 may display the ultrasound image 100 showing the fetus as a 3D scene by performing volume rendering with respect to the 3D volume data based on an opacity value assigned to each voxel.

In this case, the ultrasound diagnosis apparatus 1000 may display an ultrasound image showing a surface of a 3D volume as a 3D scene. For example, the ultrasound diagnosis apparatus 1000 may determine an opacity value for each voxel to be proportional to an intensity of an ultrasound echo signal received from the fetus and display an ultrasound image showing a surface of a 3D volume as a 3D scene based on the determined opacity value and a volume rendering algorithm such as ray-casting. A method of generating an ultrasound image showing a surface of a 3D volume will be described in detail below with reference to FIGS. 2A through 2C.

Furthermore, the ultrasound diagnosis apparatus 1000 may display an ultrasound image showing an internal structure of a 3D volume as a 3D scene. For example, the ultrasound diagnosis apparatus 1000 may determine an opacity value for each voxel based on a gradient of intensity of ultrasound echo signals between the voxel and its adjacent voxel and generate an ultrasound image based on an opacity value assigned to each voxel and a ray casting algorithm. According to an embodiment, an ultrasound image showing an internal structure of a 3D volume may be referred to as a "Crystal Vue image". A method of generating an ultrasound image showing an internal structure of a 3D volume will be described in detail below with reference to FIG. 3 and FIGS. 4A through 4D.

An internal structure of a 3D volume may mean relative positions of structures constituting a 3D region of an object, and the relative positions may include relative positions in a 2D plane as well as relative positions in a depth direction. The structures in the 3D region of the object may include at least one of a part, organ, and tissue, but are not limited thereto.

For example, if an ultrasound image shows a surface of a 3D volume of a fetal face, the ultrasound image may represent only relative positions in a 2D plane of parts such as eyes, a noise, and a mouth. On the other hand, if an ultrasound image shows an internal structure of a 3D volume of a fetal face, the ultrasound image may represent relative positions in a depth direction of parts such as a skull, a brain, and a cerebral ventricle as well as a contour of the fetal face.

According to an embodiment, a part, an organ, or tissue may be referred to as a context, and the context may include, but is not limited to, a face, a spine, a ventricle, an umbilical cord, the liver, the heart, and a long bone.

Furthermore, according to an embodiment, the ultrasound diagnosis apparatus 1000 may perform 3D rendering based on not only a ray casting algorithm but also various other 3D rendering algorithms such as Marching Cubes, oriented splats, etc.

Furthermore, the ultrasound diagnosis apparatus 1000 may display the internal structure 30 of the 3D volume only on the ROI 40 from among regions in the ultrasound image 100 while displaying the ultrasound image 100 showing a surface 50 of the 3D volume on regions other than the ROI 40.

For example, if a user input for setting the ROI 40 in the ultrasound image 100 showing the surface 50 of the 3D volume, i.e., a skin of a fetal torso, the ultrasound diagnosis apparatus 1000 may display on the set ROI 40 the internal structure 30 of the fetal torso located below the ROI 40.

If an internal area of the fetal torso is composed of a spine and muscle tissue surrounding the spine, the ultrasound diagnosis apparatus 1000 may display the spine located below the ROI 40 on the ROI 40, together with a contour of the muscle tissue surrounding the spine.

Figure 2A:
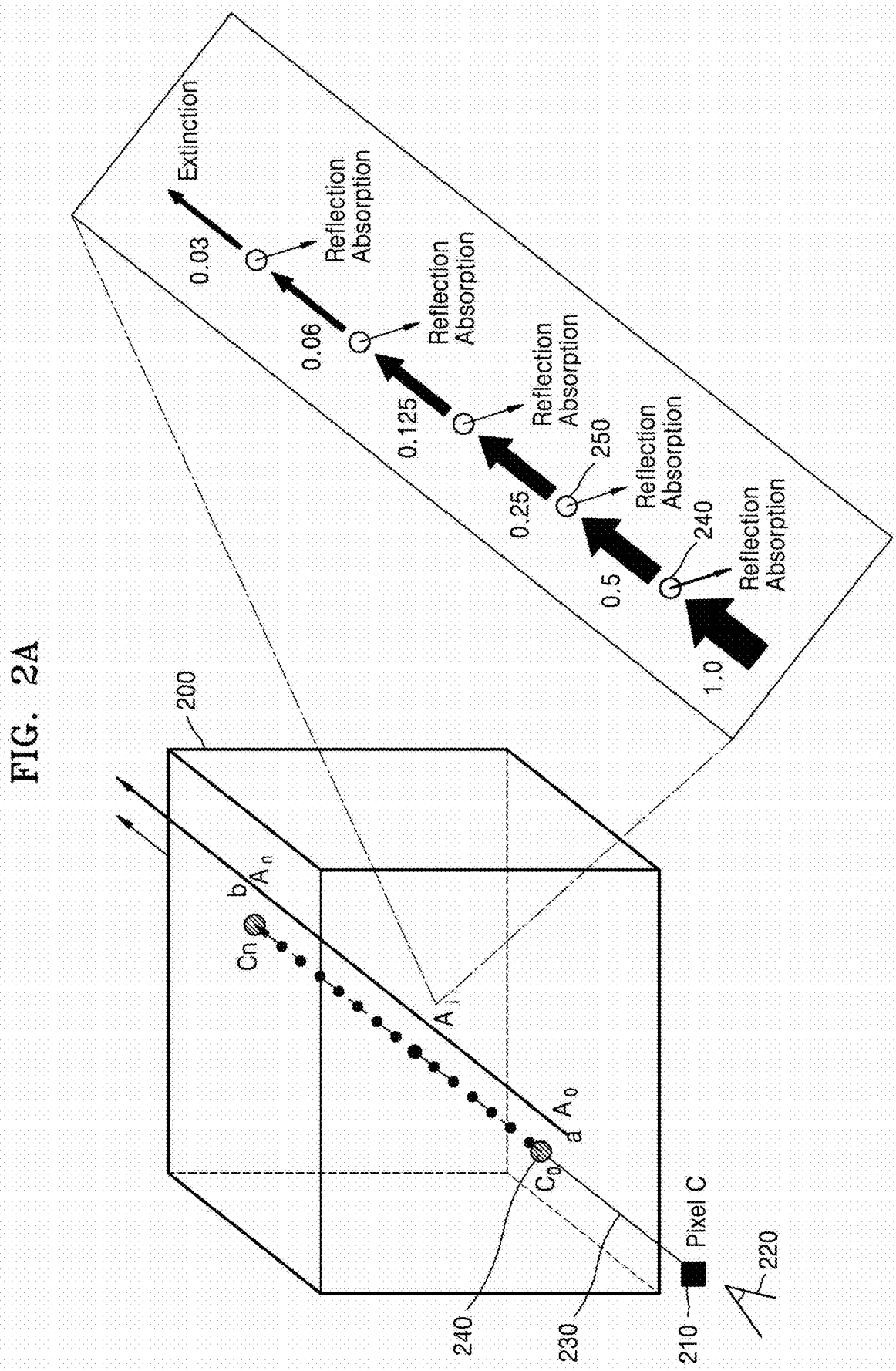

FIGS. 2A through 2C illustrate an example in which the ultrasound diagnosis apparatus 1000 generates an ultrasound image representing a surface of a 3D volume, according to an embodiment.

Referring to FIG. 2A, the ultrasound diagnosis apparatus 1000 may generate an ultrasound image showing a surface of a 3D volume based on a ray casting algorithm.

A 3D volume may be represented by using 3D volume data 200 that is a cubic box. For example, the 3D volume data 200 may be composed of a plurality of voxels having 3D coordinate values, and a value of each voxel may be an intensity of an ultrasound echo signal received from a point of an object corresponding to each voxel.

The ultrasound diagnosis apparatus 1000 may render the 3D volume data 200 as an ultrasound image. For example, as shown in FIG. 2A, the ultrasound diagnosis apparatus 1000 may render the 3D volume data as an ultrasound image by using a ray casting algorithm.

In detail, the ultrasound diagnosis apparatus 1000 may determine a beam 230 that is emitted from a light source 220 and propagates through a pixel C 210 in the ultrasound image toward the 3D volume data 200. A position of the light source 220 may be the same as a position of a user's eyes that view an image or be selected by the user.

The ultrasound diagnosis apparatus 1000 may sample intensities at a plurality of points $C_0$ through $C_n$ in the 3D volume data 200 along the determined beam 230. The points $C_0$ through $C_n$ may be voxels and may include points generated by interpolating voxels through which the beam 230 passes.

The ultrasound diagnosis apparatus 1000 may determine colors and opacity values at the respective points $C_0$ through $C_n$ based on intensities at the corresponding points $C_0$ through $C_n$. For example, as intensity at a point becomes higher, the ultrasound diagnosis apparatus 1000 may determine a higher opacity value at the point.

For example, as shown in FIG. 2A, if a beam having an amount of 1 emanates from the light source 220 along a beam's path, the ultrasound diagnosis apparatus 1000 may determine that an amount of 0.5 is reflected or absorbed and the remaining amount of 0.5 is transmitted at point $C_0$ 240 based on intensity at the point $C_0$ 240. Furthermore, when the transmitted amount of 0.5 propagates again to point $C_1$ 250, the ultrasound diagnosis apparatus 1000 may determine that an amount of 0.25 is reflected or absorbed and the remaining amount of 0.25 is transmitted at point $C_1$ 250 based on intensity at the point $C_1$ 250. Thus, the ultrasound diagnosis apparatus 1000 may determine opacity values at the point $C_0$ 240 and the point $C_1$ 250 to be 0.5 and 0.25, respectively.

After determining opacity values for the points $C_0$ through $C_n$, the ultrasound diagnosis apparatus 1000 may determine a color in the pixel C 210 constituting the ultrasound image by performing composition on opacity values and colors respectively corresponding to the points $C_0$ through $C_n$ along the beam 230.

By uniformly accumulating colors and opacity values across all the points $C_0$ through $C_n$ along the beam's path in a manner as shown in FIG. 2A, the ultrasound image may represent only a surface of the 3D volume. Since the ultrasound image shows only the surface of the 3D volume, the user is not able to see an internal structure of the 3D volume.

For example, referring to FIG. 2B, if a 3D volume is composed of a sun 262, an earth 264, and a moon 266 positioned in the same line as a user's eyes, an ultrasound image 100 generated by rendering 3D volume data may show only a surface of the sun 262. Thus, the user is not able to view the earth 264 and the moon 266 that are internal structures of the 3D volume.

Furthermore, for example, referring to FIG. 2C, if a 3D volume is a 3D region of a fetus 280 in the uterus, an ultrasound image 100 generated by rendering 3D volume data may show only a skin of the fetus 280. Thus, the user cannot identify positions of the heart, bones, and other organs of the fetus 280 that are internal structures of the 3D volume by examining the ultrasound image 100.

FIG. 3 is a flowchart of a method, performed by the ultrasound diagnosis apparatus 1000, of generating an image showing an internal structure of an object based on a gradient in a depth direction of intensity of ultrasound echo signals received from adjacent points from among points in a 3D region of the object, according to an embodiment.

The ultrasound diagnosis apparatus 1000 may acquire ultrasound echo signals with respect to a 3D region of an object (S310).

The 3D region of the object for which the ultrasound echo signals are acquired may be referred to as a 3D volume. The ultrasound diagnosis apparatus 1000 may generate 3D volume data with respect to the 3D volume based on the acquired ultrasound echo signals. The 3D volume data may be generated by mapping the 3D region of the object to a plurality of voxels having 3D position values and determining ultrasound echo signals received from points in the 3D region respectively corresponding to the voxels as being values of the voxels.

The ultrasound diagnosis apparatus 1000 may determine an opacity value of a point in the 3D region based on a gradient of intensity of an ultrasound echo signal between the point and its adjacent point (S320).

For example, after generating the 3D ultrasound volume data, the ultrasound diagnosis apparatus 1000 may determine an opacity value for each voxel in the 3D volume data. In detail, the ultrasound diagnosis apparatus 1000 may determine an opacity value for each voxel based on a gradient of intensity of ultrasound echo signals between the voxel and its adjacent voxel.

The ultrasound diagnosis apparatus 1000 may display an image showing an internal structure of the 3D region based on the determined opacity value (S330).

For example, the ultrasound diagnosis apparatus 1000 may generate an ultrasound image by applying a ray casting algorithm to the 3D volume data consisting of voxels for which opacity values are respectively determined.

FIGS. 4A through 4D illustrate an example in which the ultrasound diagnosis apparatus 1000 generates an image showing an internal structure of an object based on a gradient in a depth direction of ultrasound echo signals received from adjacent points from among points in a 3D region of the object, according to an embodiment.

Figure 4A:
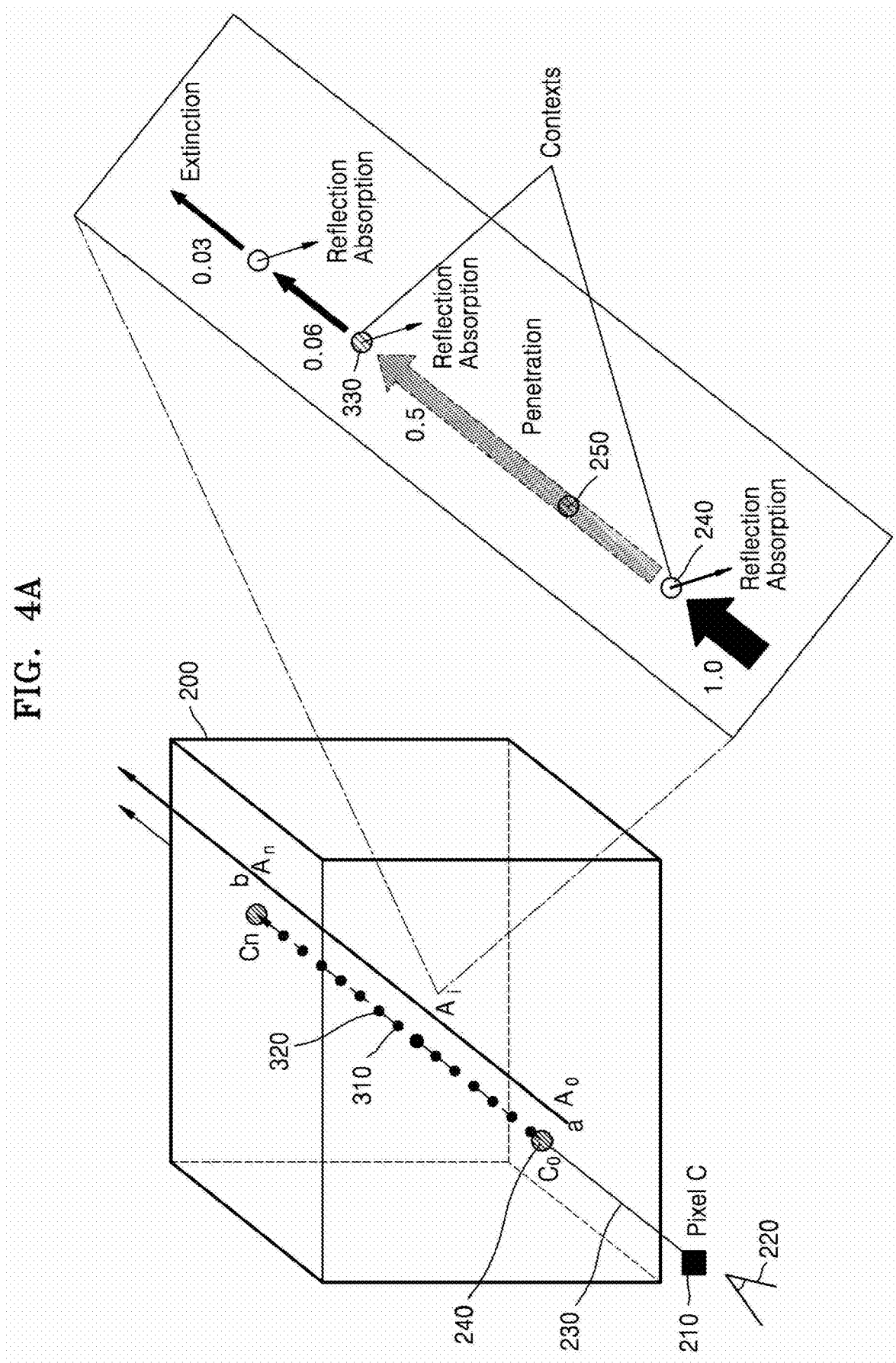

Referring to FIG. 4A, the ultrasound diagnosis apparatus 1000 may generate an ultrasound image showing an internal structure of a 3D volume based on a gradient in a depth direction of ultrasound echo signals received from adjacent points from among points in a 3D region.

A gradient between adjacent points may mean the degree of homogeneity between the adjacent points. For example, if a first point 310 is a cavum and a second point 320 adjacent to the first point 310 is a uterine tissue, since intensity at the first point 310 is almost close to "0" and intensity at the second point 320 has a significantly great value, a differential value of intensity between the first and second points 310 and 320 may have a large value. On the other hand, if the first point 310 is a skin tissue and the second point 320 is another point in the same skin tissue, a differential value of intensity between the first and second points 310 and 320 may be almost close to "0". Thus, a point having a large differential value may be determined as being a contour of a part, organ, or tissue.

The ultrasound diagnosis apparatus 1000 may determine an opacity value at each point in a 3D volume based on a gradient of intensity between each point and a point that is adjacent to each point_in a direction in which a beam 230 travels. For example, the ultrasound diagnosis apparatus 1000 may determine an opacity value at the second point 320 to be proportional to a differential value of intensity between the first point 310 and the second point 320 adjacent thereto.

For example, as shown in FIG. 4A, if a beam having an amount of 1 emanates from a light source 220 along a beam's path, the ultrasound diagnosis apparatus 1000 may determine that an amount of 0.5 is reflected or absorbed at point C0 240 and the remaining amount of 0.5 is transmitted in proportion to a differential value at the point $C_0$ 240. Furthermore, when the penetrated amount of 0.5 propagates again to point $C_1$ 250, the ultrasound diagnosis apparatus 1000 may determine that the amount of 0.5 is penetrated without reflection or absorption at point $C_1$ 250 in proportion to a differential value at the point $C_1$ 250. Thus, the ultrasound diagnosis apparatus 1000 may determine opacity values at the point $C_0$ 240 and the point $C_1$ 250 to be 0.5 and 0, respectively.

After determining opacity values for a plurality of points $C_0$ through $C_n$, the ultrasound diagnosis apparatus 1000 may generate an ultrasound image of a 3D volume by applying a ray casting algorithm to 3D volume data for which opacity values are respectively determined. For example, the ultrasound diagnosis apparatus 1000 may determine a color in a pixel C 210 in the ultrasound image by performing composition on opacity values and colors respectively corresponding to the points $C_0$ through $C_n$ along the beam 230.

The ultrasound image generated based on a gradient between adjacent points may show an internal structure of the 3D volume. For example, if the point $C_0$ 240 is a point where a fetal skin starts and the point $C_1$ 250 is a point where a fetal stomach starts, the ultrasound diagnosis apparatus 1000 may display an ultrasound image showing a contour of the fetal skin and a contour of the fetal stomach located in the contour of the fetal skin.

Figure 4B:
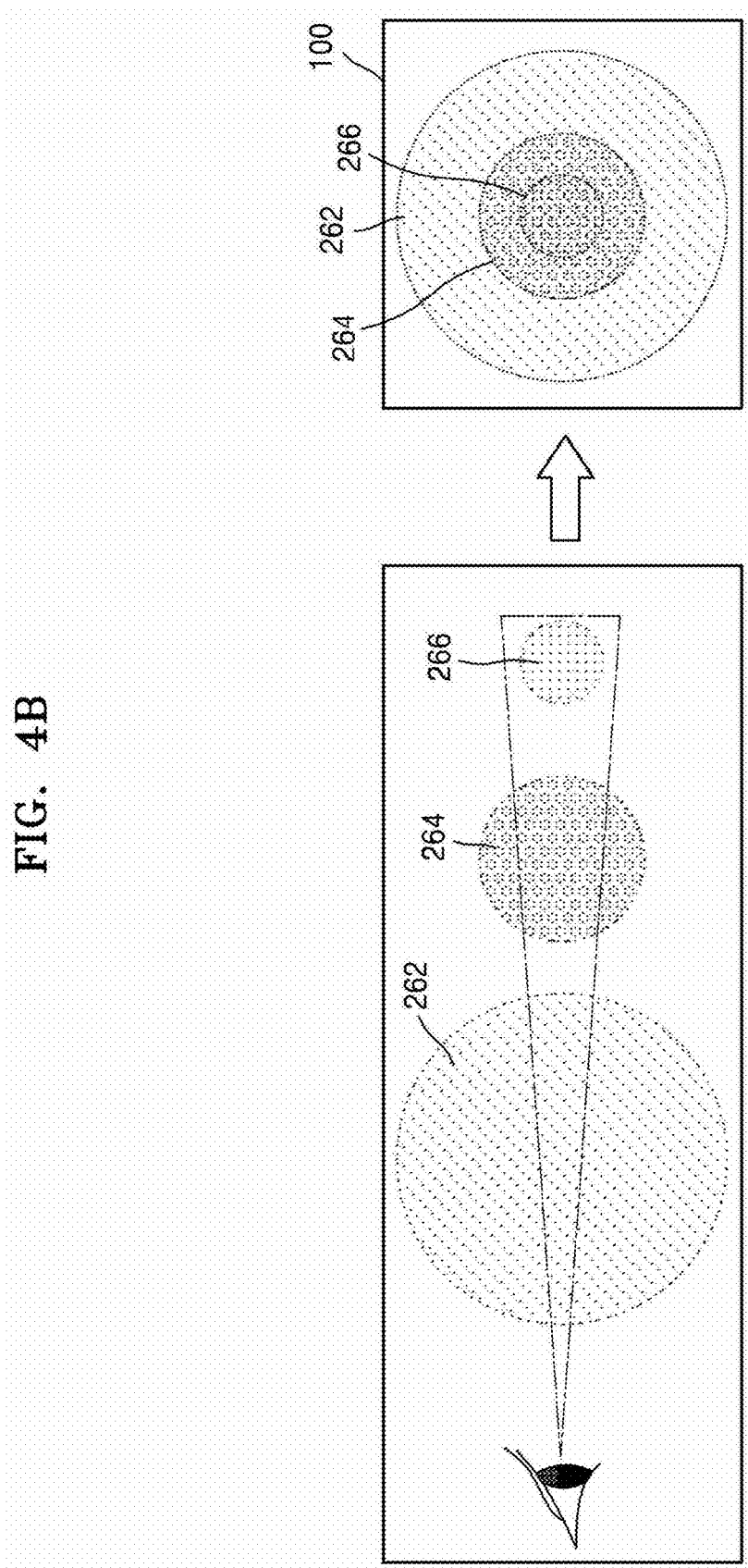

Referring to FIG. 4B, if a 3D volume is composed of a sun 262, an earth 264, and a moon 266 positioned in the same line as a user's eyes, an ultrasound image 100 generated by rendering 3D volume data may show contours of the moon 264 and the moon 266 as well as a contour of the sun 262.

Thus, by examining the ultrasound image 100, the user is able to identify positions of the earth 264 and the moon 266 that are internal structures of the 3D volume.

Figure 4C:
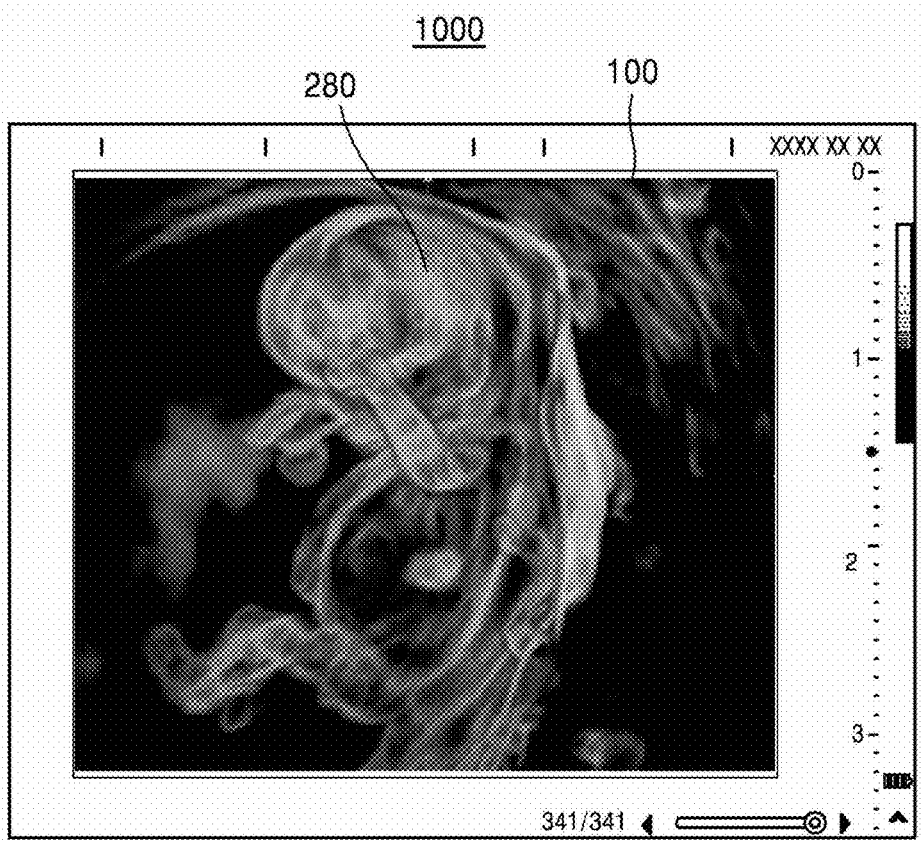

Referring to FIG. 4C, if a 3D volume is a fetus 280 in the uterus, an ultrasound image 100 generated by rendering the 3D volume may show contours of a brain and organs of the fetus 280 as well as a contour of a skin of the fetus 280. Thus, by examining the ultrasound image 100, the user may identify positions of a heart, bones, and other organs of the fetus 280 that are internal structures of the 3D volume.

As shown in FIG. 4C, the ultrasound diagnosis apparatus 1000 may show only a contour of an internal part of 3D volume, organ, or tissue while displaying the interior of the part, organ, or tissue as being transparent.

Furthermore, referring to FIG. 4D, the ultrasound diagnosis apparatus 1000 may determine an opacity value for each point based on intensity at each point as well as a calculated gradient. For example, if a gradient between a point and its adjacent point is less than or equal to a first threshold value but intensity at the point is greater than or equal to a second threshold value, the ultrasound diagnosis apparatus 1000 may determine an opacity value for the point to be a high value.

As shown in FIG. 4D, the ultrasound diagnosis apparatus 1000 may generate an ultrasound image 410 showing a surface of a fetus's legs and an ultrasound image 420 showing internal structures of the fetus's legs. The ultrasound image 420 may show internal structures of the fetus's legs in more detail by representing muscles of the legs as being semi-transparent and bones as being opaque.

Furthermore, according to an embodiment, the ultrasound diagnosis apparatus 1000 may show only a part, organ, or tissue selected by a user from among internal structures of a 3D volume as an ultrasound image.

FIG. 5 is a flowchart of a method, performed by the ultrasound diagnosis apparatus 1000, of displaying an internal structure of a 3D volume on an ROI according to an embodiment.

Referring to FIG. 5, the ultrasound diagnosis apparatus 1000 may display a first image showing a surface of a 3D region of an object (S510).

The ultrasound diagnosis apparatus 1000 may generate 3D volume data with respect to the 3D region of the object based on ultrasound echo signals received from the 3D region of the object.

After generating the 3D volume data, the ultrasound diagnosis apparatus 1000 may determine an opacity value for each voxel in the 3D volume data. For example, the ultrasound diagnosis apparatus 1000 may determine an opacity value for each voxel to be proportional to an intensity of an ultrasound echo signal received from a fetus. The ultrasound diagnosis apparatus 1000 may display a first ultrasound image showing a surface of a 3D volume as a 3D scene by applying a ray casting algorithm to the 3D volume data consisting of voxels for which opacity values are respectively determined.

The ultrasound diagnosis apparatus 1000 may receive a user input for setting an ROI in the displayed ultrasound image (S520).

The ultrasound diagnosis apparatus 1000 may display on the set ROI a second ultrasound image showing an internal structure corresponding to the ROI from among internal structures of the 3D region (S530).

The internal structure corresponding to the ROI may include relative positions in a depth direction of structures that are located below the ROI from among structures constituting the 3D region. For example, by displaying contours of the structures located below the ROI at different depths, the ultrasound diagnosis apparatus 1000 may show relative positions in a depth direction of the structures located below the ROI. The structures may include at least one of a skin, an organ, a blood vessel, a bone, and a cavum, but are not limited thereto.

The ultrasound diagnosis apparatus 1000 may generate a second ultrasound image showing an internal structure based on a gradient in a depth direction of ultrasound echo signals received from adjacent points from among points in a 3D region. For example, the ultrasound diagnosis apparatus 1000 may determine an opacity value for each voxel based on a gradient of intensity of ultrasound echo signals between the voxel and its adjacent voxel and generate a second ultrasound image by applying a ray casting algorithm to a 3D volume.

Furthermore, when a user input for changing an ROI is received, the ultrasound diagnosis apparatus 1000 may display a second ultrasound image showing an internal structure corresponding to the changed ROI on the changed ROI.

Furthermore, when a user input for setting a depth of an internal structure to be displayed on an ROI is received, the ultrasound diagnosis apparatus 1000 may display a portion of the internal structure corresponding to the ROI, which is located below the set depth, on the ROI. For example, the ultrasound diagnosis apparatus 1000 may display a portion of the internal structure located below the set depth by setting opacity values at points located above the set depth, from among points in a 3D region, to "0".

Furthermore, when a first ultrasound image shows a surface of the 3D region and at least one structure located below the surface of the 3D region, as a user input for selecting one from among the at least one structure, the ultrasound diagnosis apparatus 1000 may display a second ultrasound image showing the selected structure on an ROI.

Furthermore, when a user input for setting a plurality of ROIs is received, the ultrasound diagnosis apparatus 1000 may display, on an ROI, a second ultrasound image showing an internal structure corresponding to the ROI by respectively setting different rendering parameters for the set ROIs according to a depth of the 3D region. In this case, the rendering parameters may include at least one of opacity, degree of focus, and color, but are not limited thereto.

Figure 6:
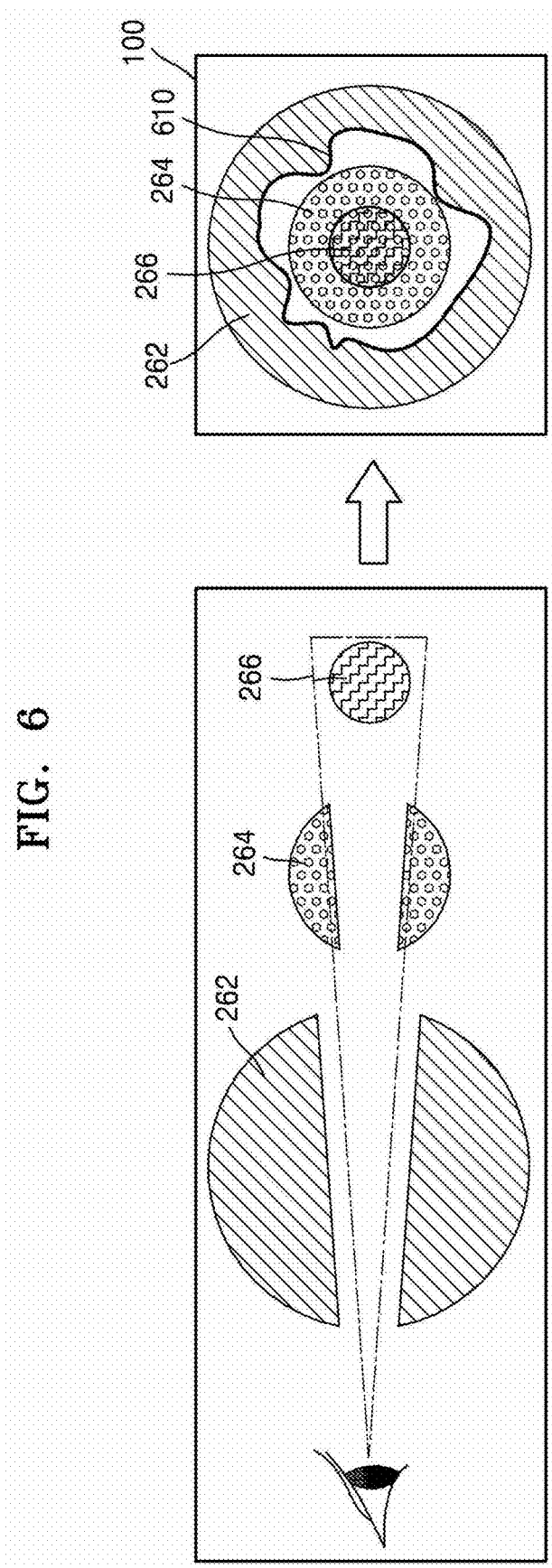
FIG. 6 illustrates a method, performed by an ultrasound diagnosis apparatus, of displaying an internal structure of a 3D volume on an ROI according to an embodiment.

FIG. 6 illustrates a method, performed by the ultrasound diagnosis apparatus 1000, of displaying an internal structure of a 3D volume on an ROI according to an embodiment.

Referring to FIG. 6, the ultrasound diagnosis apparatus 1000 may display an internal structure of a 3D volume only on an ROI 610 while displaying a surface of a 3D volume on a region other than the ROI 610.

If the 3D volume is composed of a sun 262, an earth 264, and a moon 266 positioned in the same line as a user's eyes, the ultrasound diagnosis apparatus 1000 may display an ultrasound image showing a surface of the sun 262 that is a surface of the 3D volume.

The ultrasound diagnosis apparatus 1000 may receive a user input for setting the ROI 610 in the ultrasound image. The ultrasound diagnosis apparatus 1000 may generate an image showing an internal structure of a 3D volume corresponding to the set ROI 610 and display the generated image on the ROI 610. Referring to FIG. 6, the earth 264 and the moon 266 may be located in the set ROI 610 in a depth direction. In this case, the ultrasound diagnosis apparatus 1000 may generate an image showing the earth 264 and the moon 266 and display the generated image on the ROI 610.

Thus, the user is able to observe the surface of the 3D volume together with the internal structure of the 3D volume corresponding to the ROI 610.

Figure 7A:
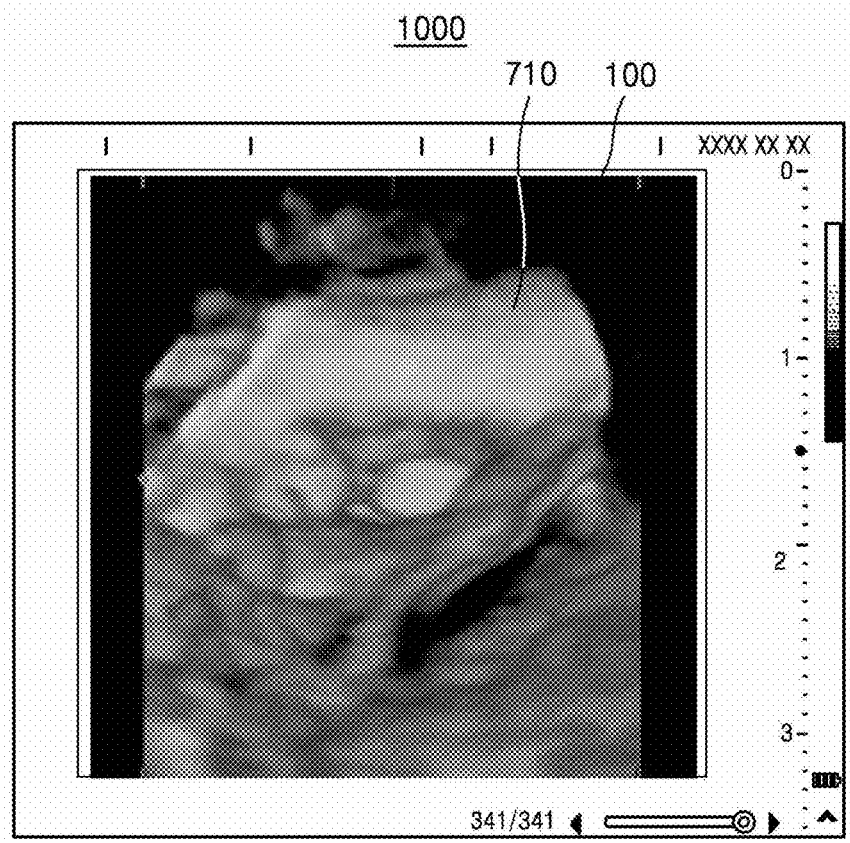
FIGS. 7A and 7B illustrate an example in which an ultrasound diagnosis apparatus displays an internal structure of a 3D volume corresponding to an ROI set by a user, together with a surface of the 3D volume, according to an embodiment.
Figure 7B:
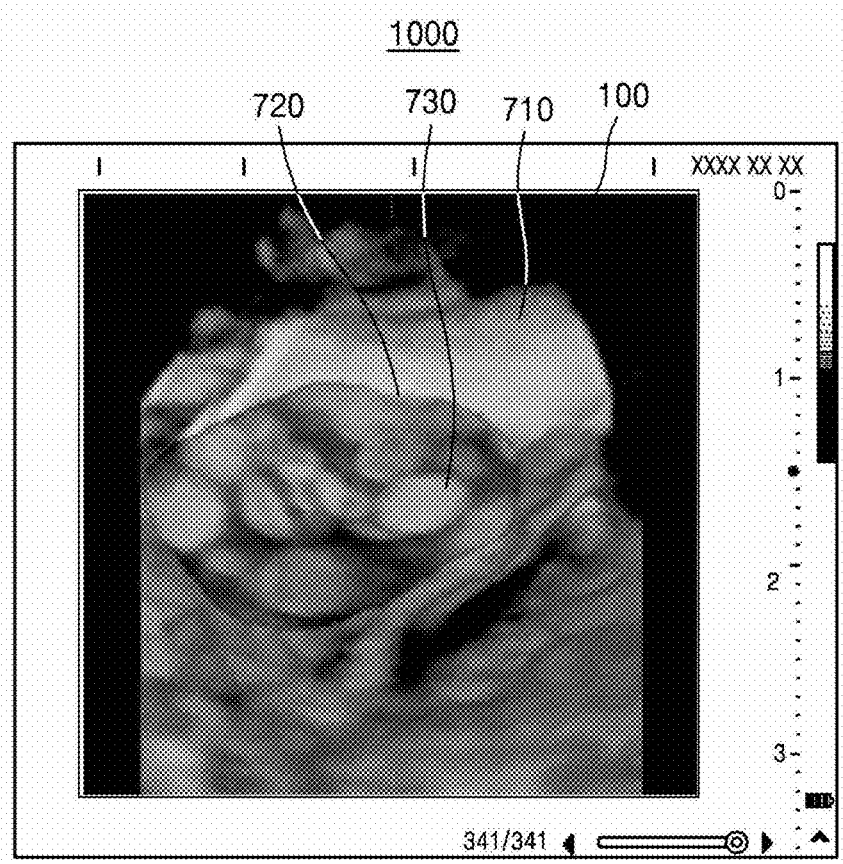

FIGS. 7A and 7B illustrate an example in which the ultrasound diagnosis apparatus 1000 displays an internal structure of a 3D volume corresponding to an ROI set by a user, together with a surface of the 3D volume, according to an embodiment.

Referring to FIG. 7A, the ultrasound diagnosis apparatus 1000 may display an ultrasound image 100 showing a surface 710 of an ovary.

As shown in FIG. 7A, ovarian follicles may hardly be identified in the ultrasound image showing the surface of the ovary 710.

Referring to FIG. 7B, the ultrasound diagnosis apparatus 1000 may determine an ROI and display follicles located below the surface 710 of the ovary on the determined ROI. For example, the ultrasound diagnosis apparatus 1000 may automatically determine a position of a follicle in a 3D volume of the ovary. For example, the ultrasound diagnosis apparatus 1000 may automatically determine a position of a follicle in the ovary based on at least one of intensity of an ultrasound echo signal received from the follicle, a gradient of intensity between a surface of the follicle and tissue in the ovary adjacent to the surface of the follicle, and a position of the ovary.

The ultrasound diagnosis apparatus 1000 may determine, based on the determined position of the follicle, a region where the follicle is located as an ROI 720. The ultrasound diagnosis apparatus 1000 may display a follicle 730 located below the ROI 720 on the determined ROI 720.

In this case, the ultrasound diagnosis apparatus 1000 may display follicles located immediately beneath the ROI 720 as well as those located at the back in a depth direction by representing contours of follicles located below the ROI 720 and the interior of each follicle as being transparent.

Figure 8A:
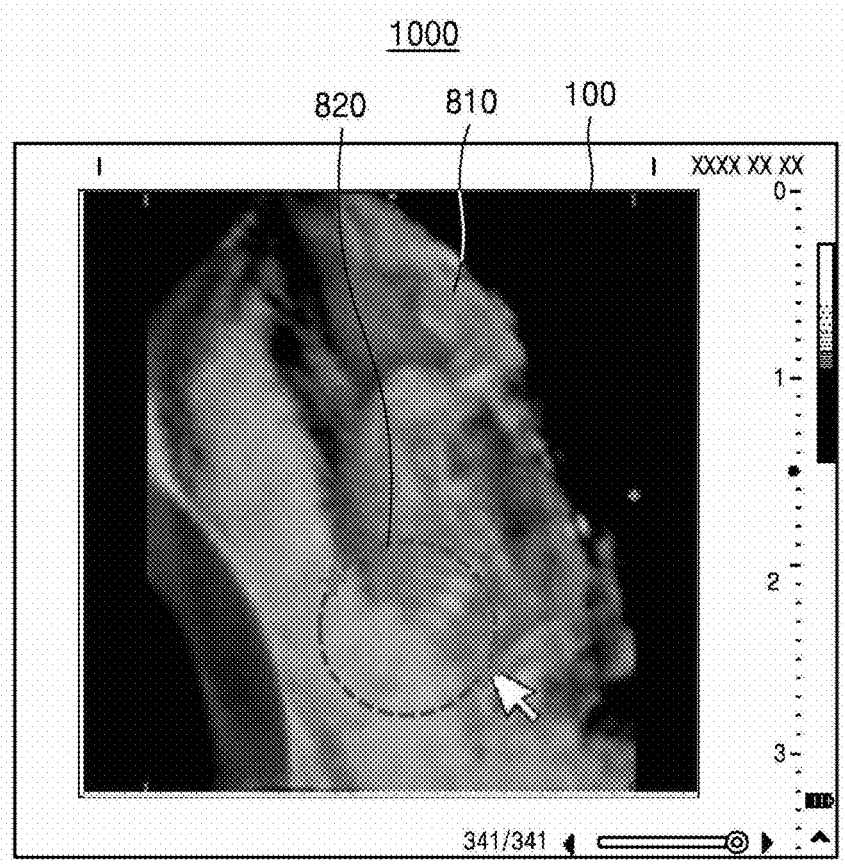
FIGS. 8A through 8C illustrate an example in which an ultrasound diagnosis apparatus displays an internal structure of a 3D volume corresponding to an ROI set by a user, together with a surface of the 3D volume, according to another embodiment.
Figure 8B:
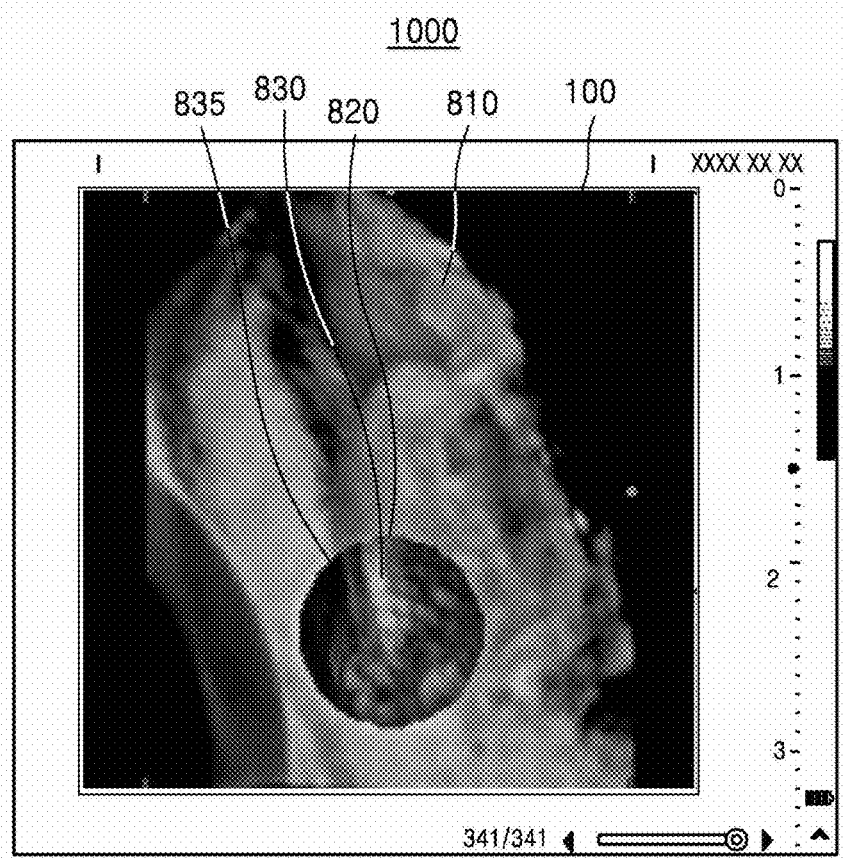
Figure 8C:
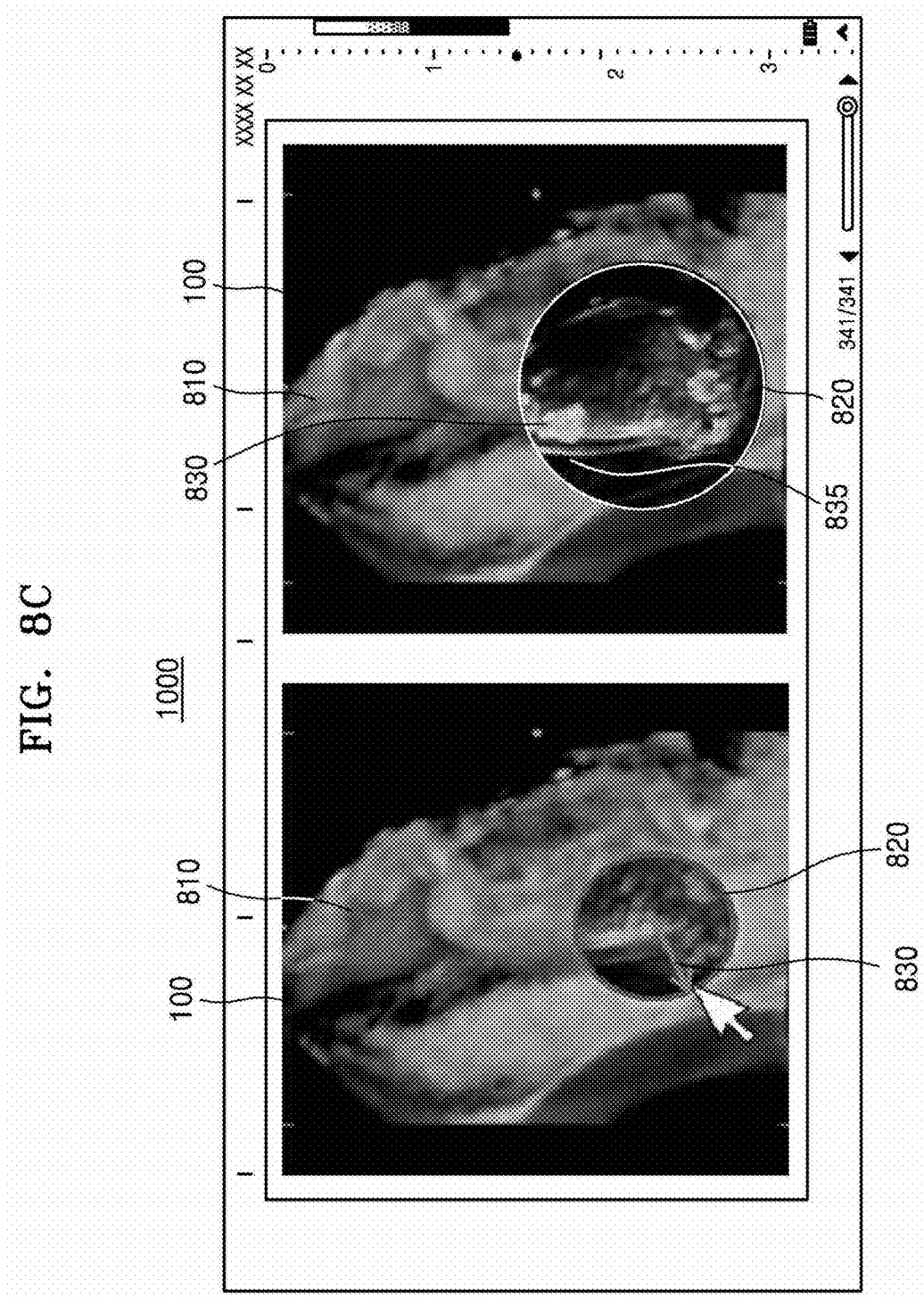

FIGS. 8A through 8C illustrate an example in which the ultrasound diagnosis apparatus 1000 displays an internal structure of a 3D volume corresponding to an ROI set by a user, together with a surface of the 3D volume, according to an embodiment.

Referring to FIG. 8A, the ultrasound diagnosis apparatus 1000 may receive a user input for setting an ROI 820 in an ultrasound image 100 showing a surface of a 3D volume including a fetus's spine.

The ultrasound image 100 may be obtained by scanning a fetus' side and show a skin of a flank thereof.

The ultrasound diagnosis apparatus 1000 may provide a user interface configured to select a shape of the ROI 820 and set a position of the ROI 820 in the ultrasound image 100. Examples of the shape of the ROI 820 may include a circle, a triangle, a quadrangle, etc., but are not limited thereto.

Referring to FIG. 8B, the ultrasound diagnosis apparatus 1000 may display an internal structure of a 3D volume corresponding to the ROI 820 on the ROI 820.

For example, the ultrasound diagnosis apparatus 1000 may display a vertebra 830 located below the ROI 820 and a contour 835 of tissue surrounding a spine, which allows the user to identify abnormality of the fetus such as spina bifida.

Referring to FIG. 8C, the ultrasound diagnosis apparatus 1000 may receive a user input for adjusting a size of the ROI 820. For example, as shown in FIG. 8C, the ultrasound diagnosis apparatus 1000 may receive a user input for increasing a size of the ROI 820 whose shape is set to a circle.

After the size of the ROI 820 has been adjusted, the ultrasound diagnosis apparatus 1000 may display an internal structure of a 3D volume corresponding to the adjusted size of the ROI 820. For example, the ultrasound diagnosis apparatus 1000 may display the vertebra 830 located below the adjusted ROI 820 and a contour of tissue surrounding the spine.

FIG. 9 illustrates an example in which the ultrasound diagnosis apparatus 1000 displays an internal structure of a 3D volume corresponding to an ROI set by a user, together with a surface of the 3D volume, according to another embodiment.

Referring to FIG. 9, the ultrasound diagnosis apparatus 1000 may receive a user input for setting an ROI 910 in an ultrasound image showing a fetus's back.

For example, the user input for setting the ROI 910 may be a user input for drawing a contour of the ROI 910.

After the ROI 910 has been set, the ultrasound diagnosis apparatus 1000 may display an internal structure of a 3D volume corresponding to the set ROI 910.

For example, the ultrasound diagnosis apparatus 1000 may display a vertebra 920, ribs 922, and an organ 924 located below the set ROI 910.

FIG. 10 is a flowchart of a method, performed by the ultrasound diagnosis apparatus 1000, of displaying an image showing a 3D volume based on 3D rendering properties set according to a depth, according to an embodiment.

The ultrasound diagnosis apparatus 1000 may display a first ultrasound image showing an object (S1010).

Examples of the first ultrasound image may include an A mode image, a B mode image, an M mode image, a Doppler image, and a Crystal Vue image, but are not limited thereto.

Furthermore, the ultrasound diagnosis apparatus 1000 may display a plurality of ultrasound images respectively showing different cross-sections of an object and determine a first ultrasound image by receiving a user input for selecting one of the plurality of ultrasound images as the first ultrasound image.

The ultrasound diagnosis apparatus 1000 may receive a user input for selecting first and second depths in a first ultrasound image and setting different 3D rendering properties with respect to the first and second depths (S1020).

The 3D rendering properties may include at least one of an opacity, a color, a size and shape of an ROI, and a degree of focus. Furthermore, the first and second depths may respectively be first and second depth intervals in a 3D volume.

The ultrasound diagnosis apparatus 1000 may provide a user interface for setting 3D rendering properties. The user interface for setting the 3D rendering properties may include an indicator that indicates a direction of a depth in the first ultrasound image. Furthermore, the user interface for setting the 3D rendering properties may include a plurality of images representing a pattern of the 3D rendering properties according to a depth. The ultrasound diagnosis apparatus 1000 may receive a user input for setting 3D rendering properties according to a depth by receiving a user input for selecting one of a plurality of images respectively representing patterns of the 3D rendering properties according to depths.

The ultrasound diagnosis apparatus 1000 may generate a second ultrasound image showing a 3D volume of the object based on the set 3D rendering properties (S1030).

The ultrasound diagnosis apparatus 1000 may display the generated second ultrasound image (S1040).

Figure 11A:
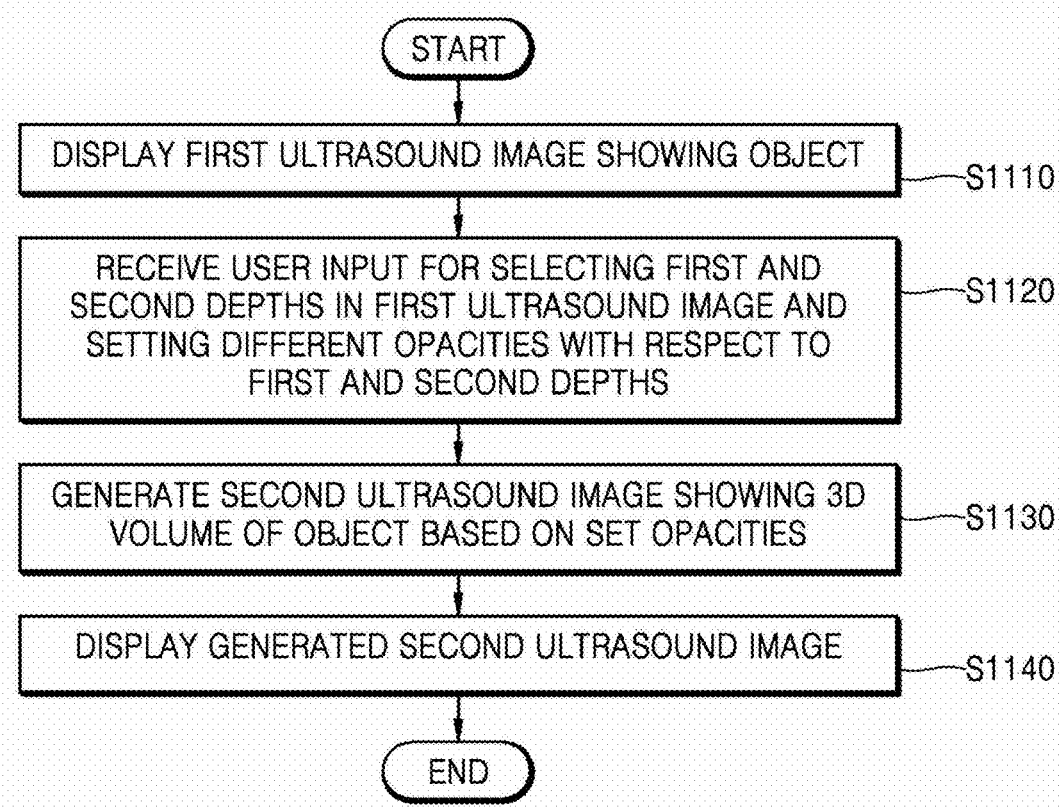
FIG. 11A is a flowchart of a method, performed by an ultrasound diagnosis apparatus, of displaying an image showing a 3D volume based on opacity according to a depth, according to an embodiment.

FIG. 11A is a flowchart of a method, performed by the ultrasound diagnosis apparatus 1000, of displaying an image showing a 3D volume based on opacity according to a depth, according to an embodiment.

The ultrasound diagnosis apparatus 1000 may display a first ultrasound image showing an object (S1110).

The ultrasound diagnosis apparatus 1000 may receive a user input for selecting first and second depths in the first ultrasound image and setting different opacity values with respect to the first and second depths (S1120).

For example, the ultrasound diagnosis apparatus 1000 may display a user interface for setting an opacity value by using a graph and may receive a user input for setting an opacity value with respect to a depth via the user interface.

Furthermore, for example, the ultrasound diagnosis apparatus 1000 may receive a user input for setting a first opacity value with respect to the first to second depths and a second opacity value with respect to the second to third depths.

According to an embodiment, the ultrasound diagnosis apparatus 1000 may segment a part, organ, or tissue in an ultrasound image into regions to be displayed, select one from among regions of the segmented part, organ, or tissue, and receive a user input for selecting an opacity value with respect to a depth by receiving a user input for selecting an opacity value corresponding to the selected region of the part, organ, or tissue.

The ultrasound diagnosis apparatus 1000 may generate a second ultrasound image showing a 3D volume of the object based on the set opacity values (S1130). The ultrasound diagnosis apparatus 1000 may display an image showing a 3D volume by taking into account an opacity value set according to a depth as well as intensity of an ultrasound echo signal. For example, the ultrasound diagnosis apparatus 1000 may determine again an opacity value for a voxel so as to be proportional to intensity of the voxel and an opacity value set according to a depth of the voxel. If intensity of ultrasound from a first voxel has a high value but an opacity set according to a depth of the first voxel has a low value, the ultrasound diagnosis apparatus 1000 may determine an opacity value for the first voxel to be low.

Furthermore, the ultrasound diagnosis apparatus 1000 may display an image showing a 3D volume by taking into account an opacity value set according to a depth of a voxel as well as a gradient of intensity between the voxel and its adjacent voxel. For example, the ultrasound diagnosis apparatus 1000 may determine again an opacity value for a voxel so as to be proportional to a gradient of intensity of ultrasound between the voxel and its adjacent voxel and an opacity value set according to a depth of the voxel. If a gradient of intensity between a voxel and its adjacent voxel has a large value but opacity set according to a depth of the voxel has a low value, the ultrasound diagnosis apparatus 1000 may determine an opacity value for the voxel to be low.

The ultrasound diagnosis apparatus 1000 may display the generated second ultrasound image (S1140).

Figure 11C:
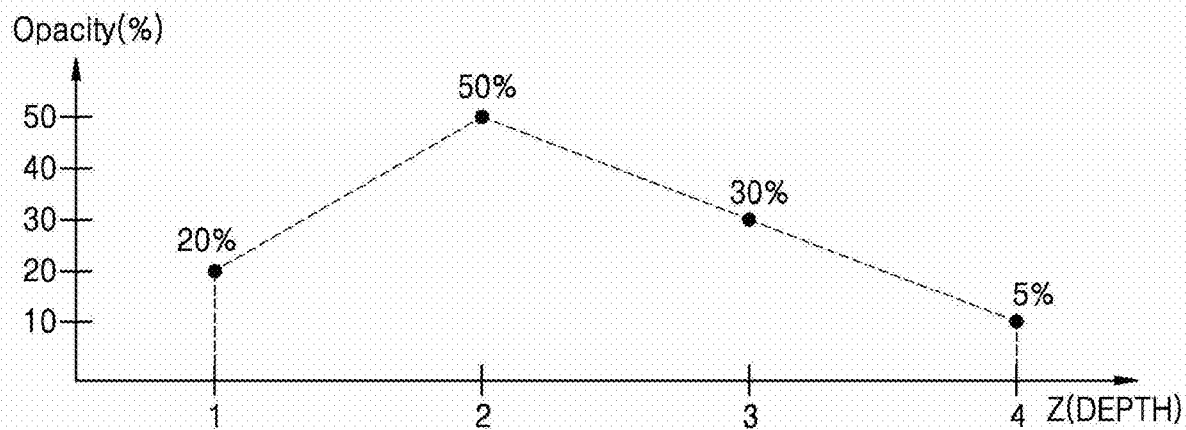
FIG. 11C illustrates an example in which opacity values with respect to a depth are set in an ultrasound diagnosis apparatus based on a user input, according to an embodiment.
Figure 11D:
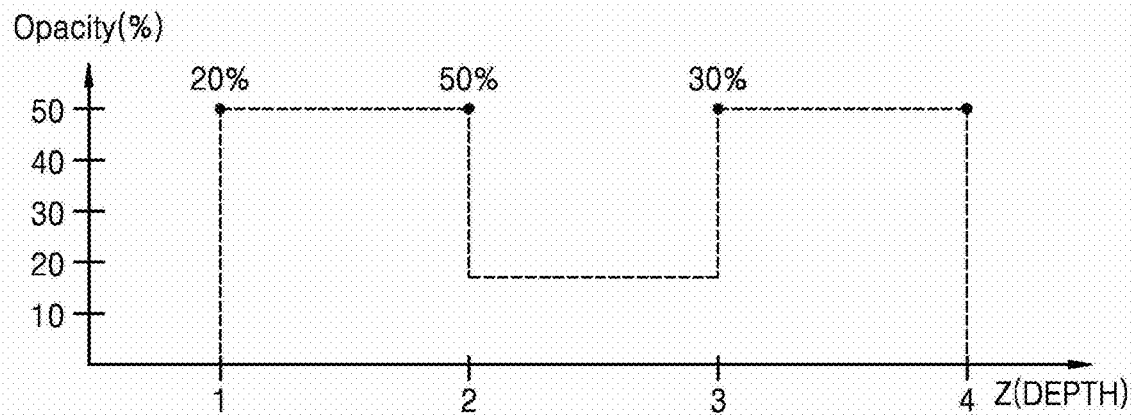

FIGS. 11B and 11D illustrate an example in which the ultrasound diagnosis apparatus 1000 receives a user input for setting opacity with respect to a depth, according to an embodiment.

Referring to FIG. 11B, the ultrasound diagnosis apparatus 1000 may display an ultrasound image 100 while displaying a user interface 1110 for setting opacity according to a depth on the ultrasound image 100.

Examples of the ultrasound image 100 may include an A mode image, a B mode image, an M mode image, a Doppler image, and a Crystal Vue image, but are not limited thereto.

For example, the user interface 1110 may be displayed on the ultrasound image 100 and include a coordinate axis (Z axis) representing a degree of a depth and a coordinate axis (Opacity axis) representing a range of opacity.

The user may set opacity for a part, which is located at a depth of interest among parts of the object in the ultrasound image 100, to a high value via the user interface 1110 displayed on the ultrasound image 100.

For example, if the ultrasound image 100 shows a first part 1130, a second part 1132 surrounding the first part 1130, a third part 1134 surrounding the second part 1132, and a fourth part 1136 surrounding the third part 1134, the user may set opacity at depth 2 to a higher value than those at the other depths in order to display in detail the third and fourth parts 1134 and 1136 at the depth 2.

Referring to FIG. 11C, opacity values with respect to a depth may be set in the ultrasound diagnosis apparatus 1000 based on the user input received as shown in FIG. 11B.

The ultrasound diagnosis apparatus 1000 may display an ultrasound image showing a 3D volume of the object based on the set opacity values. For example, the ultrasound image generated based on the set opacity values with respect to a depth described with reference to FIG. 11C may represent finer details of structures located at the depth 2 while hardly representing structures located at depth 4.

Referring to FIG. 11D, opacity values with respect to a depth interval may be set in the ultrasound diagnosis apparatus 1000.

An ultrasound image generated based on opacity values with respect to a depth interval shown in FIG. 11D may show finer details of structures located at depths 1 to 2 and depths 3 to 4.

Figure 12A:
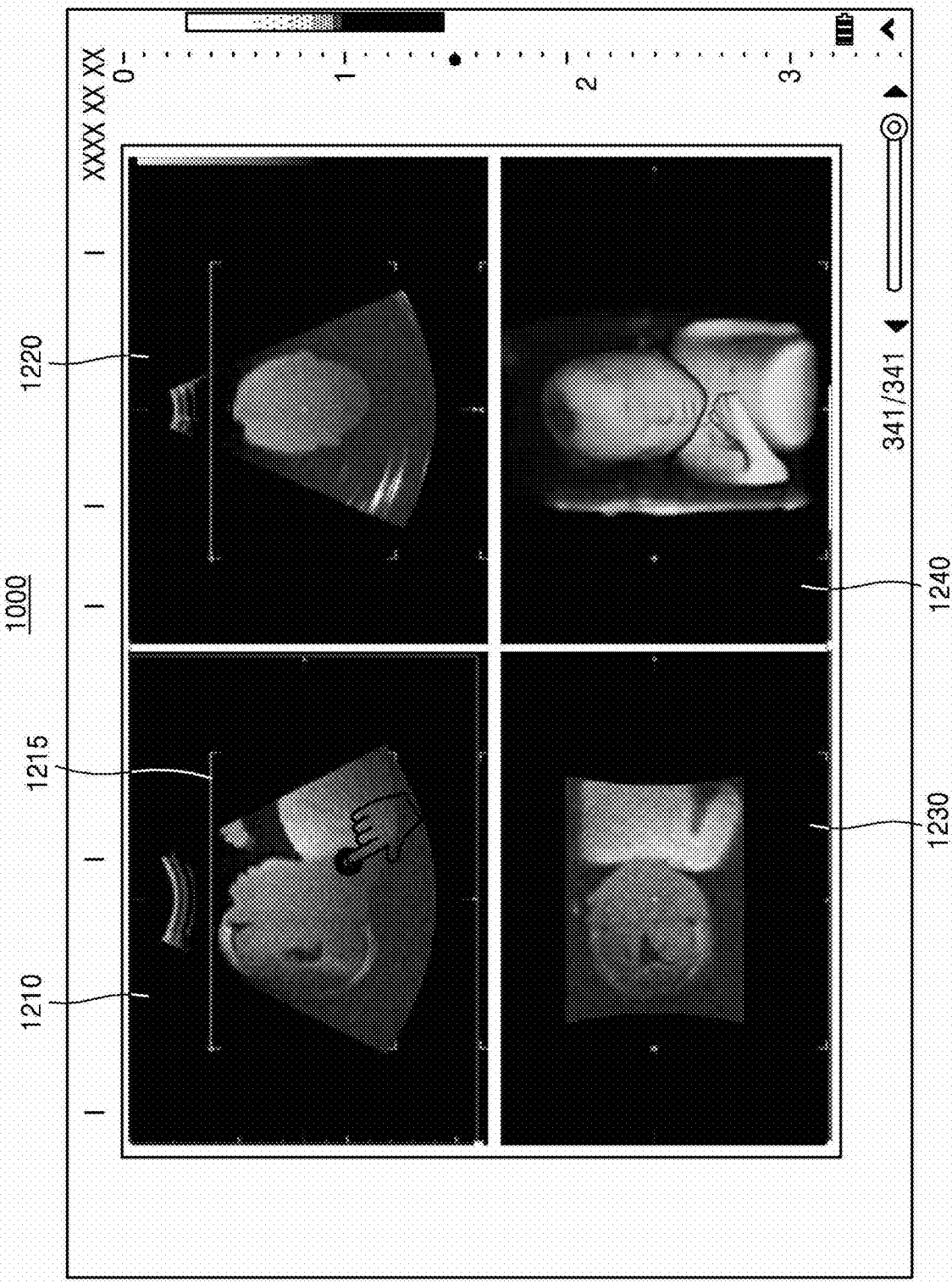
FIGS. 12A and 12B illustrate an example in which an ultrasound diagnosis apparatus receives a user input for setting opacity with respect to a depth, according to another embodiment.
Figure 12B:
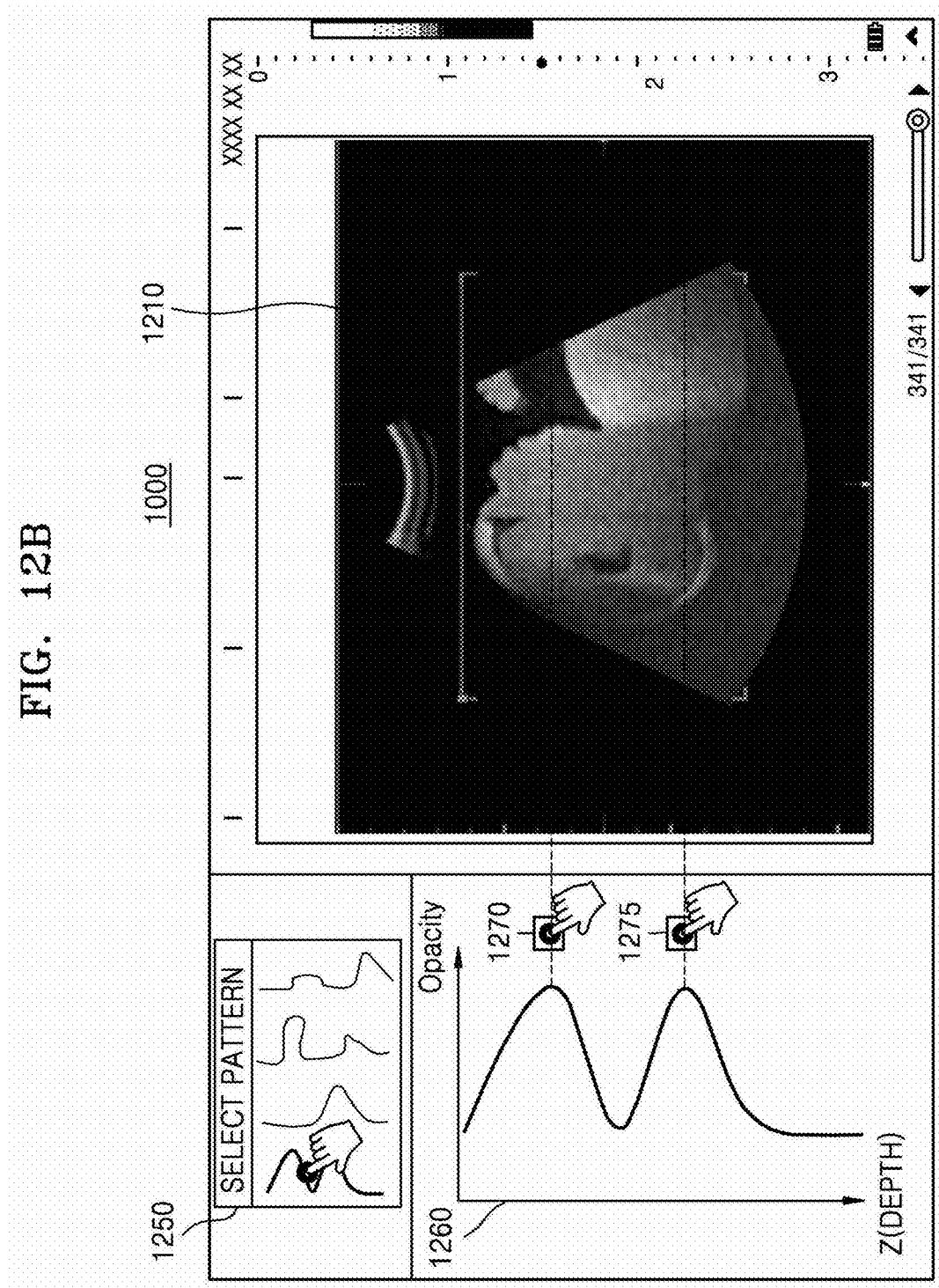

FIGS. 12A and 12B illustrate an example in which the ultrasound diagnosis apparatus 1000 receives a user input for setting opacity with respect to a depth, according to another embodiment.

Referring to FIG. 12A, the ultrasound diagnosis apparatus 1000 may display an ultrasound image 1210 representing a sagittal plane or an A plane of an object together with an ultrasound image 1220 representing a coronal plane or B plane of the object. Furthermore, the ultrasound diagnosis apparatus 1000 may display an ultrasound image 1230 representing an axial plane or C plane of the object. Furthermore, the ultrasound diagnosis apparatus 1000 may display an ultrasound image 1240 showing a 3D volume of an ROI 1215 set in the ultrasound image 1210.

The ultrasound diagnosis apparatus 1000 may receive a user input for selecting one from among the ultrasound images 1210, 1220, 1230, and 1240 of the object. For example, the ultrasound diagnosis apparatus 1000 may receive a user input for selecting the ultrasound image 1210 representing the sagittal plane of the object.

Referring to FIG. 12B, the ultrasound diagnosis apparatus 1000 may receive a user input for selecting an opacity with respect to a depth of the object in the selected ultrasound image 1210.

For example, the ultrasound diagnosis apparatus 1000 may display a plurality of patterns 1250, each pattern showing different opacities according to a depth. When a user input for selecting one from among the plurality of patterns 1250 is received, the ultrasound diagnosis apparatus 1000 may display the selected pattern on a graph 1260 of opacity with respect to a depth.

If the selected pattern has highest peaks of opacities at two depths, the ultrasound diagnosis apparatus 1000 may display scroll buttons 1270 and 1275 for selecting the two depths.

The ultrasound diagnosis apparatus 1000 may receive a user input for selecting the two depths by moving the scroll buttons 1270 and 1275. For example, the ultrasound diagnosis apparatus 1000 may receive a user input for selecting a depth at which a jaw of a fetus is located as a first depth and a depth at which a nuchal of the fetus is located as a second depth.

When a user input for selecting two depths is received, the ultrasound diagnosis apparatus 1000 may display an ultrasound image showing a 3D volume of an object and representing finer details of tissues located at the first and second depths.

FIG. 13 is a flowchart of a method, performed by the ultrasound diagnosis apparatus 1000, of displaying a volume of a 3D volume, which is located below a depth set by a user, according to an embodiment.

The ultrasound diagnosis apparatus 1000 may receive a user input for setting a depth of a volume of a 3D volume to be displayed (S1310).

For example, the ultrasound diagnosis apparatus 1000 may display an ultrasound image showing a cross-section of a volume to be displayed and a user interface for setting a depth of the volume to be displayed. The ultrasound diagnosis apparatus 1000 may receive a user input for adjusting a depth of a 3D volume to be displayed via the user interface.

Furthermore, for example, as shown in FIG. 11B, the ultrasound diagnosis apparatus 1000 may receive a user input for selecting one point in an ultrasound image on which a depth direction is indicated.

The ultrasound diagnosis apparatus 1000 may display a volume of the 3D volume located below the set depth by adjusting an opacity of a volume of the 3D volume located above the set depth to "0" (S1320).

The ultrasound diagnosis apparatus 1000 may display a volume of the 3D volume located below the set depth while not displaying a volume of the 3D volume located above the set depth by adjusting opacity of the portion above the set depth to less than or equal to a reference value. The reference value may be a value in the range of 0 to 10, but is not limited thereto.

In this case, the ultrasound diagnosis apparatus 1000 may display a surface and an internal structure of a 3D volume located down from the set depth.

Figure 14B:
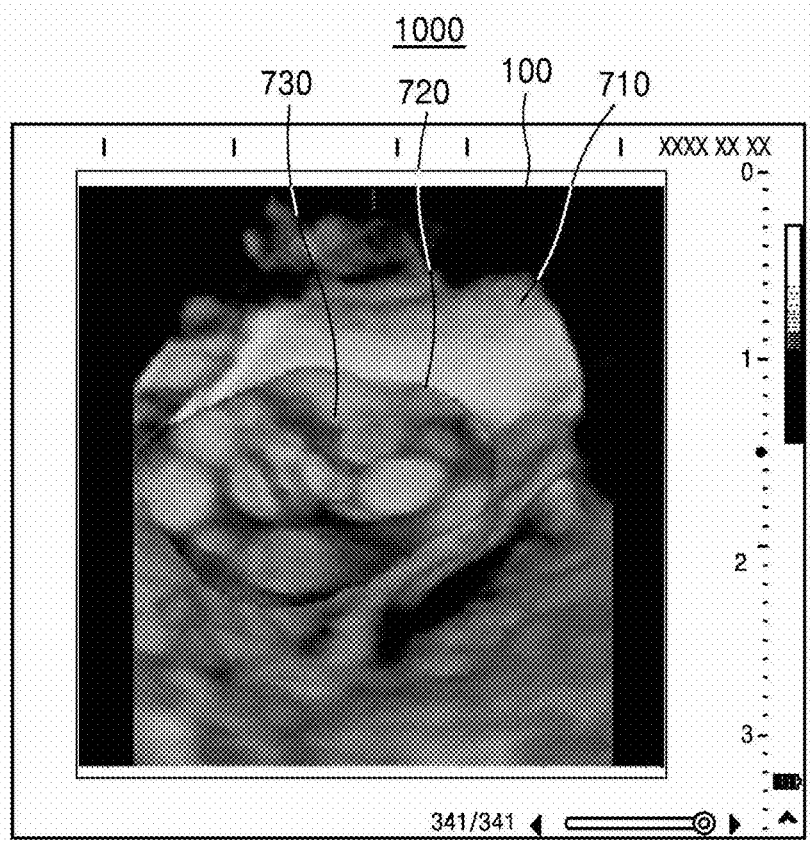

FIGS. 14A and 14B illustrate an example in which the ultrasound diagnosis apparatus 1000 displays an internal structure of a 3D volume located down from a depth set by a user, according to an embodiment.

Referring to FIG. 14A, opacities with respect to a depth set by the user may have a pattern in which opacity from a surface of a 3D volume to depth Z1 may be set to "0", an opacity at the depth Z1 has a highest value, and opacity decreases in a depth direction extending away from the depth Z1.

Referring to FIG. 14B, the ultrasound diagnosis apparatus 1000 may receive a user input for setting an ROI 720 in an ultrasound image 100 showing a surface 710 of an ovary and display follicles 730 in the ovary, which are located below the ROI 720, on the set ROI 720.

In this case, the ultrasound diagnosis apparatus 1000 may display the follicles 730 located in a depth direction away from the depth Z1 from among a plurality of follicles located below the ROI 720. For example, the ultrasound diagnosis apparatus 1000 may show contours of the follicles and display the interior of the follicles as being transparent or opaque based on a gradient between adjacent voxels and the interior of the follicles, thereby displaying the follicles 730 located at the depth Z1 together with those located in the depth direction.

Furthermore, since an opacity value is set to decrease in the depth direction away from the depth Z1, the ultrasound diagnosis apparatus 1000 may determine again an opacity value for a voxel by taking into account an opacity value corresponding to a depth of the voxel as well as a gradient between the voxel and its adjacent voxel. Accordingly, the ultrasound diagnosis apparatus 1000 may display contours of follicles 730 located close to the depth Z1 in more detail while displaying the follicles 730 more dimly toward the depth direction.

Figure 14C:
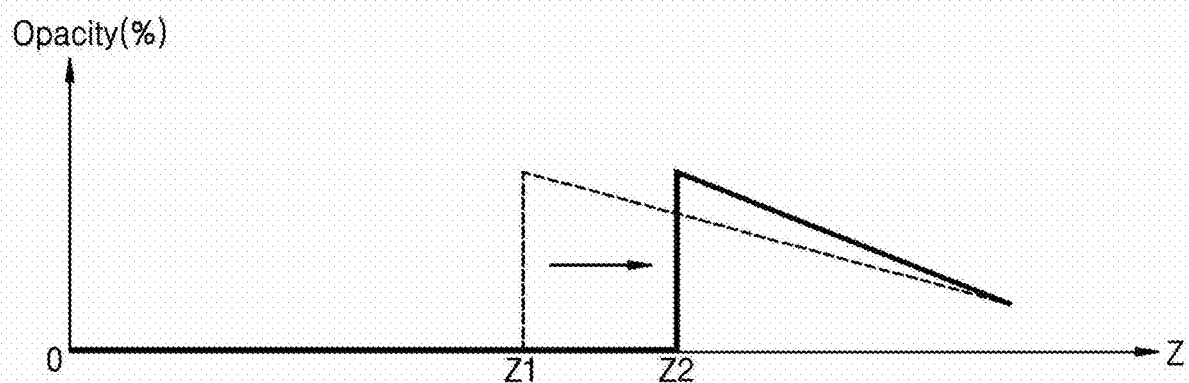
FIGS. 14C and 14D illustrate an example in which an ultrasound diagnosis apparatus displays an internal structure of a 3D volume located down from a depth set by a user, according to another embodiment.
Figure 14D:
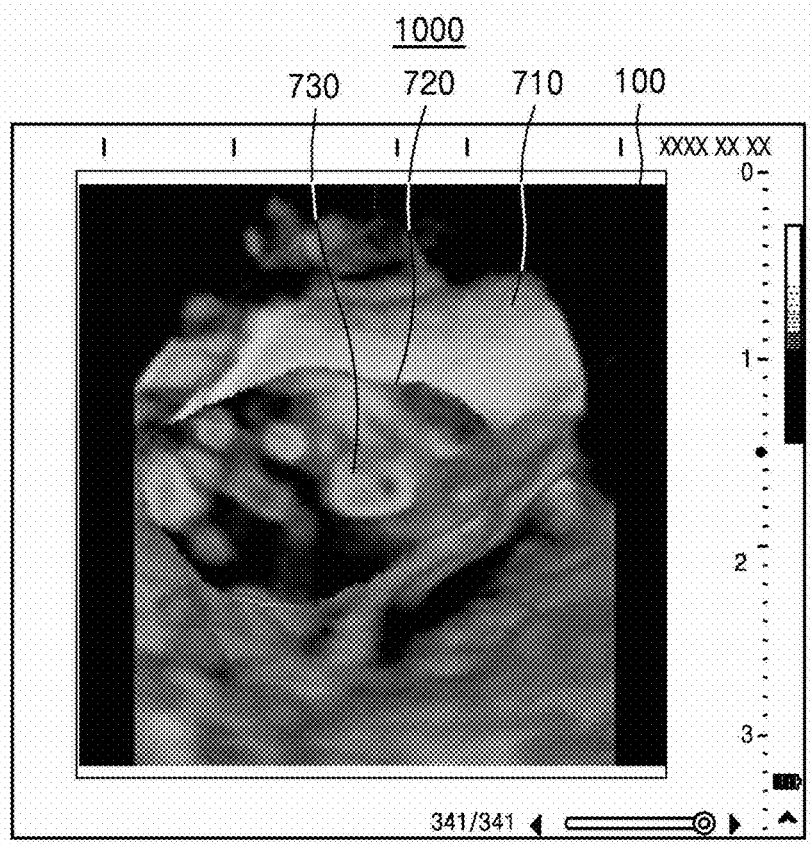

FIGS. 14C and 14D illustrate an example in which the ultrasound diagnosis apparatus 1000 displays an internal structure of a 3D volume located down from a depth set by a user, according to another embodiment Referring to FIG. 14C, the ultrasound diagnosis apparatus 1000 may receive a user input for adjusting a depth of a volume to be displayed in a 3D volume.

For example, the ultrasound diagnosis apparatus 1000 may receive a user input for changing a depth of a volume to be displayed from depth Z1 to depth Z2.

Referring to FIG. 14D, as the depth of the volume to be displayed increases from the depth Z1 to the depth Z2, the ultrasound diagnosis apparatus 1000 may display follicles 730 located in a depth direction away from the depth Z2 from among a plurality of follicles located below an ROI 720.

Figure 15:
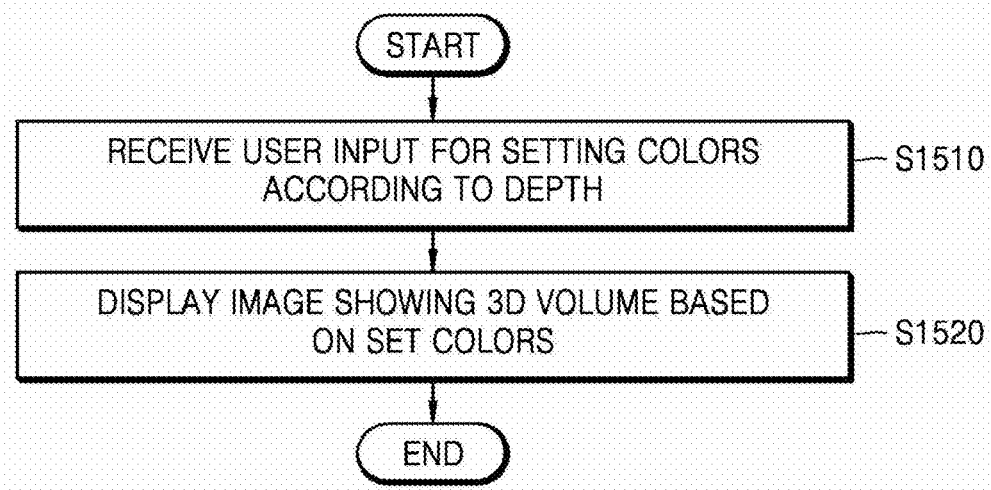
FIG. 15 is a flowchart of a method, performed by an ultrasound diagnosis apparatus, of displaying an image showing a 3D volume based on a color set according to a depth, according to an embodiment.

FIG. 15 is a flowchart of a method, performed by the ultrasound diagnosis apparatus 1000, of displaying an image showing a 3D volume based on a color set according to a depth, according to an embodiment.

The ultrasound diagnosis apparatus 1000 may receive a user input for setting colors according to a depth (S1510).

The ultrasound diagnosis apparatus 1000 may receive a user input for setting a first color for a first depth and a second color for a second depth. Furthermore, the ultrasound diagnosis apparatus 1000 may display an ultrasound image of an object, indicate a direction and a degree of a depth on the displayed ultrasound image, and receive a user input for selecting a color corresponding to a depth of a selected point in the ultrasound image by receiving a user input for selecting the point and the color corresponding to the point.

Furthermore, the ultrasound diagnosis apparatus 1000 may segment a part, organ, or tissue in an ultrasound image into regions to be displayed, select one from among regions of the segmented part, organ, or tissue, and receive a user input for selecting a color with respect to a depth by receiving a user input for selecting a color corresponding to the selected region of the part, organ, or tissue.

The ultrasound diagnosis apparatus 1000 may display an image showing a 3D volume based on the set colors (S1520).

For example, the ultrasound diagnosis apparatus 1000 may determine a color set at a depth where a voxel is located as being a color corresponding to the voxel. The ultrasound diagnosis apparatus 1000 may display an image showing a 3D volume by performing volume rendering based on a color corresponding to a voxel.

Figure 16:
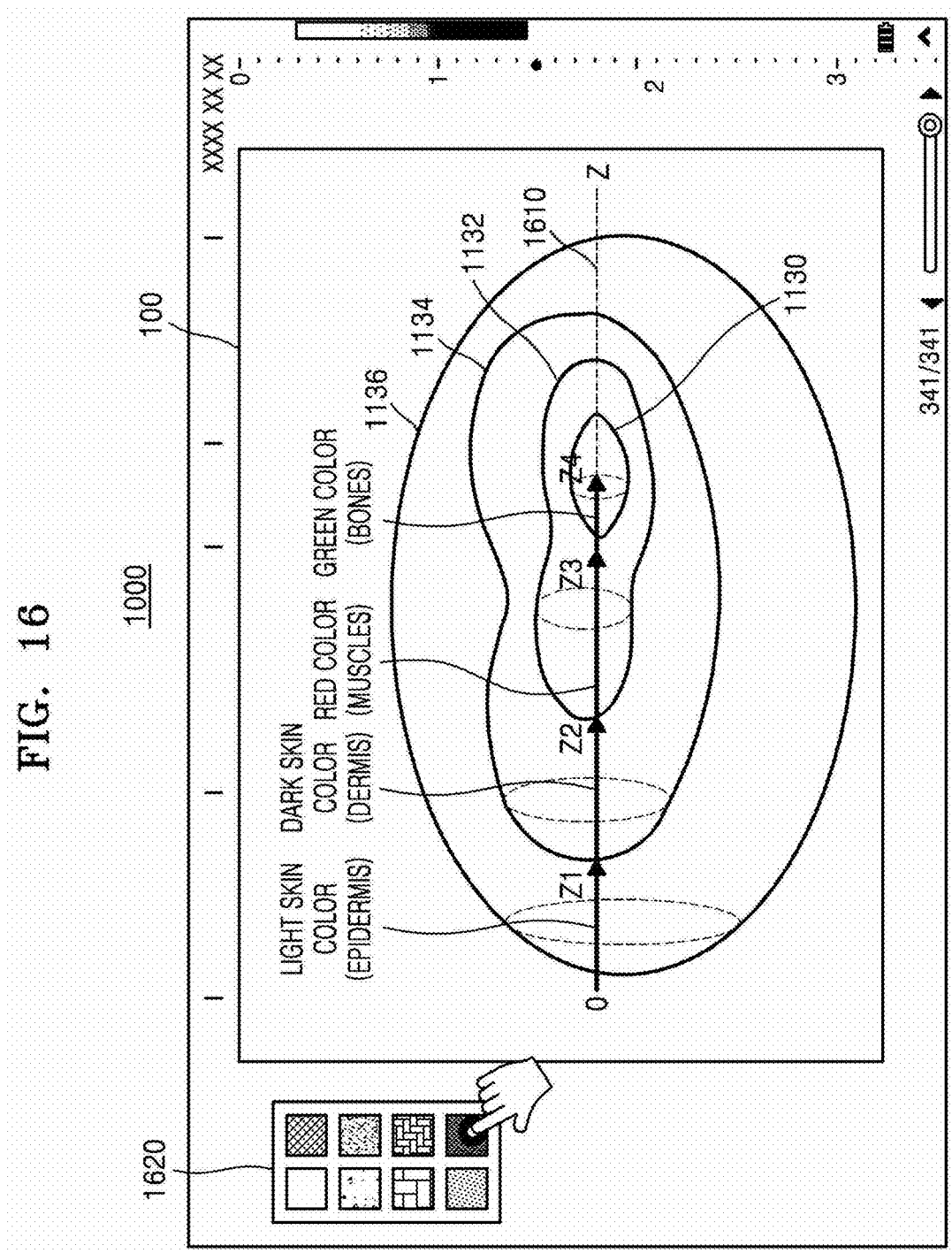
FIG. 16 illustrates an example in which an ultrasound diagnosis apparatus receives a user input for setting a color according to a depth, according to an embodiment.

FIG. 16 illustrates an example in which the ultrasound diagnosis apparatus 1000 receives a user input for setting a color according to a depth, according to an embodiment.

Referring to FIG. 16, the ultrasound diagnosis apparatus 1000 may display an ultrasound image 100 showing an object while displaying an indicator 1610 representing a depth direction on the ultrasound image 100.

Examples of the ultrasound image 100 may include an A mode image, a B mode image, an M mode image, a Doppler image, an ultrasound image showing a 3D volume, and a Crystal Vue image, but are not limited thereto.

Furthermore, the ultrasound diagnosis apparatus 1000 may display a user interface 1620 including a plurality of selectable colors. The user interface 1620 may include a color bar, a color palette, etc., but is not limited thereto.

The ultrasound diagnosis apparatus 1000 may receive a user input for selecting a depth and a color corresponding to the selected depth. For example, the ultrasound image 100 may represent bones 1130, muscles 1132 surrounding the bones 1130, a dermis 1134 surrounding the muscles 1132, and an epidermis 1136 surrounding the dermis 1134. Thus, the user may select a depth from 0 to Z1 where the epidermis 1136 is located and a light skin color corresponding to the selected depth. Furthermore, the user may select a dark skin color corresponding to a depth from Z1 to Z2 where the dermis 1134 is located. Furthermore, the user may select a red color corresponding to a depth from Z2 to Z3 where the muscles 1132 are located. Furthermore, the user may select a green color corresponding to a depth from Z3 to Z4 where the bones 1130 are located.

When a user input for selecting a depth and a color corresponding to the selected depth is received, the ultrasound diagnosis apparatus 1000 may determine a color selected for a depth where a voxel is located as being a color corresponding to the voxel and generate an ultrasound image showing a 3D volume based on the determined color.

Figure 17:
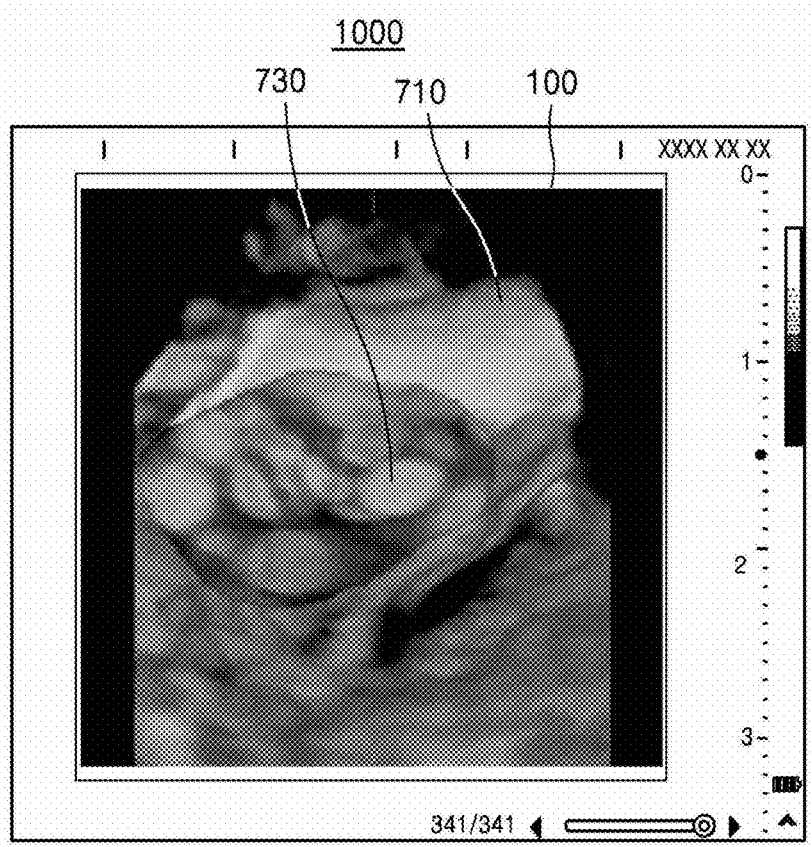
FIG. 17 illustrate an example in which an ultrasound diagnosis apparatus generates an ultrasound image showing a 3D volume based on a color set by the user according to a depth, according to an embodiment.

FIG. 17 illustrate an example in which the ultrasound diagnosis apparatus 1000 generates an ultrasound image showing a 3D volume based on a color set by the user according to a depth, according to an embodiment.

Referring to FIG. 17, the ultrasound diagnosis apparatus 1000 may display an ultrasound image 100 showing a surface 710 of an ovary and follicles 730 in the surface 710 of the ovary in different colors.

For example, after receiving a user input for selecting a yellow color as a color corresponding to a depth where the surface 710 of the ovary is located and a white color as a color corresponding to a depth where the follicles 730 in the surface 710 of the ovary, the ultrasound diagnosis apparatus 1000 may display the ultrasound image 100 showing the surface 710 of the ovary in the yellow color and the follicles 730 in the ovary in the white color.

Figure 18:
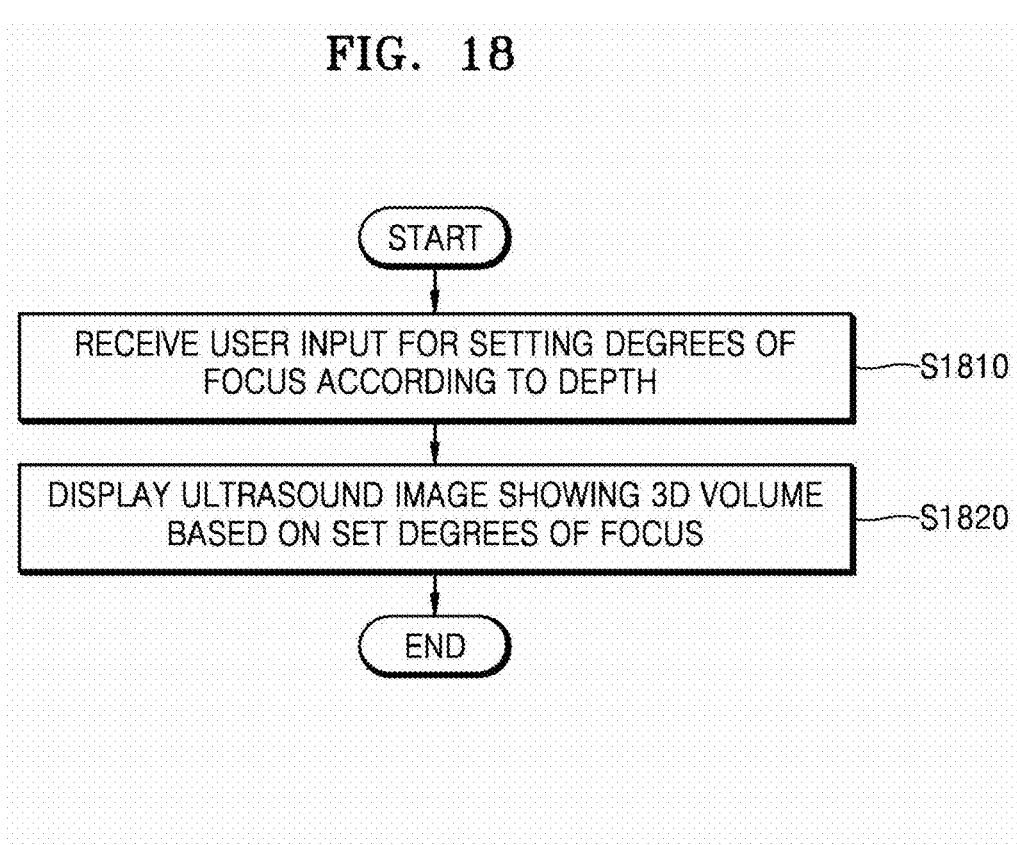
FIG. 18 is a flowchart of a method, performed by an ultrasound diagnosis apparatus, of displaying an image showing a 3D volume based on a degree of focus with respect to a depth set by a user, according to an embodiment.

FIG. 18 is a flowchart of a method, performed by the ultrasound diagnosis apparatus 1000, of displaying an image showing a 3D volume based on a degree of focus with respect to a depth set by a user, according to an embodiment.

The ultrasound diagnosis apparatus 1000 may receive a user input for setting degrees of focus according to a depth (S1810).

According to an embodiment, the degree of focus may be referred to as sharpness.

The ultrasound diagnosis apparatus 1000 may receive a user input for setting a first degree of focus with respect to a first depth and a second degree of focus with respect to a second depth. Furthermore, the ultrasound diagnosis apparatus 1000 may display an ultrasound image of an object and receive a user input for selecting a degree of focus corresponding to a depth of a selected point in the ultrasound image by receiving a user input for selecting the point and the degree of focus corresponding to the depth of the point.

Furthermore, the ultrasound diagnosis apparatus 1000 may segment a part, organ, or tissue in an ultrasound image into regions to be displayed, select one from among regions of the segmented part, organ, or tissue, and receive a user input for selecting a degree of focus with respect to a depth by receiving a user input for selecting the degree of focus corresponding to the selected region of the part, organ, or tissue.

The ultrasound diagnosis apparatus 1000 may display an ultrasound image showing a 3D volume based on the set degrees of focus (S1820).

The ultrasound diagnosis apparatus 1000 may adjust the degree of focusing with respect to an ultrasound image by performing image filtering on the ultrasound image based on the degree of focus corresponding to a selected depth.

For example, the ultrasound diagnosis apparatus 1000 may generate an ultrasound image representing a selected depth more clearly than the other depths by performing 3D filtering with respect to the selected depth. Examples of a 3D filter may include an anisotropy diffusion filter, a directional filter, and a non-local mean filter, but are not limited thereto. Furthermore, the ultrasound diagnosis apparatus 1000 may receive a user input for setting a contrast or tint as well as a degree of focus according to a depth and display an ultrasound image showing a 3D volume based on the set contrast or tint.

Figure 19B:
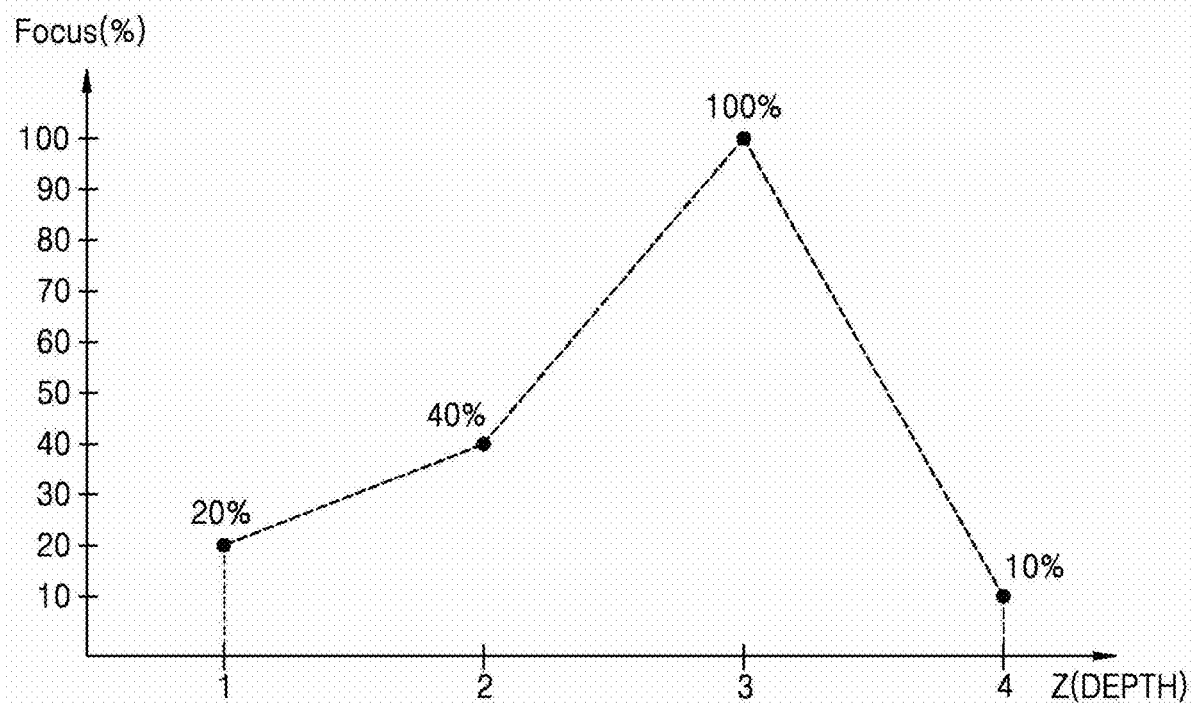

FIGS. 19A and 19B illustrate an example in which the ultrasound diagnosis apparatus 1000 receives a user input for setting a degree of focus according to a depth, according to an embodiment.

Referring to FIG. 19A, the ultrasound diagnosis apparatus 1000 may display an ultrasound image 100 while displaying a user interface for setting a degree of focus according to a depth on the ultrasound image 100.

Examples of the ultrasound image 100 may include an A mode image, a B mode image, an M mode image, a Doppler image, an ultrasound image showing a 3D volume, and a Crystal Vue image, but are not limited thereto.

For example, the user interface for setting a degree of focus may be displayed on the ultrasound image 100 and include a coordinate axis (Z axis) representing a degree of a depth and a coordinate axis (Focus axis) representing a degree of focus.

The user may set a degree of focus for a part, which is located at a depth of interest among parts of the object in the ultrasound image 100, to a high value via the user interface displayed on the ultrasound image 100.

Referring to FIG. 19B, the degree of focus with respect to a depth may be set in the ultrasound diagnosis apparatus 1000 based on the user input received as shown in FIG. 19A.

Figure 19C:
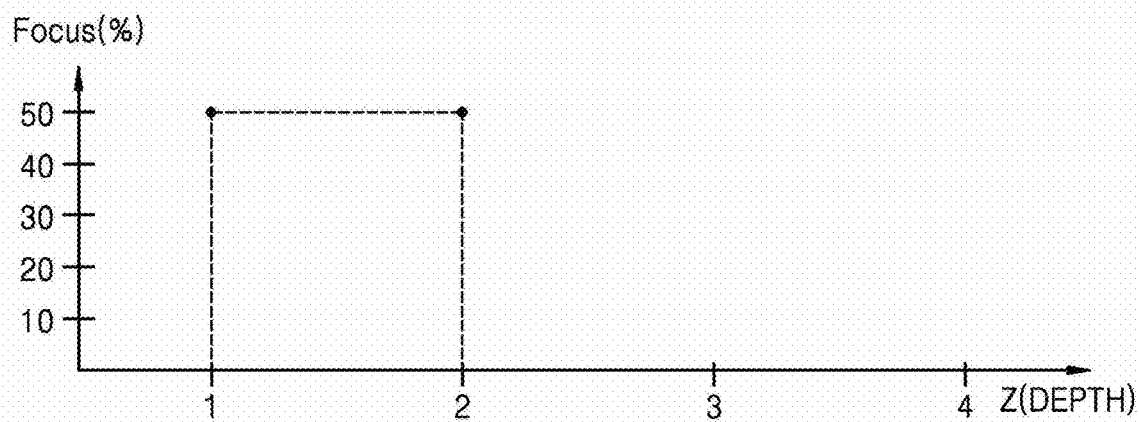

Referring to FIG. 19C, a degree of focus with respect to a depth interval may be set in the ultrasound diagnosis apparatus 1000.

FIGS. 20A through 20D illustrate an example in which the ultrasound diagnosis apparatus 1000 displays an ultrasound image showing a 3D volume based on a degree of focus with respect to a depth selected by a user, according to an embodiment.

Referring to FIG. 20A, the ultrasound diagnosis apparatus 1000 may generate an ultrasound image 100 showing a surface 710 of an ovary and follicles 730 at a first depth from among follicles located below an ROI 720.

Figure 20B:
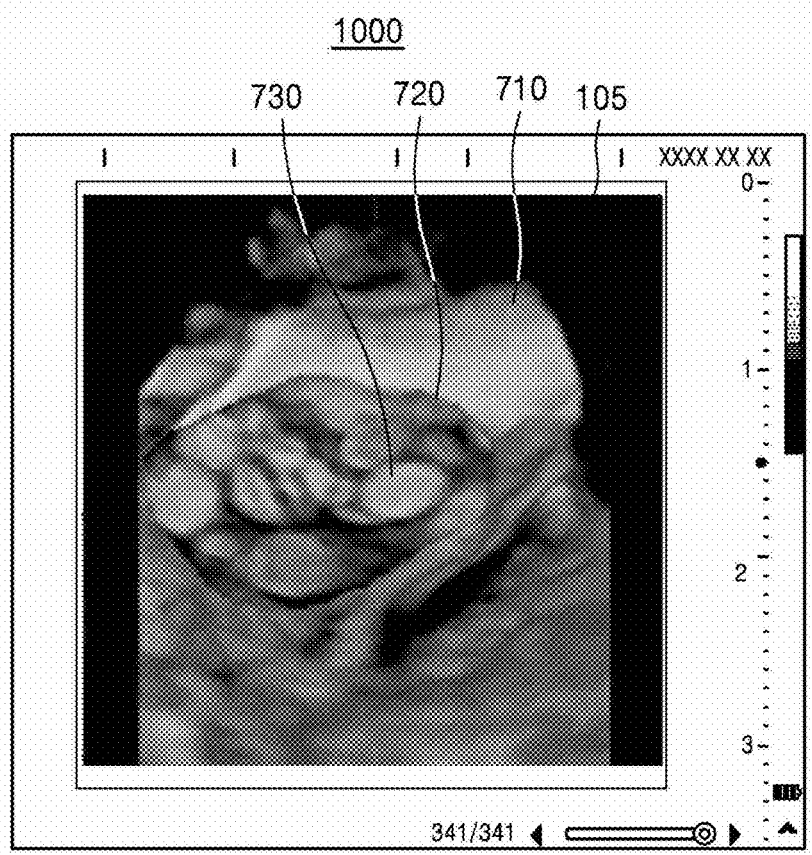

In this case, when a first degree of focus is set with respect to the first depth, as shown in FIG. 20B, the ultrasound diagnosis apparatus 1000 may display an ultrasound image 105 representing the follicles 730 located at the first depth in an elaborate way based on the first degree of focus by performing 3D filtering with respect to the first depth of 3D volume data representing the ovary.

Figure 20C:
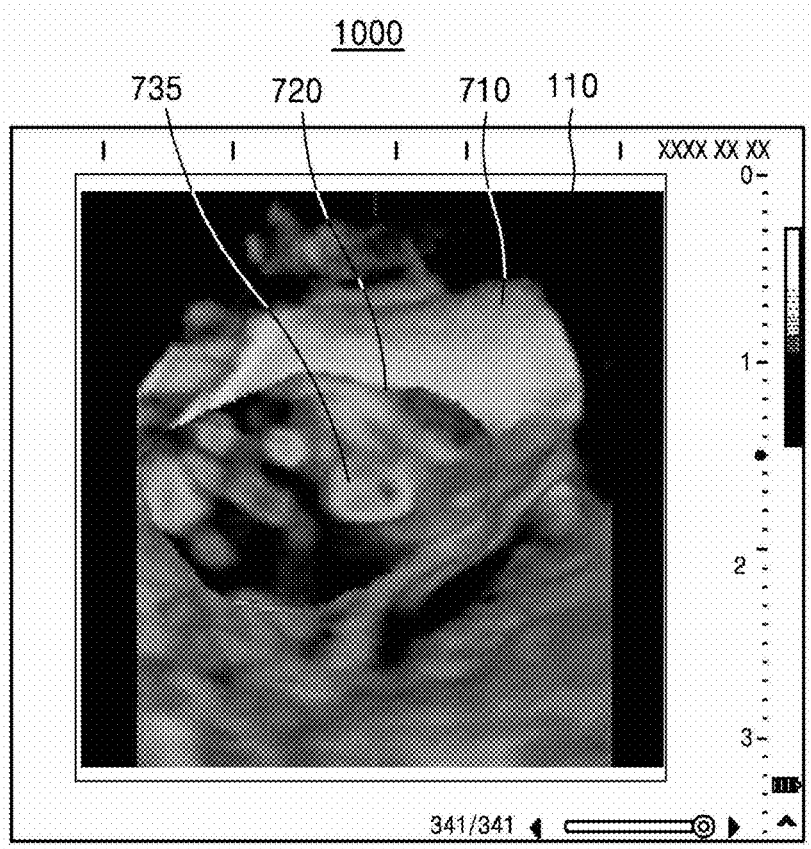

Furthermore, referring to FIG. 20C, when a user input for displaying on the ROI 720 follicles 735 located below a second depth from among follicles located below the ROI 720 is received, the ultrasound diagnosis apparatus 1000 may generate an ultrasound image 110 showing the follicles 735 in the ovary located below the second depth on the ROI.

In this case, when a second degree of focus is set with respect to the second depth, as shown in FIG. 20D, the ultrasound diagnosis apparatus 1000 may display an ultrasound image 115 representing the follicles 735 located at the second depth in an elaborate way based on the second degree of focus by performing 3D filtering with respect to the second depth of 3D volume data representing the ovary.

FIG. 21 is a flowchart of a method, performed by the ultrasound diagnosis apparatus 1000, of displaying an ultrasound image showing a 3D volume based on a shape of an ROI set according to a depth selected by a user, according to an embodiment.

The ultrasound diagnosis apparatus 1000 may receive a user input for setting ROIs with respect to a depth of a 3D volume (S2110).

The ultrasound diagnosis apparatus 1000 may receive a user input for setting ROIs having different shapes according to a depth of a 3D volume.

For example, the ultrasound diagnosis apparatus 1000 may receive a user input for setting a circular ROI for a first depth of a 3D volume and a quadrangular ROI for a second depth. Furthermore, the ultrasound diagnosis apparatus 1000 may receive a user input for setting an ROI having a first size for a first depth of the 3D volume and an ROI having a second size for a second depth. Furthermore, the ultrasound diagnosis apparatus 1000 may receive a user input for setting a hexahedral 3D ROI for first to second depths and a cylindrical 3D ROI for second to third depths.

The ultrasound diagnosis apparatus 1000 may display an ultrasound image showing a 3D volume based on the set ROIs (S2120).

The ultrasound diagnosis apparatus 1000 may display an ultrasound image showing a 3D volume based on a shape of an ROIO set according to a depth.

Figure 22A:
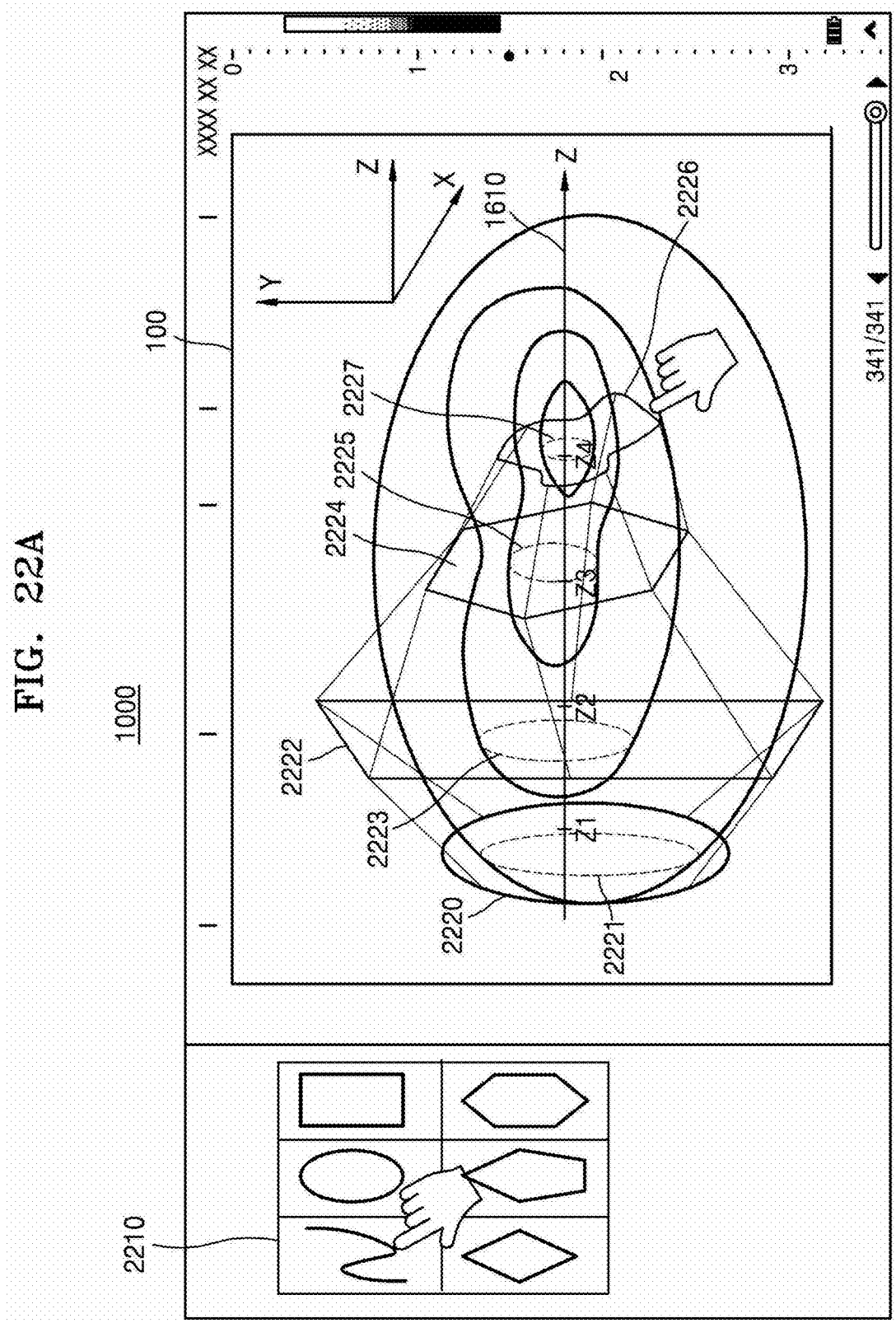
FIGS. 22A through 22C illustrate an example in which an ultrasound diagnosis apparatus receives a user input for setting ROIs having different shapes according to a depth, according to an embodiment.
Figure 22B:
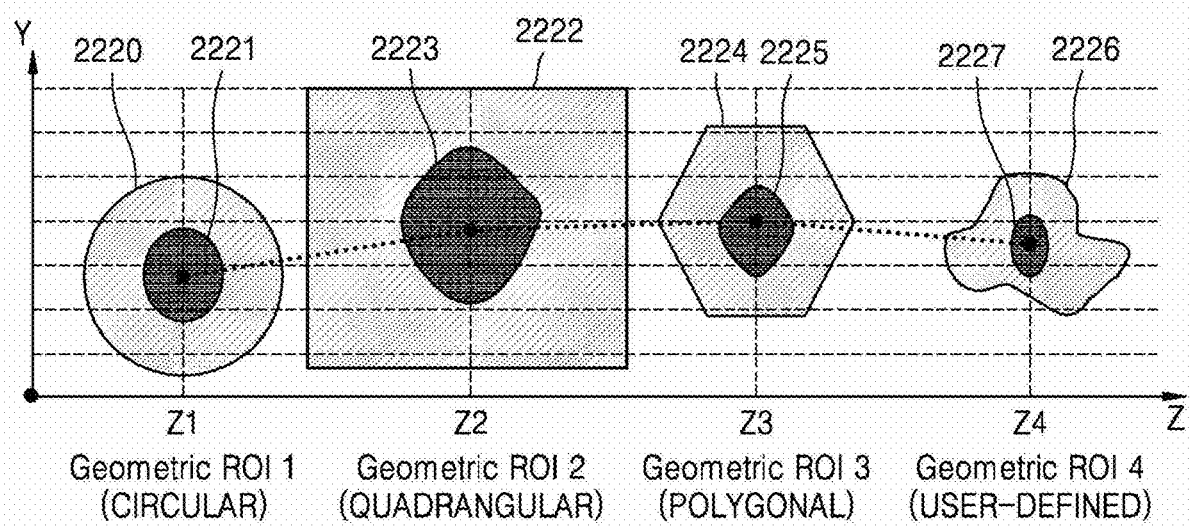
Figure 22C:
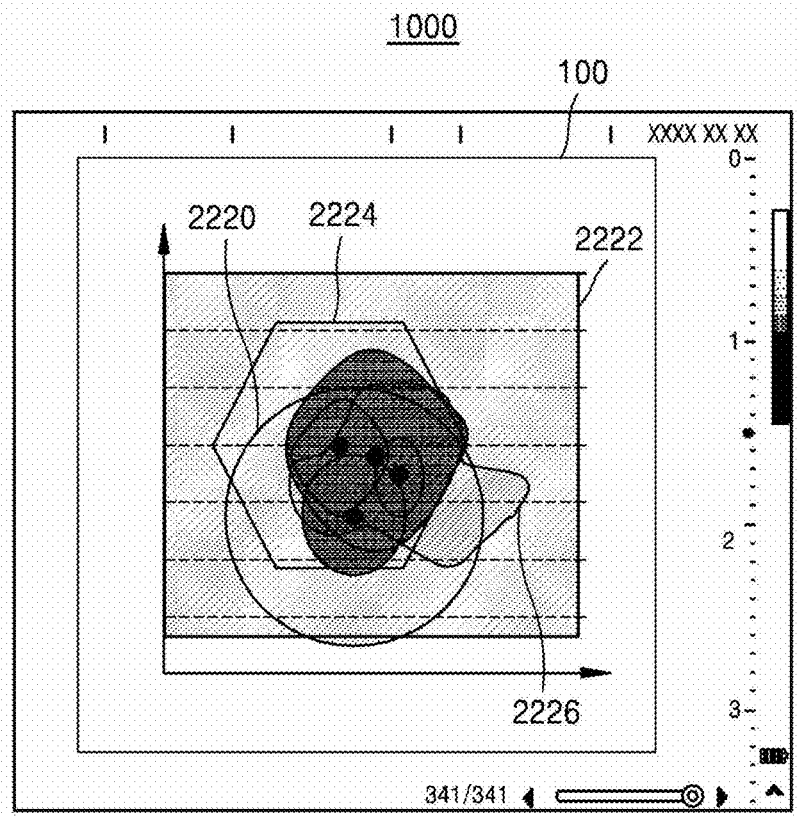

FIGS. 22A through 22C illustrate an example in which the ultrasound diagnosis apparatus 1000 receives a user input for setting ROIs having different shapes according to a depth, according to an embodiment.

Referring to FIG. 22A, the ultrasound diagnosis apparatus 1000 may display an ultrasound image 100 while displaying a user interface for setting ROIs having different shapes according to a depth on the ultrasound image 100.

Examples of the ultrasound image 100 may include an A mode image, a B mode image, an M mode image, a Doppler image, an ultrasound image showing a 3D volume, and a Crystal Vue image, but are not limited thereto.

For example, the user interface for setting ROIs may be displayed on the ultrasound image 100 and include a coordinate axis 1610 representing a degree of a depth and a plurality of selectable geometric figures 2210 having different shapes.

When a user input for selecting a depth and one of the plurality of geometric figures 2210 corresponding to the selected depth is received, the ultrasound diagnosis apparatus 1000 may determine a shape of the selected geometric figure as being a shape of an ROI corresponding to the selected depth. In this case, the ultrasound diagnosis apparatus 1000 may receive a user input for adjusting a size of the ROI.

Furthermore, the ultrasound diagnosis apparatus 1000 may determine a figure directly created by the user as well as a geometric figure having a predetermined shape as being a shape of the ROI. For example, when a user input for selecting a depth and drawing a figure is input, the ultrasound diagnosis apparatus 1000 may determine a shape of the figure drawn by the user as being a shape of an ROI corresponding to the selected depth.

Furthermore, when a user input for setting ROIs 2220, 2222, 2224, and 2226 corresponding to depths is received, the ultrasound diagnosis apparatus 1000 may display points where the set ROIs 2220, 2222, 2224, and 2226 respectively meet an object on the ultrasound image 100.

Referring to FIG. 22B, the ultrasound diagnosis apparatus 1000 may determine ROIs having different sizes and shapes according to depths based on the received user input described with reference to FIG. 22A.

Referring to FIG. 22C, the ultrasound diagnosis apparatus 1000 may display an ultrasound image 100 showing a 3D volume based on ROIs set according to depths selected by the user.

For example, the ultrasound diagnosis apparatus 1000 may display the ultrasound image 100 represented by rendering only the set ROIs.

Furthermore, for example, when a user input for moving a view plane in a depth direction (Z-axis direction) is received, the ultrasound diagnosis apparatus 1000 may generate an ultrasound image by rendering only ROIs set with regard to depths located below a moved depth and display the generated ultrasound image.

Furthermore, for example, the ultrasound diagnosis apparatus 1000 may generate a 3D volume by connecting set ROIs together and generate an ultrasound image by performing volume rendering with respect to the generated 3D volume.

Figure 23A:
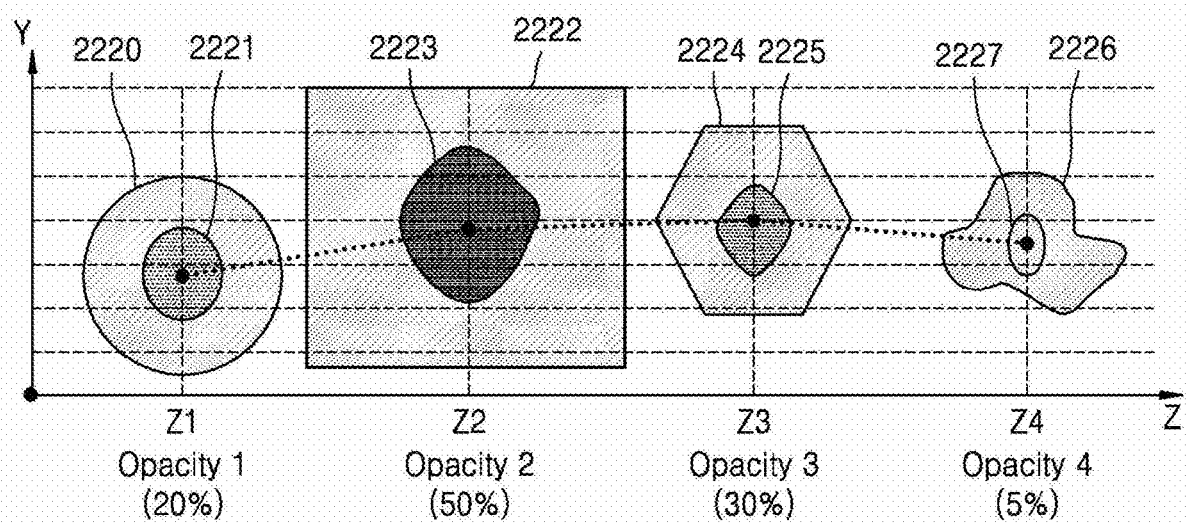
FIGS. 23A and 23B illustrate an example in which an ultrasound diagnosis apparatus displays an ultrasound image showing a 3D volume based on opacities that are respectively set for a plurality of ROIs selected according to a depth, according to an embodiment.
Figure 23B:
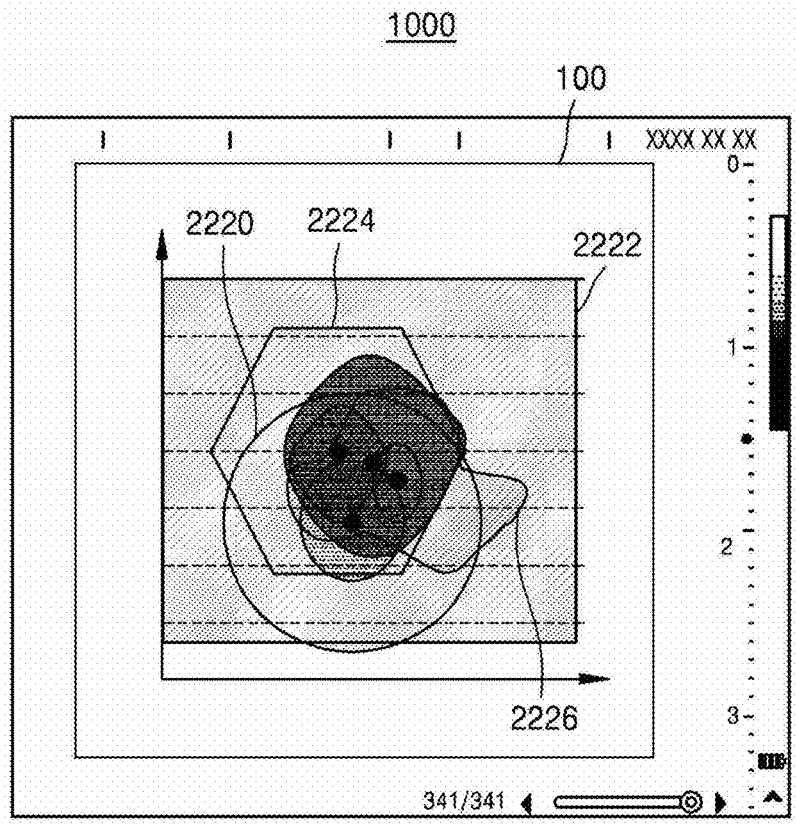

FIGS. 23A and 23B illustrate an example in which the ultrasound diagnosis apparatus 1000 displays an ultrasound image showing a 3D volume based on opacities that are respectively set for a plurality of ROIs selected according to a depth, according to an embodiment.

Referring to FIG. 23A, the ultrasound diagnosis apparatus 1000 may receive a user input for respectively setting opacities for a plurality of ROIs with respect to depths.

For example, the ultrasound diagnosis apparatus 1000 may receive a user input for selecting an ROI at depth Z1 from among the plurality of ROIs with respect to depths and opacity of 20% for the selected ROI.

The ultrasound diagnosis apparatus 1000 may determine different opacities respectively for a plurality of ROIs selected according to a depth. For example, the ultrasound diagnosis apparatus 1000 may determine opacity of 20% for an ROI selected at the depth Z1, opacity of 50% for an ROI selected at depth Z2, opacity of 30% for an ROI selected at depth Z3, and opacity of 5% for an ROI selected at depth Z4.

Referring to FIG. 23B, the ultrasound diagnosis apparatus 1000 may generate an ultrasound image 100 showing a 3D volume based on opacities respectively set for a plurality of ROIs with respect to depths. In this case, as an ROI has a higher opacity, the ROI may be represented in more detail in the ultrasound image 100.

Figure 24A:
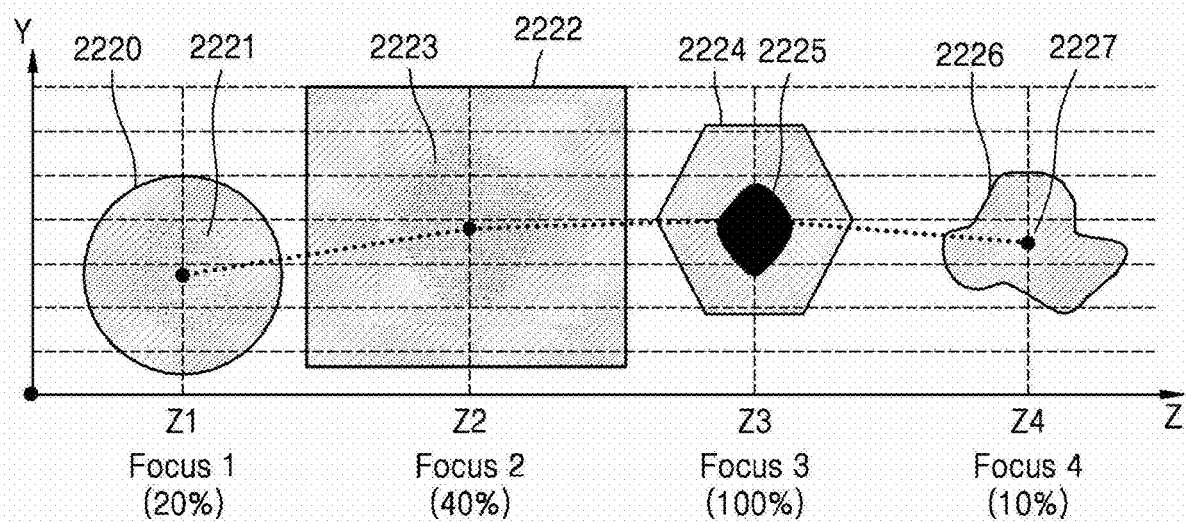
FIGS. 24A and 24B illustrate an example in which an ultrasound diagnosis apparatus displays an ultrasound image showing a 3D volume based on degrees of focus respectively set for a plurality of ROIs according to depths, according to an embodiment.
Figure 24B:
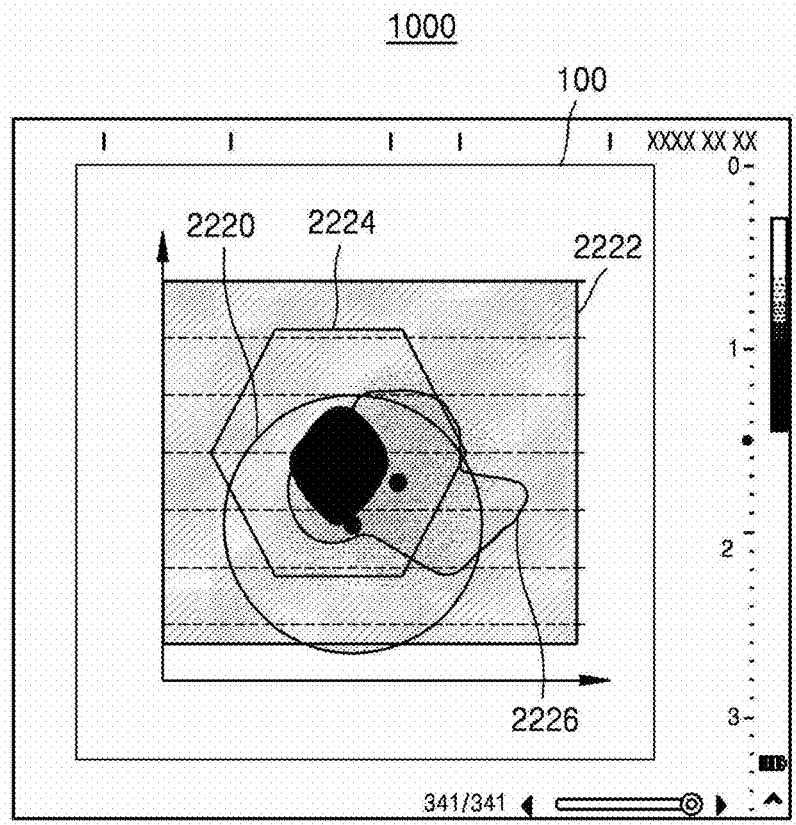

FIGS. 24A and 24B illustrate an example in which the ultrasound diagnosis apparatus 1000 displays an ultrasound image showing a 3D volume based on degrees of focus respectively set for a plurality of ROIs with respect to depths, according to an embodiment.

Referring to FIG. 24A, the ultrasound diagnosis apparatus 1000 may receive a user input for respectively setting degrees of focus for a plurality of ROIs with respect to depths.

For example, the ultrasound diagnosis apparatus 1000 may receive a user input for selecting an ROI at depth Z1 from among the plurality of ROIs with respect to depths and a degree of focus of 20% for the selected ROI.

The ultrasound diagnosis apparatus 1000 may determine different degrees of focus respectively for a plurality of ROIs selected according to a depth. For example, the ultrasound diagnosis apparatus 1000 may determine degree of focus of 20% for an ROI selected at the depth Z1, degree of focus of 40% for an ROI selected at depth Z2, degree of focus of 100% for an ROI selected at depth Z3, and degree of focus of 10% for an ROI selected at depth Z4.

Referring to FIG. 24B, the ultrasound diagnosis apparatus 1000 may generate an ultrasound image 100 showing a 3D volume based on degrees of focus respectively set for a plurality of ROIs with respect to depths. In this case, as an ROI has a higher degree of focus, the ROI may be represented more clearly in the ultrasound image 100.

Figure 25A:
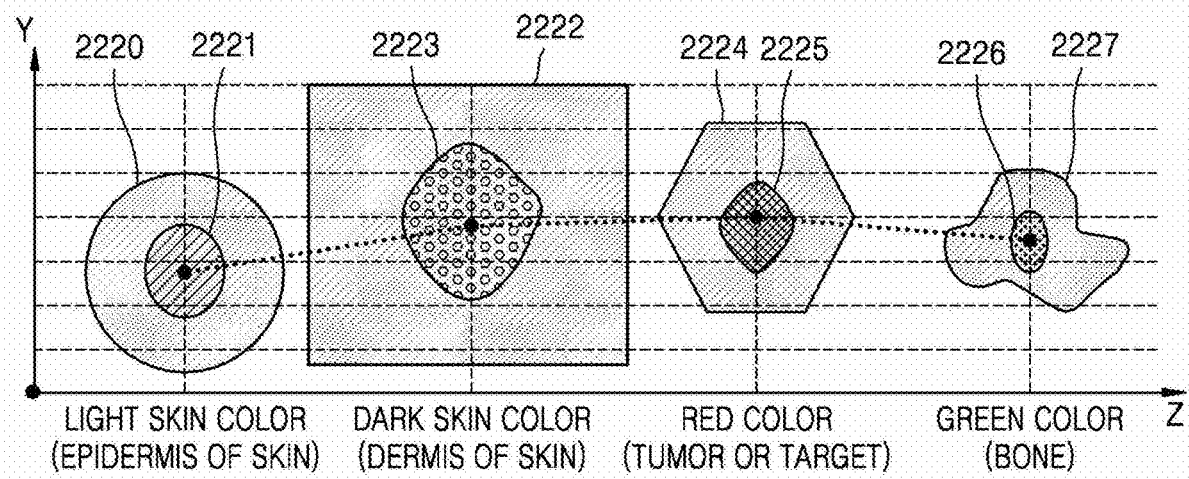
FIGS. 25A and 25B illustrate an example in which an ultrasound diagnosis apparatus displays an ultrasound image showing a 3D volume based on colors respectively set for a plurality of ROIs selected according to a depth, according to an embodiment.
Figure 25B:
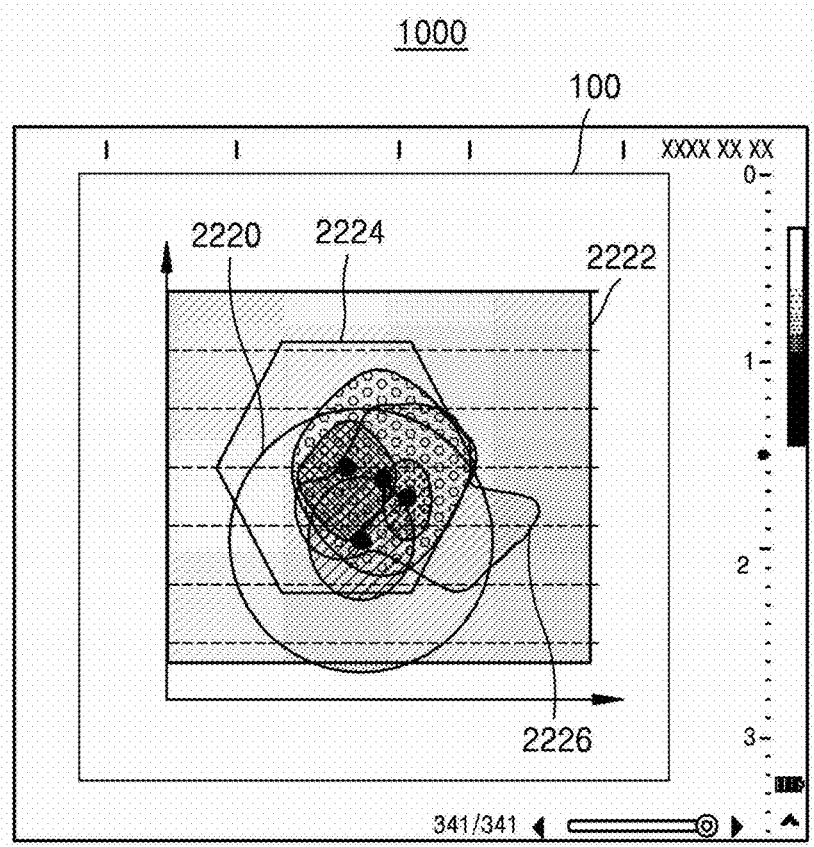

FIGS. 25A and 25B illustrate an example in which the ultrasound diagnosis apparatus 1000 displays an ultrasound image showing a 3D volume based on colors respectively set for a plurality of ROIs selected according to a depth, according to an embodiment.

Referring to FIG. 25A, the ultrasound diagnosis apparatus 1000 may receive a user input for respectively setting colors for a plurality of ROIs with respect to depths.

For example, the ultrasound diagnosis apparatus 1000 may receive a user input for selecting one from among the plurality of ROIs with respect to depths and a red color for the selected ROI.

The ultrasound diagnosis apparatus 1000 may determine different colors respectively for a plurality of ROIs selected according to a depth. For example, the ultrasound diagnosis apparatus 1000 may determine a light skin color for an ROI selected at depth Z1, a dark skin color for an ROI selected at depth Z2, a red color for an ROI selected at depth Z3, and a green color for an ROI selected at depth Z4.

Referring to FIG. 25B, the ultrasound diagnosis apparatus 1000 may generate an ultrasound image 100 showing a 3D volume based on colors respectively set for a plurality of ROIs with respect to depths. Thus, the user may determine a depth of a point based on colors displayed in the ultrasound image 100.

Figure 26:
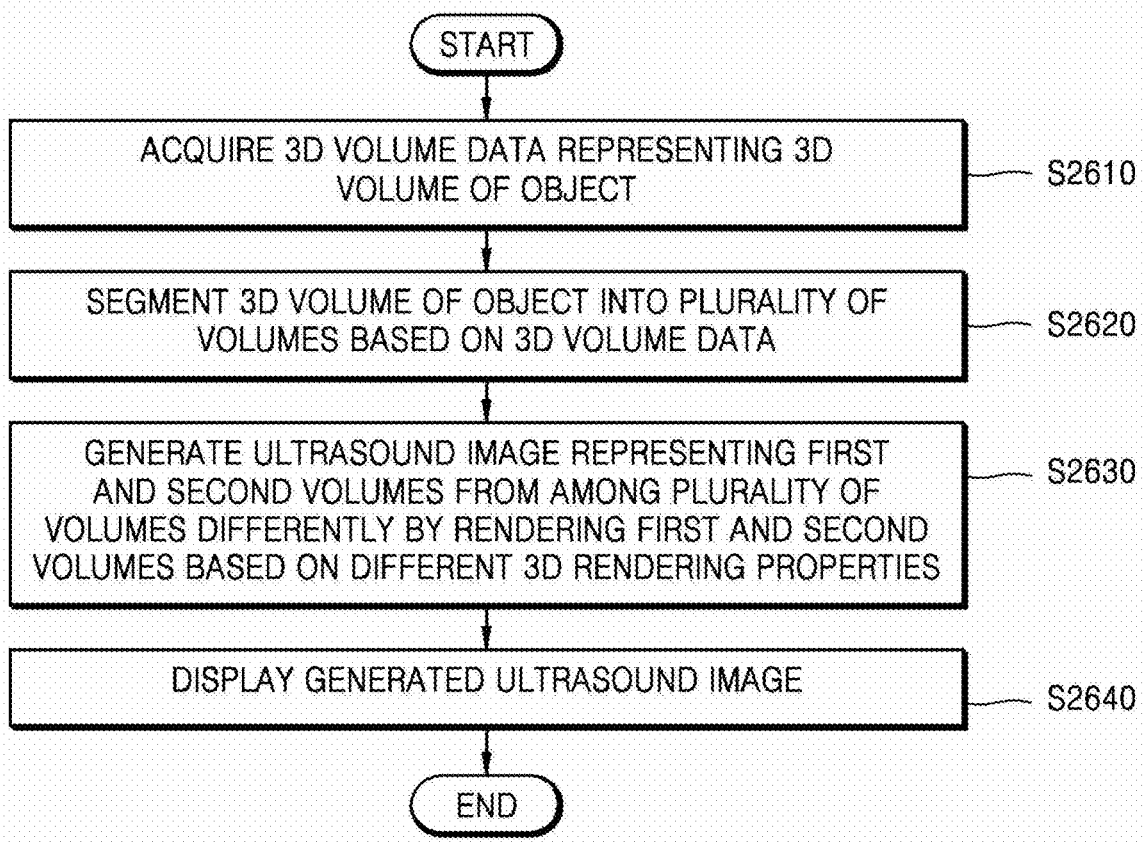
FIG. 26 is a flowchart of a method, performed by an ultrasound diagnosis apparatus, of representing a plurality of volumes differently by segmenting a 3D volume of an object into the plurality of volumes and setting 3D rendering properties respectively for the plurality of volumes, according to an embodiment.

FIG. 26 is a flowchart of a method, performed by the ultrasound diagnosis apparatus 1000, of representing a plurality of volumes in different ways by segmenting a 3D volume of an object into the plurality of volumes and setting 3D rendering properties respectively for the plurality of volumes, according to an embodiment.

The ultrasound diagnosis apparatus 1000 may acquire 3D volume data representing a 3D volume of an object (S2610).

The ultrasound diagnosis apparatus 1000 may acquire 3D volume data with respect to the object from an external device or server. For example, the ultrasound diagnosis apparatus 1000 may acquire 3D volume data with respect to the object from a hospital server or another medical apparatus in a hospital, which is connected thereto via a picture archiving and communication system (PACS).

Furthermore, the ultrasound diagnosis apparatus 1000 may transmit ultrasound signals to the object, receive ultrasound echo signals reflected by the object, and generate 3D volume data with respect to the object by processing the received ultrasound echo signals.

The ultrasound diagnosis apparatus 1000 may segment the 3D volume of the object into a plurality of volumes based on the acquired 3D volume data (S2620).

The ultrasound diagnosis apparatus 1000 may segment the 3D volume of the object into a plurality of volumes representing internal structures in the 3D volume of the object.

For example, a voxel having a high intensity from among voxels in the 3D volume or a voxel having a large gradient of intensity with_its adjacent voxel is most likely to be a meaningful target. For example, from among voxels in the 3D volume, high intensity voxels may correspond to a bone, and a voxel having a large gradient of intensity with its adjacent voxel may correspond to a boundary between two tissues. Thus, the ultrasound diagnosis apparatus 1000 may segment the 3D volume of the object into a plurality of volumes based on at least one of an intensity value of a voxel and a gradient of intensity with its adjacent voxel.

Furthermore, for example, the ultrasound diagnosis apparatus 1000 may obtain 3D coherence for the 3D volume data in order to measure homogeneity of the 3D volume data. Furthermore, the ultrasound diagnosis apparatus 1000 may obtain a structure tensor for the 3D volume data. The ultrasound diagnosis apparatus 1000 may determine, based on the obtained 3D coherence and structure tensor, whether voxels in the 3D volume form a linear or curved shape or are in a homogeneous region. By determining voxels forming a linear shape as being a volume representing a tube and voxels forming a curved shape as being a volume representing a boundary, the ultrasound diagnosis apparatus 1000 may segment the 3D volume of the object into a plurality of volumes.

Furthermore, for example, the ultrasound diagnosis apparatus 1000 may segment the 3D volume of the object into a plurality of volumes based on entropy values for voxels in the 3D volume. An entropy value for a voxel is a measure of uncertainty of the voxel, and may be determined to have a higher value as a value of its adjacent voxel is more random.

The ultrasound diagnosis apparatus 1000 may determine a region where voxels have lower entropy values as being a homogeneous region. On the other hand, the ultrasound diagnosis apparatus 1000 may determine a region where voxels have higher entropy values as being a meaningful target region. Accordingly, the ultrasound diagnosis apparatus 1000 may connect voxels having entropy values greater than or equal to a threshold value and determine the connected voxels as being a volume. Furthermore, the ultrasound diagnosis apparatus 1000 may connect voxels having entropy values less than the threshold value and determine the connected voxels as being a volume. Furthermore, the ultrasound diagnosis apparatus 1000 may determine a volume having voxels with entropy values greater than or equal to the threshold value as being a boundary between tissues while determining a volume having voxels with entropy values less than the threshold value as being an interior of tissue.

Furthermore, the ultrasound diagnosis apparatus 1000 may segment the 3D volume of the object into a plurality of volumes by applying a segmentation algorithm to the 3D volume data. Examples of the segmentation algorithm may include Otsu-thresholding, Graph cut, Snake, and Machine Learning, but are not limited thereto. For example, the ultrasound diagnosis apparatus 1000 may detect a plurality of follicles in a 3D volume representing an ovary by using a snake 3D algorithm, determine the detected plurality of follicles as being a plurality of volumes, and label the determined plurality of volumes.

By rendering first and second volumes from among the plurality of volumes based on different 3D rendering properties, the ultrasound diagnosis apparatus 1000 may generate an ultrasound image representing the first and second volumes in different ways (S2630).

For example, the ultrasound diagnosis apparatus 1000 may generate an ultrasound image representing the second volume in a more emphasized manner than the first volume by setting opacity of the first volume to be higher than opacity of the second volume. Furthermore, for example, the ultrasound diagnosis apparatus 1000 may segment the 3D volume into a plurality of pieces of volume data based on an intensity and a gradient of intensity and render 3D volume data by setting a high opacity for volume data having large intensity and large gradient of intensity from among the plurality of pieces of volume data. Accordingly, the ultrasound diagnosis apparatus 1000 may generate an ultrasound image representing a volume having large intensity and gradient of intensity in an emphasized manner.

Furthermore, for example, the ultrasound diagnosis apparatus 1000 may generate an ultrasound image representing the first and second volumes in such a manner as to distinguish them from each other by setting colors of the first and second volumes differently. Furthermore, for example, the ultrasound diagnosis apparatus 1000 may generate an ultrasound image representing the second volume more clearly than the first volume by setting a degree of focus for the second volume to be higher than that for the first volume. For example, the ultrasound diagnosis apparatus 1000 may select at least one volume from among the plurality of volumes and generate an ultrasound image representing the selected volume more clearly than the other volumes by performing 3D filtering on the selected volume.

Examples of a 3D filter may include an anisotropy diffusion filter, a directional filter, and a non-local mean filter, but are not limited thereto. In general, a 3D filter exhibit excellent filtering effects by removing noise while preserving edges but may require high computational costs. Thus, 3D filtering on unnecessary volumes may require a large amount of computations and a long computation time. By applying a 3D filter only to important volumes from among the plurality of volumes, the ultrasound diagnosis apparatus 1000 may provide an ultrasound image representing the important volumes clearly with a small amount of computations.

Furthermore, when the 3D volume of the object is segmented into a plurality of volumes representing internal structures in the 3D volume, the ultrasound diagnosis apparatus 1000 may represent the first and second volumes in different ways by rendering the plurality of volumes based on 3D rendering properties respectively corresponding to the internal structures.

3D rendering properties to be automatically applied respectively to a plurality of volumes may be preset in the ultrasound diagnosis apparatus 1000. For example, 3D rendering properties corresponding to characteristics of each volume may be stored in the ultrasound diagnosis apparatus 1000.

In detail, 3D rendering properties to be applied respectively to internal structures may be preset by the user in the ultrasound diagnosis apparatus 1000. For example, rendering properties may be set so that a bone, an organ, or a skin may be respectively rendered as a white, red, or skin color.

Furthermore, opacity corresponding to an average intensity and an average gradient of intensity may be preset for each volume. For example, opacity corresponding to a volume having an average intensity greater than or equal to a first threshold value and an average gradient of intensity greater than or equal to a second threshold value may be set to 50, and opacity corresponding to a volume having an average intensity less than the first threshold value and an average gradient of intensity less than the second threshold value may be set to 5.

Furthermore, as described above, 3D rendering properties for first and second volumes may be automatically set by the ultrasound diagnosis apparatus 1000 or be selected by the user.

The ultrasound diagnosis apparatus 1000 may render again the 3D volume data with respect to the object based on newly set 3D rendering properties.

The ultrasound diagnosis apparatus 1000 may display the generated ultrasound image (S2640).

The ultrasound diagnosis apparatus 1000 may display an ultrasound image representing re-rendered 3D volume of the object.

FIG. 27 illustrates an example in which the ultrasound diagnosis apparatus 1000 segments a 3D volume of an object into a plurality of volumes based on intensity and a gradient of intensity for a voxel among voxels constituting the 3D volume, according to an embodiment.

As described above, a voxel having a high intensity from among voxels in a 3D volume or a voxel having a large gradient of intensity with its adjacent voxel is most likely to be a meaningful target.

The ultrasound diagnosis apparatus 1000 may determine intensity values and gradients of intensity value with an adjacent voxel respectively for voxels in a 3D volume and segment the 3D volume of an object into a plurality of volumes based on the determined intensity values and gradients of intensity value.

For example, as shown in FIG. 27, the ultrasound diagnosis apparatus 1000 may connect voxels 2730 having intensity values less than a first threshold value 2710 and gradients of intensity value greater than a second threshold value 2720 and determine the connected voxels 2730 as being a first volume. The ultrasound diagnosis apparatus 1000 may also connect voxels 2740 having intensity values greater than the first threshold value 2710 and gradients of intensity value greater than the second threshold value 2720 and determine the connected voxels 2740 as being a second volume. The ultrasound diagnosis apparatus 1000 may also connect voxels 2750 having intensity values less than the first threshold value 2710 and gradients of intensity value less than the second threshold value 2720 and determine the connected voxels 2750 as being a third volume. The ultrasound diagnosis apparatus 1000 may also connect voxels 2760 having intensity values greater than the first threshold value 2710 and gradients of intensity value less than the second threshold value 2720 and determine the connected voxels 2760 as being a fourth volume. The ultrasound diagnosis apparatus 1000 may set different colors respectively for the first through fourth volumes and render 3D volume data based on the set different colors.

Furthermore, for example, the ultrasound diagnosis apparatus 1000 may connect the voxels 2740 having intensity values greater than the first threshold value 2710 and gradients of intensity value greater than the second threshold value 2720 and determine the connected voxels 2740 as being a volume, set a size and a shape of an ROI so that the volume is included in the ROI, and render 3D volume data based on the ROI.

Figure 28A:
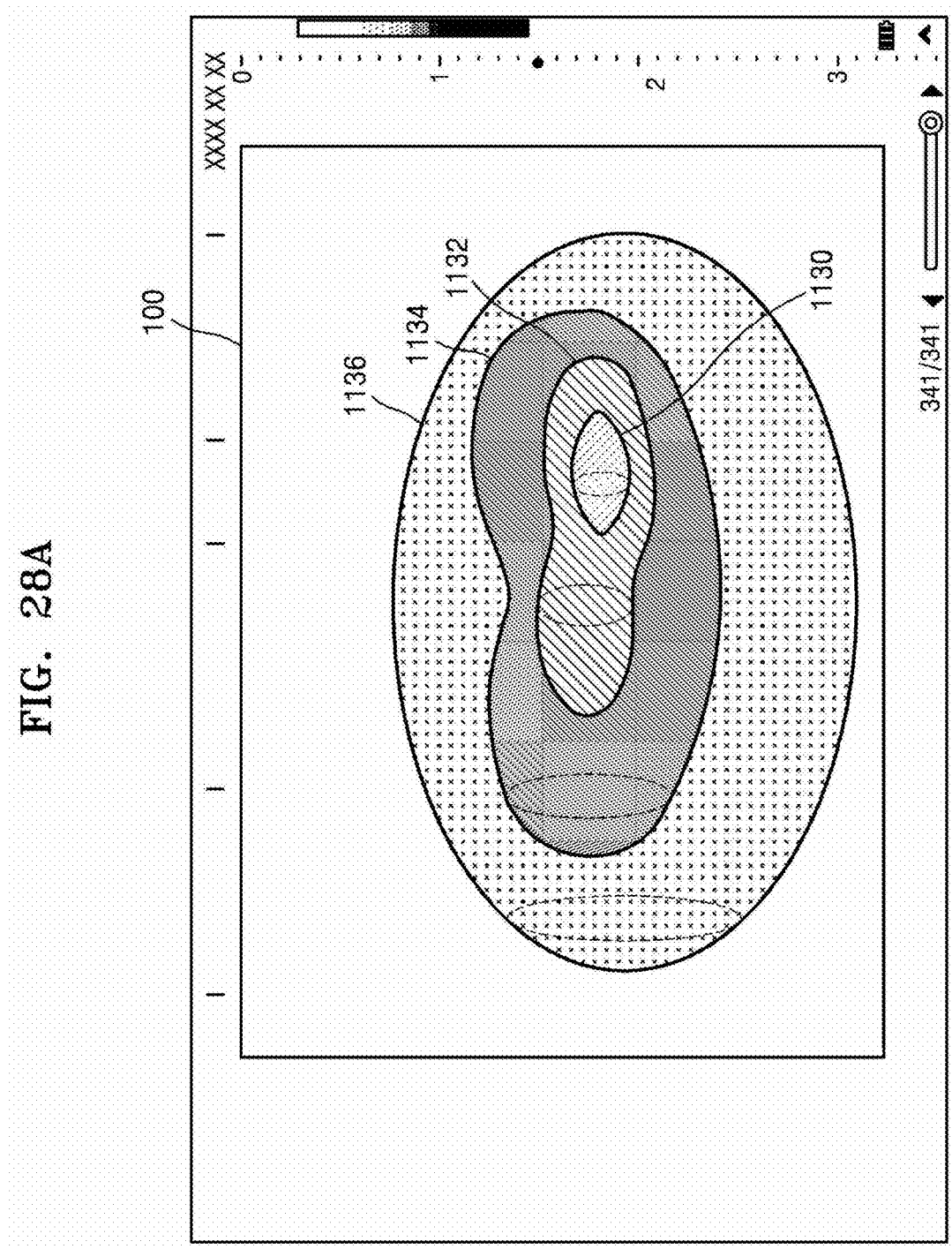
FIG. 28A illustrates an example in which an ultrasound diagnosis apparatus represents a plurality of volumes obtained by segmentation in such a manner as to distinguish the plurality of volumes from one another by rendering the volumes based on different 3D rendering properties, according to an embodiment.

FIG. 28A illustrates an example in which the ultrasound diagnosis apparatus 1000 represents a plurality of volumes obtained by segmentation in such a manner as to distinguish the plurality of volumes from one another by rendering the volumes based on different 3D rendering properties, according to an embodiment Referring to FIG. 28A, the ultrasound diagnosis apparatus 1000 may segment a 3D volume representing a fetus into four volumes, i.e., first through fourth volumes 1130, 1132, 1134, and 1136 based on 3D volume data.

According to an embodiment, the ultrasound diagnosis apparatus 1000 may determine tissues respectively corresponding to the first through fourth volumes 1130, 1132, 1134, and 1136. For example, the ultrasound diagnosis apparatus 1000 may determine the first through fourth volumes 1130, 1132, 1134, and 1136 respectively as being a bone, an organ, a dermis, and an epidermis of the fetus.

The ultrasound diagnosis apparatus 1000 may generate an ultrasound image representing tissues in different colors. For example, a light skin color, a dark skin color, a red color, and a green color may be set for the epidermis, dermis, organ, and bone, respectively, in the ultrasound diagnosis apparatus 1000. Accordingly, the ultrasound diagnosis apparatus 1000 may generate an ultrasound image showing which tissues respectively correspond to the first through fourth volumes 1130, 1132, 1134, and 1136 by setting a light skin color, a dark skin color, a red color, and a green color respectively for the fourth, third, second, and first volumes 1136, 1134, 1132, and 1130 and rendering 3D volume data based on the set colors.

The ultrasound diagnosis apparatus 1000 may represent at least one tissue from among tissues respectively corresponding to the first through fourth volumes 1130, 1132, 1134, and 1136 in a more emphasized manner than the other tissues by setting different opacities according to tissue and rendering 3D volume data based on the set opacities. For example, opacities corresponding to the epidermis, dermis, and bone may be set to 1 in the ultrasound diagnosis apparatus 1000 while opacity corresponding to the organ may be set to 50. Thus, the ultrasound diagnosis apparatus 1000 may generate an ultrasound image representing the second volume 1132 in a more emphasized manner than the fourth, third, and first volumes 1136, 1134, and 1130.

Furthermore, the ultrasound diagnosis apparatus 1000 may represent at least one tissue from among tissues respectively corresponding to the first through fourth volumes 1130, 1132, 1134, and 1136 more clearly than the other tissues by setting different degrees of focus according to tissue and rendering 3D volume data based on the set degrees of focus. For example, degrees of focus corresponding to the epidermis, dermis, and bone may be set to 0 in the ultrasound diagnosis apparatus 1000 while a degree of focus corresponding to the organ may be set to 10. Thus, the ultrasound diagnosis apparatus 1000 may generate an ultrasound image representing the second volume 1132 more clearly than the fourth, third, and first volumes 1136, 1134, and 1130.

Figure 28B:
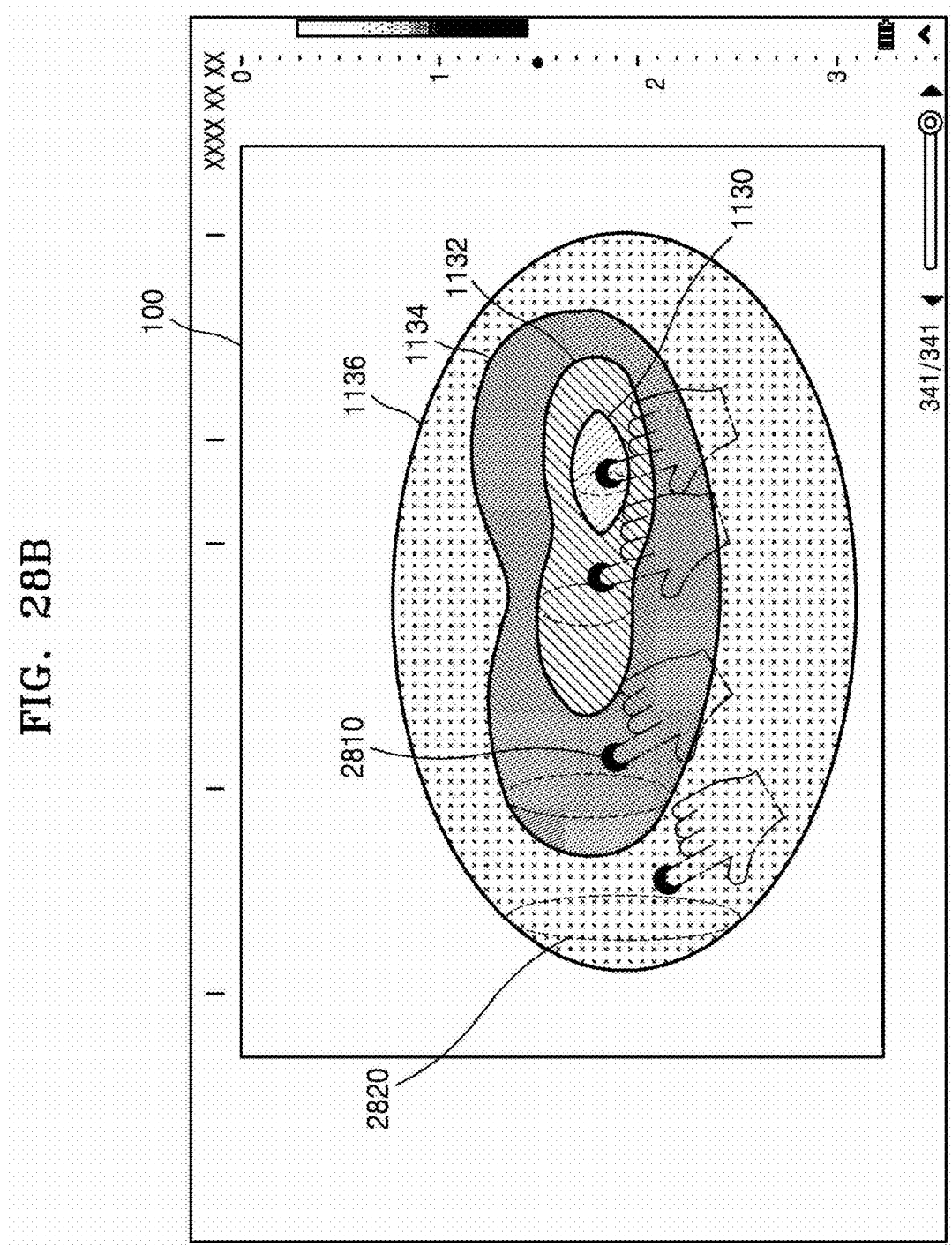
FIG. 28B illustrates an example in which an ultrasound diagnosis apparatus sets an ROI with respect to a volume from among a plurality of volumes obtained by segmentation, according to an embodiment.

FIG. 28B illustrates an example in which the ultrasound diagnosis apparatus 1000 sets an ROI with respect to a volume from among a plurality of volumes obtained by segmentation, according to an embodiment.

Referring to FIG. 28B, when a user input for selecting one point in a 3D volume that is segmented into a plurality of volumes is received, the ultrasound diagnosis apparatus 1000 may determine a volume including the selected point from among the plurality of volumes and set an ROI at a depth of the selected point by taking into account a size and a shape of the determined volume.

For example, if a user input for selecting a point 2810 in a third volume 1134 is received, the ultrasound diagnosis apparatus 1000 may set a region 2820 where a cross-section at a depth of the selected point 2810 intersects the third volume 1134 as an ROI.

The ultrasound diagnosis apparatus 1000 may receive a user input for setting 3D rendering properties with respect to the set ROI. For example, the ultrasound diagnosis apparatus 1000 may receive a user input for setting an opacity, color, or degree of focus with respect to the set ROI.

FIG. 29 is a flowchart of a method, performed by the ultrasound diagnosis apparatus 1000, of setting different 3D rendering properties with respect to a plurality of volumes based on a user input, according to an embodiment.

The ultrasound diagnosis apparatus 1000 may display an ultrasound image showing a plurality of volumes obtained by segmentation (S2910).

The ultrasound diagnosis apparatus 1000 may segment a 3D volume of an object into a plurality of volumes and display an ultrasound image showing contours of the plurality of volumes or the plurality of volumes in different colors. Furthermore, the ultrasound diagnosis apparatus 1000 may display together 3D rendering properties respectively applied to the plurality of volumes.

The ultrasound diagnosis apparatus 1000 may receive a user input for selecting one volume from among the plurality of volumes (S2920).

The ultrasound diagnosis apparatus 1000 may receive a user input for selecting one volume from among the plurality of volumes via a user's touch or a mouse. Furthermore, the ultrasound diagnosis apparatus 1000 may also display a separate user interface for selecting one of the plurality of volumes. The ultrasound diagnosis apparatus 1000 may display the selected volume in such a manner as to distinguish the selected volume from non-selected volumes.

The ultrasound diagnosis apparatus 1000 may receive a user input for setting 3D rendering properties with respect to the volume selected from among the plurality of volumes (S2930).

For example, the ultrasound diagnosis apparatus 1000 may display a user interface for setting 3D rendering properties with respect to the selected volume. The user interface may include a user interface for selecting an opacity, a user interface for selecting a color, a user interface for selecting a degree of focus, and a user interface for selecting a size and a shape of an ROI.

The ultrasound diagnosis apparatus 1000 may receive, via a user interface, a user input for selecting at least one from among an opacity, color, degree of focus, and size and shape of an ROI for the selected volume.

The ultrasound diagnosis apparatus 1000 may generate again an ultrasound image representing the selected volume in a different manner than the other volumes by rendering 3D volume data based on the set 3D rendering properties (S2940).

The ultrasound diagnosis apparatus 1000 may display the regenerated ultrasound image (S2950).

FIG. 30 illustrates an example in which the ultrasound diagnosis apparatus 1000 sets different 3D rendering properties with respect to a plurality of volumes based on a user input, according to an embodiment.

Referring to FIG. 30, the ultrasound diagnosis apparatus 1000 may receive a user input for selecting one volume from among a plurality of volumes and setting 3D rendering properties with respect to the selected volume.

The ultrasound diagnosis apparatus 1000 may receive a user input for selecting one volume from among the plurality of volumes. In this case, the ultrasound diagnosis apparatus

1000 may display the selected volume in such a manner as to distinguish it from non-selected volumes.

Furthermore, the ultrasound diagnosis apparatus 1000 may display together 3D rendering properties respectively set with respect to the plurality of volumes. For example, the ultrasound diagnosis apparatus 1000 may show 3D rendering properties applied to a displayed 3D volume by displaying opacities, colors, degrees of focus, sizes and shapes of ROIs that are respectively set for first through fourth volumes 1130, 1132, 1134, and 1136.

When a user input for selecting one volume is received, the ultrasound diagnosis apparatus 1000 may display user interfaces 3010 and 3020 for setting 3D rendering properties with respect to the selected volume. For example, the ultrasound diagnosis apparatus 1000 may display the user interface 3010 for setting a color with respect to the selected volume and the user interface 3020 for setting opacity with respect thereto. However, embodiments are not limited thereto.

When a user input for setting 3D rendering properties with respect to the selected volume is received, the ultrasound diagnosis apparatus 1000 may generate again an ultrasound image by rendering 3D volume data based on the set 3D rendering properties.

For example, when a user input for setting opacities of the first through fourth volumes 1130, 1132, 1134, and 1136 to 0 and opacity of the third volume 1134 to 10 is received, the ultrasound diagnosis apparatus 1000 may generate an ultrasound image representing only the third volume 1134. Accordingly, the ultrasound diagnosis apparatus 1000 may provide a function for displaying only a volume selected from among the plurality of volumes.

Figure 31:
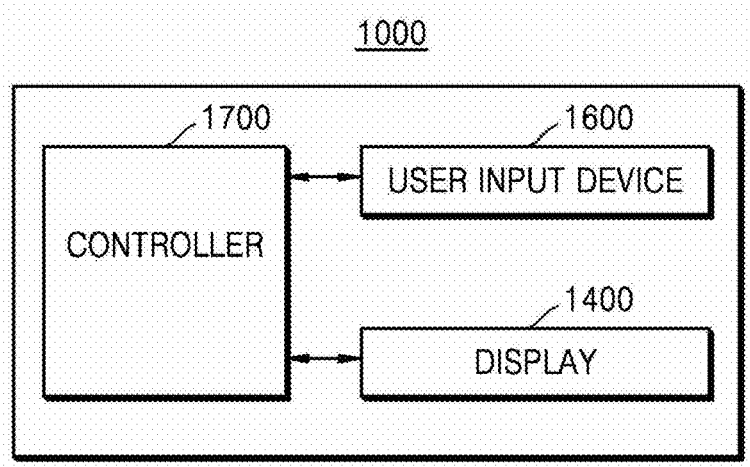
FIG. 31 is a block diagram of a configuration of an ultrasound diagnosis apparatus according to an embodiment.

FIG. 31 is a block diagram of a configuration of an ultrasound diagnosis apparatus 1000 according to an embodiment.

Referring to FIG. 31, the ultrasound diagnosis apparatus 1000 may include a controller 1700, a user input device 1600, and a display 1400.

However, all of the components shown in FIG. 31 are not essential components. The ultrasound diagnosis apparatus 1000 may include more or fewer components than those shown in FIG. 31.

While FIG. 31 shows that the user input device 1600 is separate from the display 1400, the user input device 1600 and the display 1400 may be implemented in an integrated form like a touch screen.

The display 1400 may display an ultrasound image showing a 2D cross-section or 3D region of an object. Furthermore, the display 1400 may display a user interface.

Furthermore, the display 1400 may display a first ultrasound image showing a surface of a 3D region of the object.

The user input device 1600 may receive a user input for controlling the ultrasound diagnosis apparatus 1000. For example, the user input device 1600 may receive a user input for selecting an ROI in the displayed first ultrasound image.

The controller 1700 may control all components of the ultrasound diagnosis apparatus 1000. For example, the controller 1700 may control the display 1400 to display on the set ROI a second ultrasound image showing an internal structure corresponding to the ROI from among internal structures of the 3D region.

In this case, the controller 1700 may generate the second ultrasound image showing an internal structure, based on a gradient of intensity of ultrasound echo signals between points in the 3D region.

Accordingly, the display 1400 may display on the set ROI the second ultrasound image showing an internal structure corresponding to the ROI from among internal structures of the 3D region. The internal structure corresponding to the ROI may include relative positions of structures that are located below the ROI from among structures constituting the 3D region.

In this case, the display 1400 may display the relative positions of the structures located below the ROI by showing contours of the structures located below the ROI at different depths.

The structures may include at least one of a skin, an organ, a blood vessel, a bone, and a cavum, but are not limited thereto.

Furthermore, the user input device 1600 may receive a user input for changing an ROI. In this case, the controller 1700 may control the display 1400 to display on the changed ROI a second ultrasound image showing an internal structure corresponding to the changed ROI.

Thus, the display 1400 may display, on the changed ROI, the second ultrasound image showing the internal structure corresponding to the changed ROI.

Furthermore, the user input device 1600 may receive a user input for setting a depth of an internal structure to be displayed on an ROI. In this case, the controller 1700 may control the display 1400 to display a portion of the internal structure located down from the set depth by setting opacity values at points located above the set depth, from among points in a 3D region, to less than or equal to a reference value. Accordingly, the display 1400 may display a portion of the internal structure corresponding to the ROI, which is located below the set depth, on the ROI.

The user input device 1600 may receive a user input for setting a plurality of ROIs according to a depth of the 3D region. In this case, the controller 1700 may control the display 1400 to display on an ROI a second ultrasound image showing an internal structure corresponding to the ROI by respectively setting different rendering parameters for the set ROIs. According to control by the controller 1700, the display 1400 may display on the ROI the second ultrasound image showing an internal structure corresponding to the ROI by respectively setting different rendering parameters for the set ROIs. In this case, the rendering parameters may include at least one of opacity, degree of focus, and color, but are not limited thereto.

Figure 32:
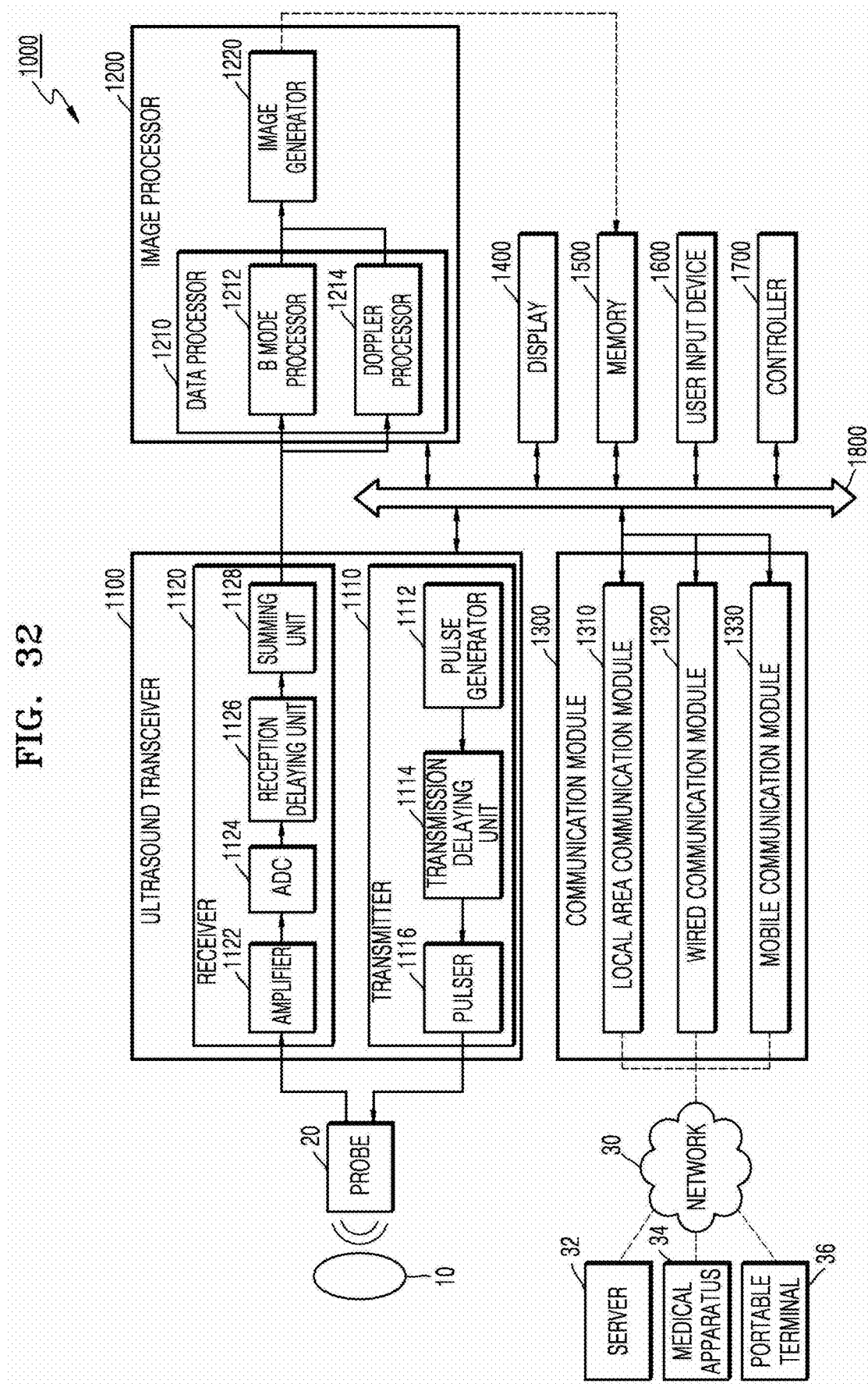
FIG. 32 is a block diagram of a configuration of a system including an ultrasound diagnosis apparatus according to an embodiment.

FIG. 32 is a block diagram of a configuration of a system including an ultrasound diagnosis apparatus 1000 according to an embodiment. Referring to FIG. 32, the ultrasound diagnosis apparatus 1000 may include a probe 20, an ultrasound transceiver 1100, an image processor 1200, a communication module 1300, a display 1400, a memory 1500, a user input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses 1000 may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 included in a data processor 1210 extracts B mode components from ultrasound data and processes the B mode components. An image generator 1220 may generate an ultrasound image indicating signal intensities as brightness based on the extracted B mode components 1212.

Similarly, a Doppler processor 1214 included in the data processor 1210 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc.

Furthermore, the ultrasound diagnosis apparatus 1000 may utilize web storage or a cloud server that performs the storage function of the memory 1500 online.

The user input device 1600 refers to a means via which a user inputs data for controlling the ultrasound diagnosis apparatus 1000. The user input device 1600 may include hardware components, such as a keypad, a mouse, a touch pad, a touch screen, and a jog switch. However, embodiments are not limited thereto, and the user input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the user input device 1600 shown in FIG. 32.

All or some of the probe 20, the ultrasound transceiver 1100, the image processor 1200, the communication module 1300, the display 1400, the memory 1500, the user input device 1600, and the controller 1700 may be implemented as software modules. Furthermore, at least one selected from the ultrasound transceiver 1100, the image processor 1200, and the communication module 1300 may be included in the controller 1700. However, embodiments of the present invention are not limited thereto.

Embodiments may be implemented through non-transitory computer-readable recording media having recorded thereon computer-executable instructions such as program modules that are executed by a computer. The non-transitory computer-readable recording media may be any available media that can be accessed by a computer and include both volatile and nonvolatile media and both detachable and non-detachable media. Furthermore, the non-transitory computer-readable recording media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and may include any information transmission media.

Furthermore, in the present specification, the term "unit" may be a hardware component such as a processor or circuit and/or a software component that is executed by a hardware component.

The above description is provided for illustration, and it will be understood by those of ordinary skill in the art that various changes in form and details may be made therein without departing from essential features and the spirit and scope of the present inventive concept as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The scope of the present inventive concept is defined not by the detailed description thereof but by the appended claims, and all the changes or modifications within the scope of the appended claims and their equivalents will be construed as being included in the present inventive concept.

What is claimed is:

1. An ultrasound diagnosis apparatus comprising:
   a display configured to display a first ultrasound image showing an object;
   a user input device configured to receive a first user input for setting a region of interest (ROI) on the first ultrasound image and a second user input for setting a first depth; and
   a controller configured to generate a second ultrasound image showing a three-dimensional (3D) volume of the object by applying a first opacity with respect to the ROI at the first depth and, a second opacity with respect to the ROI at a second depth smaller than the first depth, and
   control the display to display the generated second ultrasound image,
   wherein the first opacity is higher than the second opacity, and
   wherein the second ultrasound image represents an internal structure of the 3D volume, which is located at the first depth, on the ROI, and represents a surface of the 3D volume on a region other than the ROI.

2. The ultrasound diagnosis apparatus of claim 1, wherein the first depth comprises a first depth interval in the 3D volume.

3. The ultrasound diagnosis apparatus of claim 1, wherein the controller is further configured to control the display to display an indicator representing a direction of a depth for which the first opacity and the second opacity are to be set, respectively.

4. The ultrasound diagnosis apparatus of claim 1, wherein the display is further configured to display a plurality of ultrasound images showing different cross-sections of the object, and
   wherein the user input device is further configured to receive a user input for selecting one of the plurality of ultrasound images as the first ultrasound image.

5. The ultrasound diagnosis apparatus of claim 1, wherein the display is further configured to display a plurality of images representing patterns of opacities according to depths,
   wherein the user input device is further configured to receive a user input for selecting one of the plurality of images,
   wherein the controller is further configured to set the first opacity and the second opacity among the opacities based on the user input for selecting one of the plurality of images.

6. The ultrasound diagnosis apparatus of claim 1, wherein the first ultrasound image is an ultrasound image showing the 3D volume of the object.

7. The ultrasound diagnosis apparatus of claim 1, wherein the controller controls the display to display a user interface for setting at least one from among a shape and a size of the ROI, and
   set the ROI based on a user input for setting the at least one from among the shape and the size of the ROI by using the user interface.

8. A method of displaying an ultrasound image, the method comprising:
   displaying a first ultrasound image showing an object;
   receiving a first user input for setting a region of interest (ROI) on the first ultrasound image and a second user input for setting a first depth;

generating a second ultrasound image showing a three-dimensional (3D) volume of the object by applying a first opacity with respect to the ROI at the first depth and a second opacity with respect to the ROI at a second depth smaller than the first depth; and displaying the generated second ultrasound image, wherein the first opacity is higher than the second opacity, and wherein the second ultrasound image represents an internal structure of the 3D volume, which is located at the first depth, on the ROI, and represents a surface of the 3D volume on a region other than the ROI.

9. The method of claim 8, wherein the first depth comprises a first depth interval in the 3D volume.

10. The method of claim 8, wherein the displaying of the first ultrasound image showing the object comprises displaying an indicator representing a direction of a depth for which the first opacity and the second opacity are to be set, respectively.

11. The method of claim 8, wherein the displaying of the first ultrasound image showing the object comprises:

displaying a plurality of ultrasound images showing different cross-sections of the object;

receiving a user input for selecting one of the plurality of ultrasound images as the first ultrasound image; and displaying the selected first ultrasound image.

12. The method of claim 8, further comprising:

displaying a plurality of images representing patterns of opacities according to depths, receiving a user input for selecting one of the plurality of images, and setting the first opacity and the second opacity among the opacities based on the user input for selecting one of the plurality of images.

13. The method of claim 8, wherein the first ultrasound image is an ultrasound image showing the 3D volume of the object.

14. The method of claim 8, further comprising:

displaying a user interface for setting at least one from among a shape and a size of the ROI, and setting the ROI based on a user input for setting the at least one from among the shape and the size of each of the ROI by using the user interface.

* * * * *